US006307075B2

(12) United States Patent
Norman et al.

(10) Patent No.: US 6,307,075 B2
(45) Date of Patent: *Oct. 23, 2001

(54) THERAPEUTICALLY EFFECTIVE 1α, 25-DIHYDROXYVITAMIN $D_3$ ANALOGS

(75) Inventors: Anthony W. Norman; William H. Okamura, both of Riverside, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/452,282

(22) Filed: Nov. 30, 1999

Related U.S. Application Data

(60) Division of application No. 09/074,565, filed on May 7, 1998, now Pat. No. 6,121,469, and a continuation-in-part of application No. 08/706,356, filed on Aug. 30, 1996, now abandoned, and a continuation-in-part of application No. 08/558,717, filed on Nov. 16, 1995, now abandoned, which is a continuation-in-part of application No. 08/249,385, filed on May 25, 1994, now abandoned, which is a continuation of application No. 08/173,561, filed on Dec. 23, 1993, now abandoned.
(60) Provisional application No. 60/060,173, filed on Sep. 26, 1997.

(51) Int. Cl.[7] ............................................. C07C 407/00
(52) U.S. Cl. ................................................. 552/653
(58) Field of Search ............................................. 552/653

(56) References Cited

U.S. PATENT DOCUMENTS

| | | | |
|---|---|---|---|
| 4,670,190 | 6/1987 | Hesse et al. | 260/397.2 |
| 4,804,502 | 2/1989 | Baggiolini et al. | 260/397.2 |
| 5,087,619 | 2/1992 | Baggiolini et al. | 514/167 |
| 5,145,846 | 9/1992 | Baggiolini et al. | 514/167 |
| 5,362,719 | 11/1994 | Godtgredsen | 514/167 |
| 5,378,695 | 1/1995 | Calverley et al. | 514/167 |
| 5,395,829 | 3/1995 | Hollck | 514/167 |
| 5,401,732 | 3/1995 | Calverley et al. | 514/167 |
| 5,403,832 | 4/1995 | Posner et al. | 514/167 |
| 5,436,401 | 7/1995 | Kato et al. | 552/610 |
| 5,552,392 | * 9/1996 | DeLuca et al. | 514/167 |
| 5,612,325 | 3/1997 | Hansen et al. | 514/167 |
| 5,710,142 | 1/1998 | Calverley et al. | 514/167 |

FOREIGN PATENT DOCUMENTS

| | | |
|---|---|---|
| 18649/92 | 6/1992 | (AU) . |
| 4-89473 | 3/1992 | (JP) . |
| 4-89474 | 3/1992 | (JP) . |
| 6-72994 | 3/1994 | (JP) . |
| 6-256300 | 9/1994 | (JP) . |

OTHER PUBLICATIONS

Norman et al., "Selective biological response by target organs (intestine, kidney and bone) to 1,25–dihydroxyvitamin D3 and two analogues." Cancer Res., vol. 53, pp. 3935–3942, Sep. 1, 1993.*

Figadere et al., "Arocalciferols: Synthesis and biological evaluation of aromatic side–chain analogues of 1.alpha., 25–dihydroxyvitamin D3.", J. Med. Chem., vol. 34, pp. 2452–2463, 1991.*

Craig et al., J. Org. Chem., vol. 57, pp. 4374–4380, 1992.*

PCT WO 94/07851 Apr. 14, 1994 C07C401/00, A61K31/59 Hansen, et al., Novel Vitamin D Analogues.

* cited by examiner

*Primary Examiner*—Barbara P. Badio
(74) *Attorney, Agent, or Firm*—Hana Verny

(57) ABSTRACT

Novel analogs of 1α,25-dihydroxyvitamin $D_3$ which are selective agonists for the genomic responses or agonists or antagonists for the rapid cellular responses in a wide array of diseases in which 1α,25-dihydroxyvitamin $D_3$ or its prodrugs are involved. Novel analogs have general formulae represented by compounds of groups I–V. A method for treatment and prevention of diseases connected with the endocrine system.

3 Claims, 4 Drawing Sheets

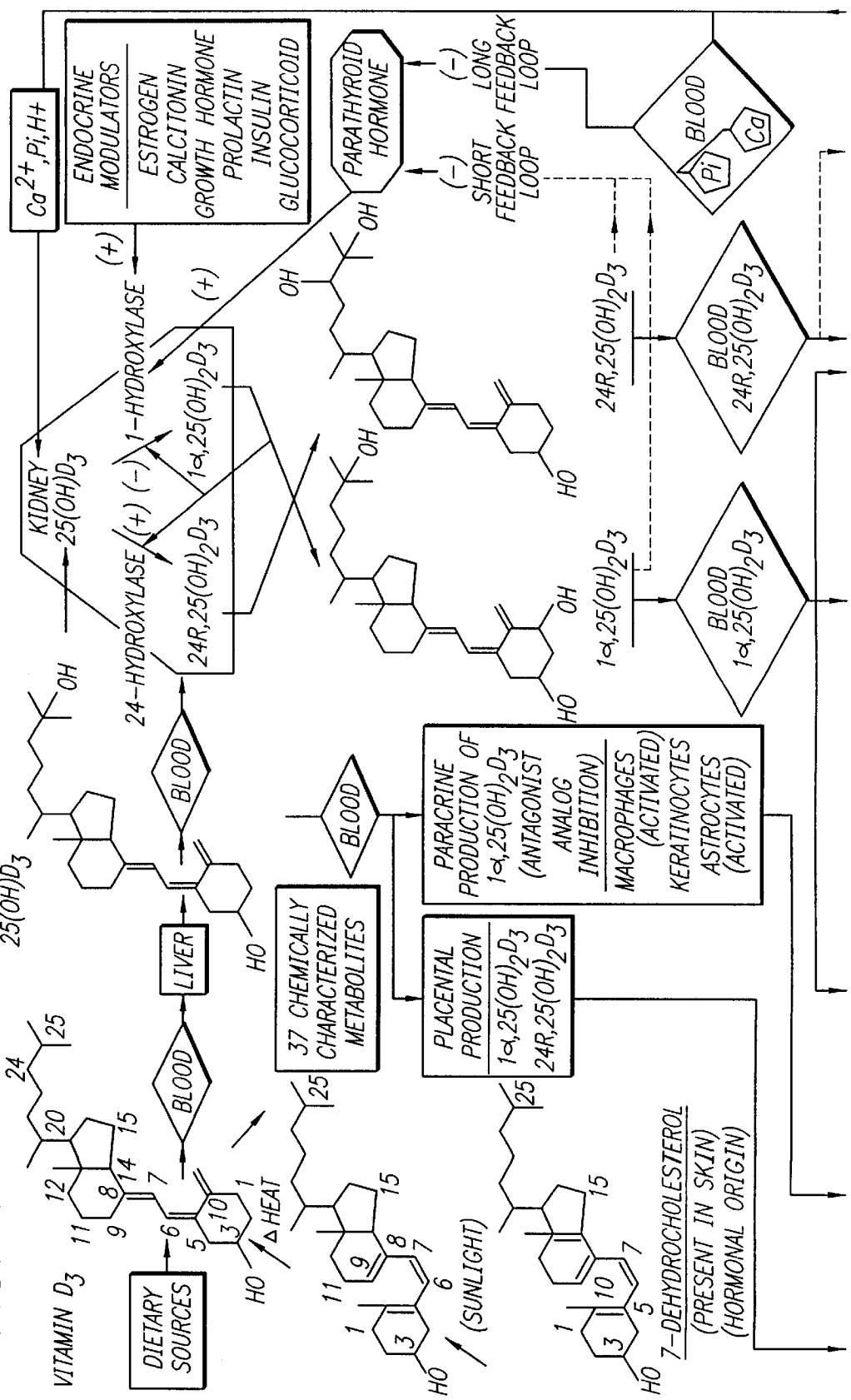
FIG. 1-A

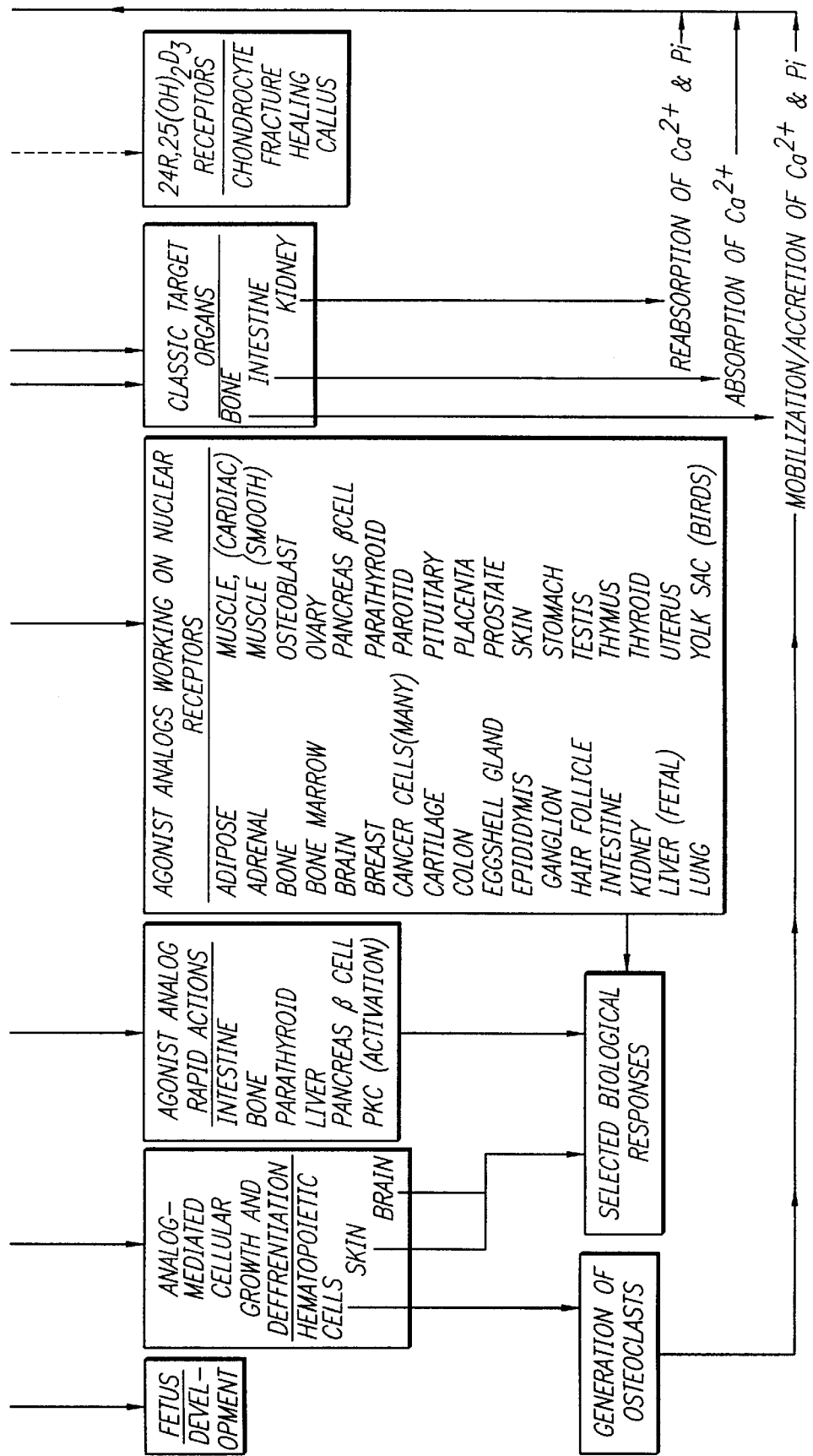
FIG. 1-B

THERAPEUTICALLY EFFECTIVE 1α, 25-DIHYDROXYVITAMIN D₃ ANALOGS

This application is a divisional of application Ser. No. 09/074,565, filed May 7, 1998, now U.S. Pat. No. 6,121,469, which is based on provisional application Ser. No. 60/060,173, filed Sep. 26, 1997 and is a continuation-in-part of application Ser. No. 08/706,356, filed Aug. 30, 1996, now abandoned, and of application Ser. No. 08/558,717, filed Nov. 16, 1995, now abandoned, which are continuations-in-part of application Ser. No. 08/249,385, filed May 25, 1994, now abandoned, which is a continuation of application Ser. No. 08/173,561, filed Dec. 23, 1993, now abandoned.

This invention was made with government support under Research Grant Nos. DK-09012 and DK-16,595, awarded by the National Institute of Health. The government has certain rights in this invention.

BACKGROUND OF THE INVENTION

1. Field of Invention

The current invention concerns novel analogs of 1α,25-dihydroxyvitamin $D_3$ which are agonists for both the slow genomic responses and agonists of rapid nongenomic responses and analogs which act solely as agonists or antagonists for the rapid nongenomic cellular responses in a wide array of diseases in which 1α,25-dihydroxyvitamin $D_3$ or its prodrugs are involved. In particular, the invention concerns analogs depicted by the general formulae I–V.

2. Background Art and Related Art Disclosures

Vitamin $D_3$ is a secosteroid which is responsible for a wide variety of biological responses in higher animals. These biologicals include maintenance of calcium homeostasis, immunomodulation and selected cell differentiation. Vitamin $D_3$, itself, is biologically inert. However, metabolism of vitamin $D_3$ first to 25-dihydroxyvitamin $D_3$ and then to such metabolites as 1α,25-dihydroxyvitamin $D_3$ [1α,25(OH)$_2$D$_3$] results in the formation of biologically active compounds which are responsible for the wide array of biological responses which are observed as part of the vitamin D endocrine system.

A great number of normal physiological functions depends on vitamin D metabolism. Its deficiencies and/or overproduction can result in severe disbalance of homeostasis and in diseases of bone, the immune system, kidney, liver, brain, skin and other organs. Overproduction of 25(OH)D$_3$ or 1α,25(OH)$_2$D$_3$ produces toxicity and hypercalcemia. Both these disbalances have very serious impact on the well-being and health of the individual.

It would, therefore, be advantageous to have available substitute compounds able to act in the same way as 1α,25(OH)$_2$D$_3$ but lacking the undesirable secondary symptoms.

1α,25(OH)$_2$D$_3$ generates many biological genomic responses by interaction with nuclear receptors. These responses which result in gene expression of the appropriate protein are slow, typically occurring within several hours to several days. The result of this interaction with nuclear receptors is the regulation of gene transcription (*Crit. Rev. Eukar. Gene Exp.*, 2:65–109 (1992), *Annu. Rev. Nutr.*, 11:189–216 (1991), *Vitamin D: Gene Regulation, Structure-Function Analysis and Clinical Application*, (Norman, A. W., Bouillon, R., and Thomasset, M., Eds.) pp. 146–154, Walter de Gruyter, Berlin (1991)). The nuclear receptor for 1α,25(OH)$_2$D$_3$ has been shown to be present in 30 different tissues and it belongs to the same family of proteins which includes receptors for the steroid hormones, and retinoic acid and thyroxine (*Crit. Rev. Eukar. Gene Exp.*, 2:65–109 (1992), *FASEB J.*, 2:3043–3053 (1988), *Endocr. Rev.*, 3:331–366 (1982)).

In addition to slow genomic responses, a subset of biological responses mediated by 1α,25((OH)$_2$D$_3$ occur via a rapid nongenomic mechanism which was recently discovered (*Vitamin D: Gene Regulation, Structure-Function Analysis and Clinical Application*, (Norman, A. W., Bouillon, R., and Thomasset, M., Eds.) pp. 146–154, Walter de Gruyter, Berlin (1991) and *Endocrinology*, 115:1476–1483 (1984)). These rapid nongenomic responses include the rapid hormonal stimulation of intestinal $Ca^{2+}$ transport known as transcaltachia (*Endocrinology*, 118:2300–2304 (1986), *J. Steroid Biochem*, 25:905–909 (1986) and *Biochem. Biophys. Res. Commun.*, 166:217–222 (1990) which involves the opening of $Ca^{2+}$ channels as described in *J. Biol. Chem.*, 264:20265–20274 (1989). Other rapid nongenomic cellular responses which are mediated by 1α,25((OH)$_2$D$_3$ include opening of voltage-gated $Ca^{2+}$ channels in rat osteosarcoma cells (*Endocrinology*, 127:2253–2262 (1990), *Am. J. Physiol.*, 249:F117–F123 (1985)) as well as other rapid effects in kidney (*FEBS Lett.*, 259:205–208 (1989)), liver (*Endocrinology*, 127:2738–2743 (1990)), parathyroid cells (*J. Biol. Chem.*, 264:20403–20406 (1989)) and intestine (*J. Bone Min. Res.*, 7:457–463 (1992)).

The rapid actions of 1α,25(OH)$_2$D$_3$ on the cell membrane seem to regulate cell biological function and interact with other membrane-mediated kinase cascades or to be involved in cross-talk with the cell nucleus to modify genomic responses of cell differentiation and proliferation as described in Norman A. W., et al, *Endocrinology*, (Feb. 1998).

The family of enzymes known as mitogen activated protein kinase (MAP kinase) belongs to the family of serine/threonine protein kinases which can be activated by phosphorylation of a tyrosine residue induced by mitogens or cell differentiating agents, (*Trends Biochem. Sci.*, 17:233–238 (1992); *J. Cell Biol.*, 12:1079–1088 (1993)). MAP kinase integrates multiple intracellular signals transmitted by various second messengers, (*J. Biol. Chem.*, 270:3642–3647 (1995), and regulates many cellular functions by phosphorylation of several cytoplasmic kinases and nuclear transcription factors including the EGF receptor, c-Myc and c-Jun, (*Science*, 260:315–319 (1993)).

It has now been discovered that certain analogs of 1α,25(OH)$_2$D$_3$ have biological activities similar to those of 1α,25(OH)$_2$D$_3$ without having, at the same time, undesirable secondary symptoms. Moreover, their biological activities are dependent on their respective chemical structures and these analogs are, therefore, more specific in their biological action. Some of these analogs act both as agonists of slow genomic responses and agonists of rapid responses while the others act solely as agonists or antagonists for rapid nongenomic responses.

It is, therefore, a primary object of this invention to provide specific agonists for generation of regulatory or cellular proteins via regulation of gene expression, that is by slow genomic responses, as well as up or down regulation of these slow genomic responses via agonists or antagonists of the rapid nongenomic responses.

All patents, patent applications and publications cited herein are hereby incorporated by reference.

SUMMARY

One aspect of the current invention is a compound depicted by the general formula I or a pharmaceutically acceptable salt thereof.

Another aspect of the current invention is a compound of the formula I comprising substituents listed in Table 1.

Another aspect of the current invention is a compound depicted by the general formula II or a pharmaceutically acceptable salt thereof.

Another aspect of the current invention is a compound of the formula II comprising substituents listed in Table 2.

Still another aspect of the current invention is a compound depicted by the general formula III or a pharmaceutically acceptable salt thereof.

Another aspect of the current invention is a compound of the formula III comprising substituents listed in Table 3.

Still yet another aspect of the current invention is a compound depicted by the general formula IV a pharmaceutically acceptable salt thereof.

Another aspect of the current invention is a compound of the formula IV comprising substituents listed in Table 4.

Yet another aspect of the current invention is a compound depicted by the general formula V or a pharmaceutically acceptable salt thereof.

Still another aspect of the current invention is the compound of the formula V comprising substituents listed in Table 5.

Another aspect of the current invention is an analog selected from the group consisting of analog DE, DF, EV, HQ, /HR, LO, JM (their names to be listed), namely $1\alpha,25(OH)_2$-7-dehydrocholesterol; analog JN, namely, $1\alpha,25(OH)_2$-Lumisterol$_3$; analog JO, namely, $1\alpha,25(OH)_2$-Pyrocalciferol$_3$; analog JP, namely, $1\alpha,25(OH)_2$-Isopyrocalciferol$_3$; analog HS, namely, $1\alpha, 18,25(OH)_3$-$D_3$; analog GE, namely, 14-epi-$1,25(OH)_2$-$D_3$; analog GF, namely, 14-epi-$1,25(OH)_2$-pre-$D_3$; analog JR, namely, $1\alpha,25(OH)_2$-7,8-cis-$D_3$; analog JS, namely, $1,25(OH)_2$-5,6-trans-7,8-cis-$D_3$; analog HH, namely, $1\beta,25(OH)_2$-Epi-$D_3$; analog HJ, namely, $1\alpha,25(OH)_2$-3-Epi-$D_3$; analog JV, namely, (1S,3R,6S)-7,19-Retro-$1,25(OH)_2$-$D_3$ or ($6\beta$)-1,25vinylallene); analog JW, namely, (1S,3R,6R)-7,19-Retro-$1,25(OH)_2$-$D_3$, or [($6\alpha$)-1,25-vinylallene]; analog JX, namely, 22-(p-hydroxyphenyl)-23,24,25,26,27-pentanor-$D_3$; analog JY, namely, 22-(m-hydroxyphenyl)-23,24,25,26,27-pentanor-$D_3$; analog IB namely 23-[m(dimethylhydroxyethyl)phenyl]-22-yne-24,25,26,27-tetranor-$1\alpha$-hydroxy-$D_3$, analog LO, namely $14\alpha,15\alpha$-methano-$1\alpha,25(OH)_2D_3$.

Still another aspect of the current invention is a process for preparation of analogs of general formulae I–V and salts thereof.

Still yet another aspect of the current invention is a method for eliciting slow genomic responses by interaction of the analogs of the invention with the nuclear receptor for $1\alpha,25(OH)_2D_3$ which is present in target organ cells.

Still yet another aspect of the current invention is a method for eliciting rapid nongenomic responses which include a rapid stimulation and release of calcium ions by intestine, kidney, parathyroid cells, liver and other organs during homeostatic responses and correction of pathological conditions in which the vitamin $D_3$ or $1\alpha,25(OH)_2D_3$ are involved by analogs of the invention.

Another aspect of this current invention is the rapid nongenomic stimulation of mitogen-activated protein kinase (MAP-kinase) in chick intestinal and human leukemic cells.

Still yet another aspect of the current invention is a method for rapid nongenomic stimulation of mitogen-activated protein kinase (MAP-kinase) in intestinal or leukemic cells by analogs of the invention.

Still another aspect of the invention is a method for treatment of diseases caused by deficiencies or overproduction of $1\alpha,25(OH)_2D_3$ or treatment of its functional deficiencies by providing a subject in need of correcting these deficiencies with an agonist analog of the $1\alpha,25(OH)_2D_3$ represented by formulae I–V in amount sufficient to ameliorate the disease.

Still another aspect of the current invention is a method for selective inhibition of vitamin D-related rapid nongenomic responses.

Another aspect of the present invention involves controlling the rapid nongenomic responses mediated by $1\alpha,25(OH)_2D_3$ by treating the subject in need of such treatment with an antagonist analog which is $1\beta,25(OH)_2D_3$.

Another aspect of the current invention is $1\alpha,25$-dihydroxyvitamin D3 and its 6-s-cis analogs which are selective agonists for the activation of MAP-kinase.

Definitions

As defined here:

"Steroid-like conformation", the seco-B ring can assume, in the limit, one of two conformations as a consequence of rotation about the carbon 6–7 single bond; in the 6-s-cis orientation (C) the A ring is related to the C/D rings as in the conventional steroid orientation, referred to here as the "steroid-like conformation" and when the conformation is in the 6-s-trans orientation (D), the A ring is present in an "extended conformation."

"Alpha", or "$\alpha$", "beta" or "$\beta$" position or configuration mean the absolute configuration notation used in steroids, such as cholesterol or in natural products; the term "$\alpha$" or "$\beta$" mean the carbon or the substituent, as the case may be, within the context of the structural formulas presented herein.

"Cis" or "trans" terms are used in reference to vitamin $D_3$ which is 5,6-cis/7,8-trans. Terms "Z" or "E" designations are less desirable because these designations are reversed when a C1 hydroxyl is present.

"6-trans orientation" means a geometrical orientation resulting in an isomer having a spatial arrangement where a given atom positioned on each side of the carbon-carbon axis is in opposite location relative to the carbon axis.

"Agonist" means a compound capable of combining with receptors to initiate the compound's actions. The agonist possesses affinity and intrinsic activity.

"Antagonist" means a compound which prevents, blocks, neutralize or impede the action of agonist.

"Conformationally flexible" means analogs wherein a connection between a specified two carbons permits rotation of 360 degrees with respect to each other. Typically, two carbons exist in this configuration.

"Conformationally restricted" means analogs wherein a connection between a specified two carbon does not permit rotation of 360 degrees with respect to each other. There is a degree of variability in conformationally restricted carbons. Two carbon in this context can, therefore, be more or less conformationally restricted and be able to rotate more or less.

"6-cis-orientation" means a geometrical orientation resulting in a spatial arrangement where a given atom, positioned on each side of the carbon-carbon axis is in the same side location relative to the carbon axis.

"6-s-cis" means, in this context, that there is a double bond between carbons C5–C6 and that C5–C6 carbons exist in fixed cis relation to each other.

BRIEF DESCRIPTION OF DRAWINGS

FIG. 1 represents summary of the vitamin D endocrine system.

DETAILED DESCRIPTION OF THE INVENTION

Figure 2:
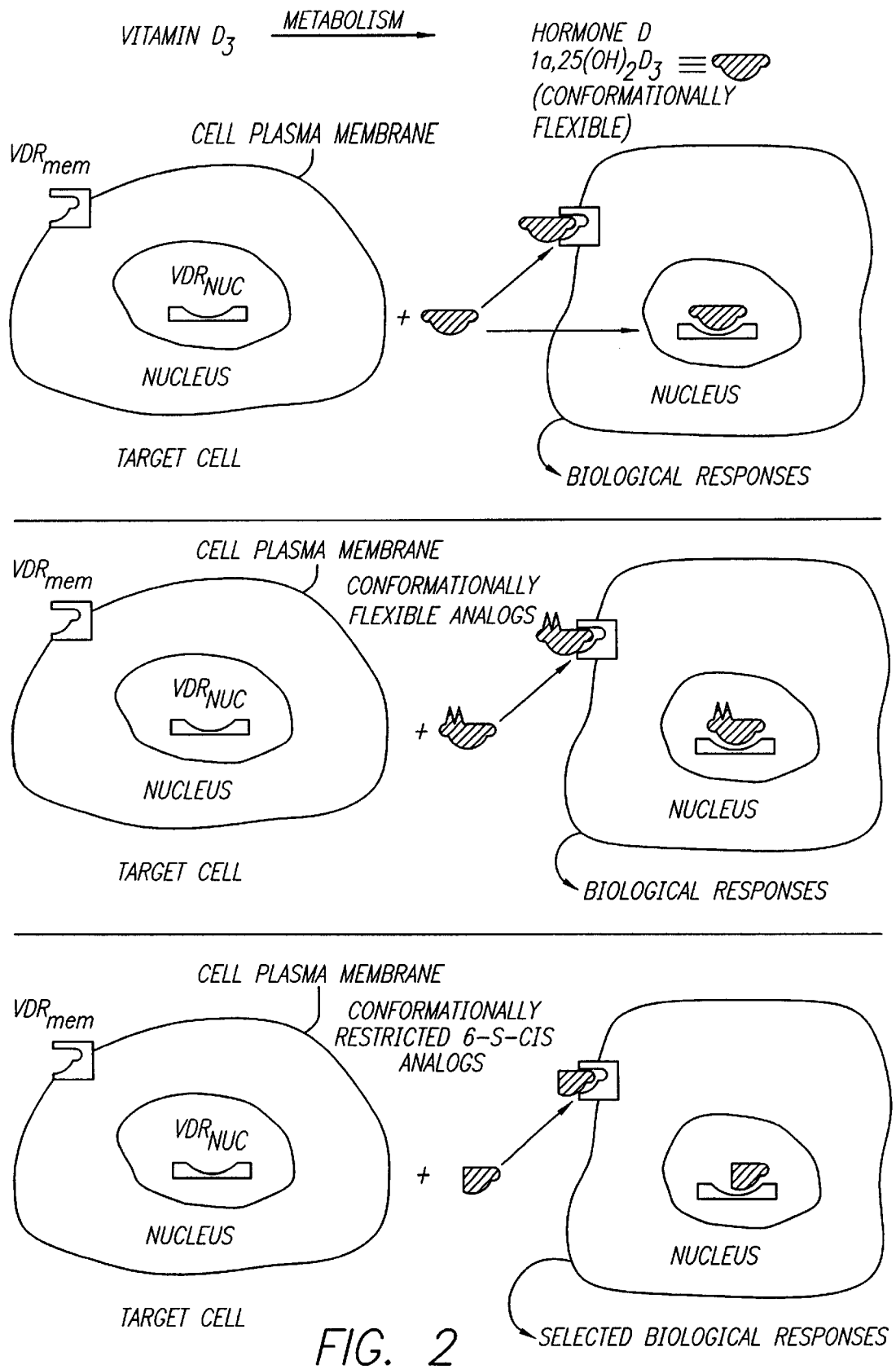
FIG. 2 represents a model describing the general mode of action of 1α,25(OH)₂D₃.

The present invention provides analogs of 1α,25(OH)₂D₃ which are able to treat and ameliorate diseases and conditions connected with the vitamin D metabolism. These analogs effectively control gene expression via slow genomic responses as well as rapid nongenomic cellular responses typically mediated by 1α,25dihydroxyvitamin D₃ [1α,25(OH)₂D₃]. The current invention, therefore, relates to novel biologically active analogs of 1α,25(OH)₂D₃. These analogs are agonists of slow genomic responses or selective agonists or antagonists of rapid nongenomic cellular responses, depending on their chemical structures.

These analogs, their structures, their preparation and their chemical, physical and biological profiles are described in the following Tables, Reaction Schemes and in Examples.

I. 1α,25-Dihydroxy vitamin D₃ Analogs

There are five groups of vitamin 1α,25(OH)₂D₃ analogs which have the above described biological activity as agonists of the slow genomic responses or agonists or antagonists of the rapid nongenomic responses.

The group I is represented by compounds having a general formula I (I)

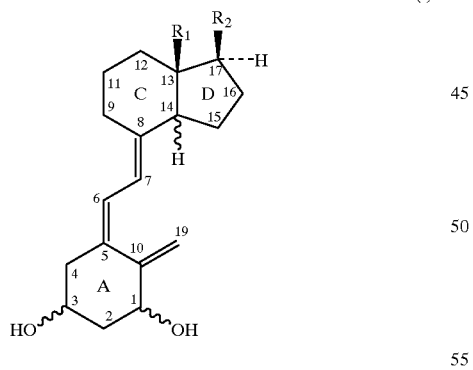

wherein C1 and C3 are configurational isomers α and β which may be the same or different in α-α, β-β, α-β or β-α configuration;
wherein C5–C6 double bond is cis or trans;
wherein C7–C8 double bond is cis or trans;
wherein C14 hydrogen is α or β;
wherein C16–C17 is a single or double bond;
wherein R₁ is CH₃ or CH₂OH;
wherein R₂ is a substituent selected from the group consisting of substituents I-1 through I-10

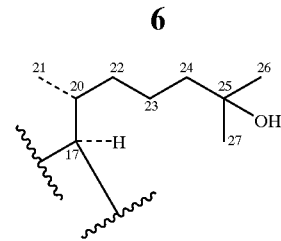
I-1

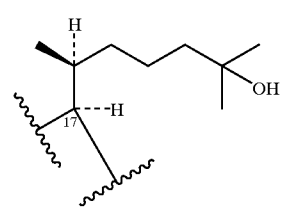
I-2

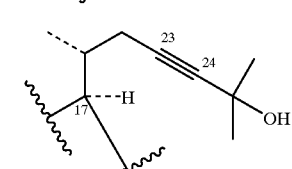
I-3

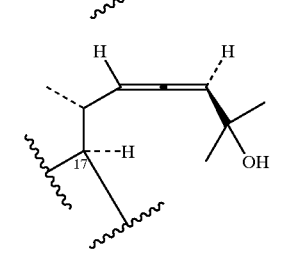
I-4

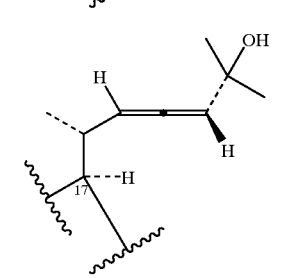
I-5

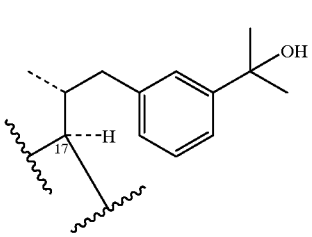
I-6

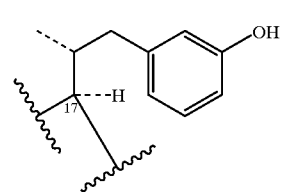
I-7

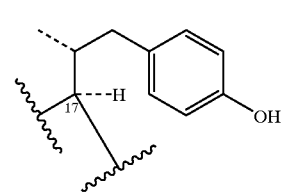
I-8

-continued

I-9

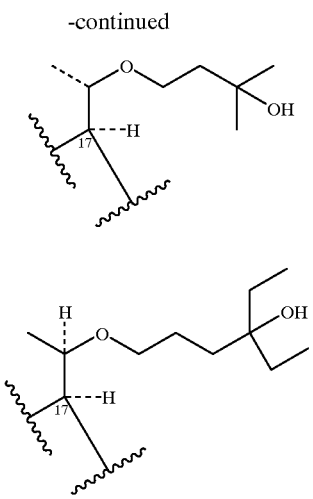

I-10 with the proviso that
when $R_1$ is $CH_3$ and when $C_1$ and C3 are α-β, then $R_2$ is not the substituent I-1, I-2, I-3, I-9 or I-10; or
when $C_1$ is in the α orientation and C3 is in the β orientation, C5–C6 double bond is cis or trans and C7–C8 double bond is trans, $R_1$ is $CH_3$, C14 hydrogen is in the α orientation, C16–C17 is a single or double bond, then $R_2$ is not the substituent I-1, I-2, I-3, I-4, I-5, I-9 or I-10; or when $C_1$ is in the β orientation, C3 is in the β orientation, C5–C6 double bond is cis, C7–C8 double bond is trans, $R_1$ is $CH_3$, C14 hydrogen is in α orientation, C16–C17 is a single bond, then $R_2$ is not the substituent I-1; or when $C_1$ is in the α orientation, C3 is in the β orientation, C5–C6 double bond is cis, C7–C8 double bond is trans, $R_1$ is $CH_2OH$, C14 hydrogen is in the α orientation, C16–C17 is a single bond, then $R_2$ is not the substituent I-1; or when $C_3$ is in the β orientation, C1 is not hydroxyl, C5–C6 double bond is cis, C7–C8 double bond is trans, $R_1$ is methyl, C14 hydrogen is in the α orientation, C16–C17 is a single bond, then $R_2$ is a substituent I-7 or I-8; and when C3 is in the β orientation, C1 is in the α orientation, C5–C6 double bond is cis, C7–C8 double bond is trans, $R_1$ is $CH_3$, $C_{14}$ hydrogen is in the α-orientation, C16–C17 is a single bond, then $R_2$ is a modified version of side chain I-6 wherein the C22 methylene ($CH_2$) is replaced by a carbon-carbon triple bond.

The substituents I-1–I-10 are the same as substituents II-1–II-10, III-1–III-10, IV-1–IV-10 and V-1–V-10. The designation I, II, III, IV and V show the group of the compounds having the general formula I, II, III, IV or V to which the substituent selected form the substituents 1–10 is attached as $R_1$, $R_2$ or $R_3$.

Compounds of the general formula I are prepared according to the Reaction Scheme 1.

Scheme 1

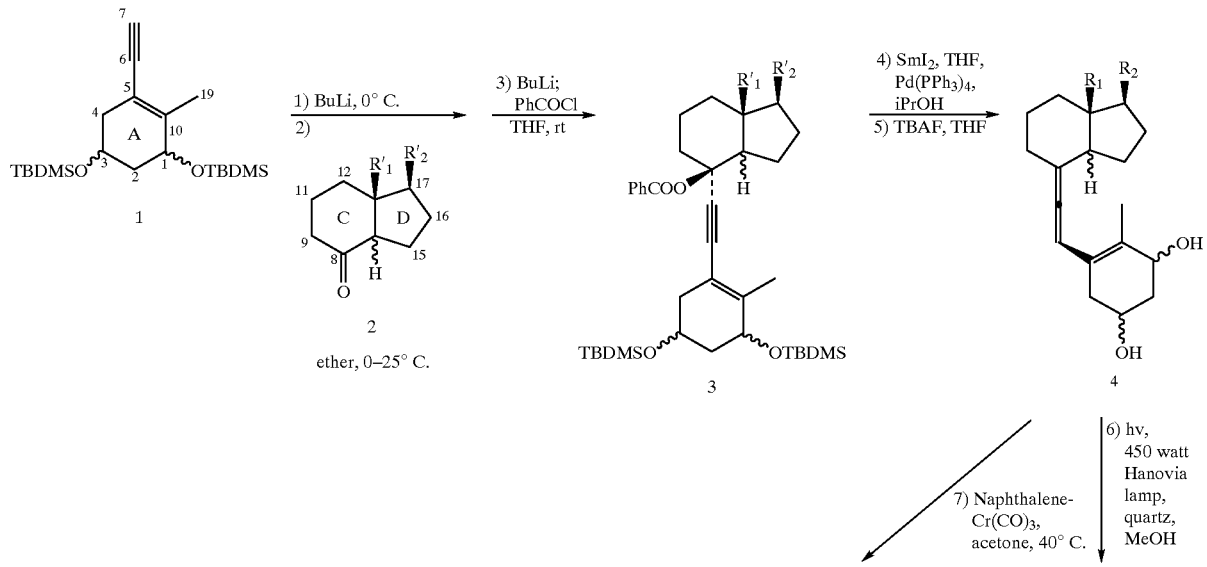

-continued
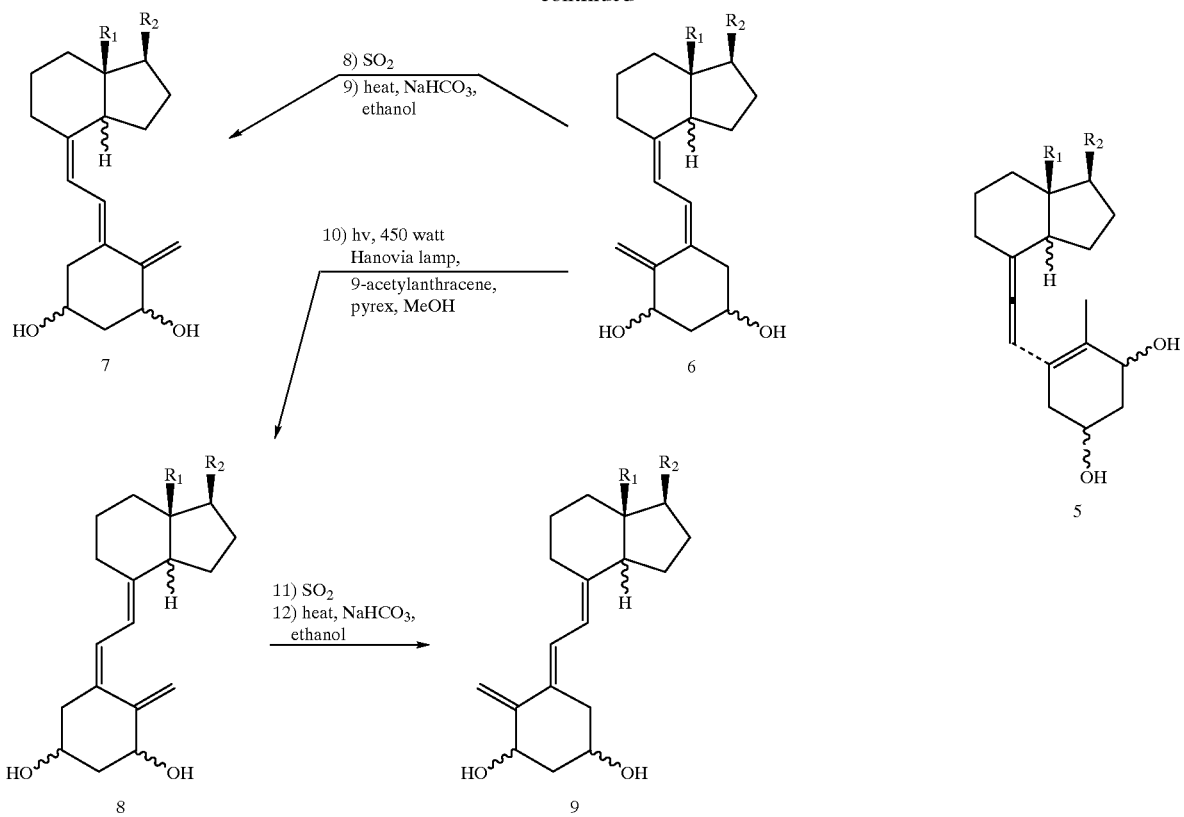
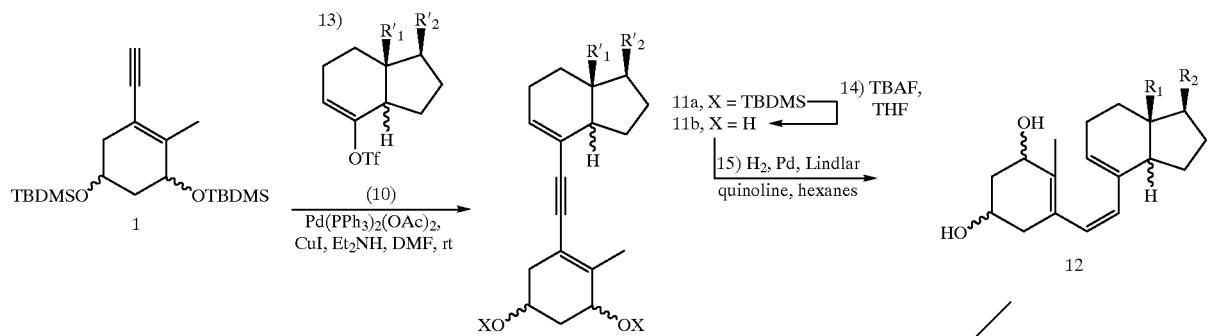
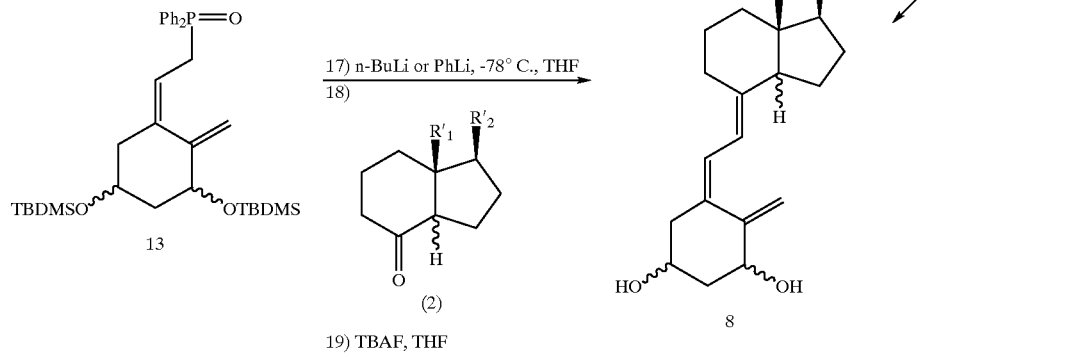

$R_1$ & $R_2$ refer to the substituents of general formula (I) or their suitably protected forms ($R'_1$ & $R'_2$), usually as their silyl ethers; all structures may have single or double bonds across the C16–C17 positions.

Reaction Scheme 1 illustrates preparation of compounds of the Group I. Compounds of the general formula I are chemically synthesized according to Scheme 1 using the three general approaches shown in Scheme 1-A, Scheme 1-B and Scheme 1-C. The starting A-ring fragments 1 and 13, wherein the $C_1$–C3 alcohols are masked as their TBDMS ether protecting groups (chemical acronyms throughout this patent document follow the guidelines of the "Notice to Authors" of the Journal of Organic Chemistry), as well as the CD fragments 2 and 10, wherein the substituents $R'_1$ and $R'_2$ are the alcohol protected forms of $R_1$ and $R_2$ given in general formula I, are prepared as recently reviewed (Zhu, G. D.; Okamura, W. H. *Chemical Reviews* 1995, 95, 1877–1952. Synthesis of Vitamin D (Calciferol); and see also Fernandez, S.; Ferrero, M.; Gotor, V.; Okamura, W. H. *J. Orga Chem.* 1995, 60, 6057–6061. Selective Acylation of A-Ring Precursors of Vitamin D Using Enzymes in Organic Solvents; Muralidharan, K. R.; de Lera, A. R.; Isaeff, S. D.; Norman, A. W.; Okamura, W. H. *J. Org. Chem.* 1993, 5, 1895–1899. Studies on the A-Ring Diastereomers of 1α,25-Dihydroxyvitamin $D_3$; Okamura, W. H.; Aurrecoechea, J. M.; Gibbs, R. A.; Norman, A. W. *J. Org. Chem.* 1989, 54, 4072–4083. Synthesis and Biological Activity of 9,11-Dihydrovitamin $D_3$ Analogues: Stereoselective Preparation of 6β-Vitamin D Vinylallenes and a Concise Enynol Synthesis for Preparing the A-Ring). In Scheme 1 general, structures 6, 7, 8, and 9, with or without a double bond across C16–C17, are collectively represented by generic structure I.

In Scheme 1-A, the vitamin D A-ring fragment 1 is treated in step 1 with butyllithium and then the resulting lithium salt is added to ketone 2 in step 2. The product from step 2 is reacted in step 3 with butyllithium and then benzoyl chloride to afford the propargyl benzoate 3. Reduction of 3 with samarium iodide with appropriate additives as in step 4 followed by deprotection with tetrabutylammonium fluoride (TBAF) in step 5 affords the 6β-vinylallene analog 4. Photochemical irradiation as in step 6 affords the corresponding 6α-vinylallene analog 5. Chromium(0) mediated isomerization of 4 in step 7 leads stereoselectively to the C5–C6 cis,C7–C8 cis analog 6, which upon photochemical irradiation using a medium pressure mercury lamp with triplet sensitizer in step 10 affords the C5–C6 cis, C7–C8 trans derivative 8. The vitamin D compounds 6 and 8 are converted by the same two step procedure (steps 8–9 or steps 11–12, respectively), to the corresponding C5–C6 trans compounds 7 and 9, respectively. Additional details for a specific case of the pathway of Scheme 1-A can be found in the literature (VanAlstyne, E. M.; Norman, A. W.; Okamura, W. H. *J. Am. Chem. Soc* 1994, 116, 6207–6216. 7,8-Cis Geometric Isomers of the Steroid Hormone, 1α,25-Dihydroxyvitamin $D_3$).

In Scheme 1-B, an alternative route to 8, and hence also 9 as in Scheme 1-A, starts with the palladium(0) mediated coupling of 1 with 10 in step 13 to afford 11a. Deprotection of the latter in step 14 to 11b followed by Lindlar semi-hydrogenation (step 15) of the latter (11b) affords the previtamin type compound 12. Heating previtamin 12 at ~100° C. (refluxing isooctane) in step 16 affords the desired 8.

In yet a third alternative Scheme I-C, the A-ring phosphine oxide 13, after deprotonation in step 17, is coupled with CD ring fragment 2 in step 18 (a so-called Horner-Wittig reaction). After deprotection in step 19, the resulting product is 8.

TABLE 1

Table 1 lists subgroups of analogs falling within the scope of the Group I.

| Formula | $C_1$–C3 | C5–C6 | C7–C8 | C14 | C16–C17 | R1 | R2 Substituents |
|---|---|---|---|---|---|---|---|
| I/1 | α-α, β-β α-β, β-α | cis or trans | cis or trans | α or β double | single $CH_2OH$ | $CH_3$ or proviso | all with |
| I/2 | β | cis | trans | α | single | $CH_3$ | all |
| I/3 | β | cis | trans | α | single | $CH_3$ | I-2, 9, 10 |
| I/4 | β | cis | trans | α | single | $CH_3$ | analog HL |
| I/5 | α-062 | cis | trans | α | single | $CH_2OH$ | all |
| I/6 | α-β | cis | trans | α | single | $CH_2OH$ | I-2, 3, 9, 10 |
| I/7 | β | cis | trans | α | single | $CH_2OH$ | all |
| I/8 | β H | cis | trans | α | single | $CH_2O$ | I-2, 3, 9, 10 |
| I/9 | α-β | cis | trans | β | single | $CH_3$ or $CH_2OH$ | all |
| I/10 | α-β | cis | trans | β | single | $CH_3$ or $CH_2OH$ | I-, 2, 3, 4, 9, 10 |
| I/11 | β | cis | trans | β | single | $CH_3$ or $CH_2OH$ | all |
| I/12 | β | cis | trans | β | single | $CH_3$ or $CH_2OH$ | I-, 3, 4, 9, 10 |
| I/13 | β | cis | trans | α | double | $CH_3$ | all |
| I/14 | α-β | cis | trans | α | single | $CH_2OH$ | all |
| I/15 | β | cis | trans | α | single | $CH_2OH$ | all |
| I/16 | α-β | cis | trans | β | single | $CH_3$ or $CH_2OH$ | all |
| I/17 | β | cis | trans | β | single | $CH_3$ or $CH_2OH$ | all |
| I/18 | β-α | cis | trans | α | single | $CH_3$ | analog HH |
| I/19 | α-β | cis | trans | α | single | $CH_3$ | analog HJ |

TABLE 1-continued

Table 1 lists subgroups of analogs falling within the scope of the Group I.

| Formula | C1–C3 | C5–C6 | C7–C8 | C14 | C16–C17 | R1 | R2 Substituents |
|---|---|---|---|---|---|---|---|
| I/20 | α-β | cis | trans | α | single | CH$_2$CH | analog HS |
| I/21 | α-β | cis | trans | β | single | CH$_3$ | analog GE |
| I/22 | α-β | cis | trans | α | single | CH$_3$ | analog DE |
| I/23 | α-β | cis | trans | α | single | CH$_3$ | analog DE |
| I/24 | α-β | cis | trans | α | single | CH$_3$ | analog HQ |
| I/25 | α-β | cis | trans | α | single | CH$_3$ | analog HR |
| I/26 | α-β | cis | trans | α | single | CH$_3$ | analog EV |
| I/27 | α-β | cis or trans | cis | α | single or double | CH$_3$ | all |
| I/28 | α-β | cis or trans | cis | α | single or double | CH$_3$ | I-1 |
| I/29 | α-β | trans | cis | α | single | CH$_3$ | analog JS |
| I/30 | α-β | cis | cis | α | single | CH$_3$ | analog JR |
| I/80 | deoxy-β | cis | trans | α | single | CH$_3$ | analog JX |
| I/81 | deoxy-β | cis | trans | α | single | CH$_3$ | analog JY |
| I/84 | α-β | cis | trans | α | single | CH$_3$ | analog IB |

The analogs listed in Group I are represented by the analogs identified as HL, HH, HJ, HS, GE, DE, DF, HQ, HR, EV, JR, JS, JY, JX, LO and IB. The synthesis of these analogs is described in the Example 1 (DE), Example 2 (DF), Example 3 (EV), Example 4 (GE), Example 6 (HH), Example 7 (HJ) Example 8 (HL), Example 9 (HQ), Example 10 (HR), Example 11 (HS), Example 12 (IB), Example 17 (JR), Example 18 (JS), Example 19 (JV), Example 20 (TW), Example 21 (JX), and Example 22 (JY). These analogs, depending on their structure, have a biological activity as agonists or antagonists of slow genomic responses and the rapid nongenomic responses.

The antagonists of the Group I are represented by the generic formula I wherein $R_1$ is methyl, C1 hydroxyl is in β configuration, C3 hydroxyl is in f configuration, C14 hydrogen is in α configuration and $R_2$ is the substituent 2, 9, 10. The representative analog is the analog HL.

The agonists of Group I are represented by a general formula I wherein $R_1$ is CH$_2$OH, C1 hydroxyl is in α configuration, C3 hydroxyl is in 5 configuration, C14 hydrogen is in α configuration and $R_2$ are the substituents I-1–I-10, preferably substituents I-2, I-3, I-4, I-9 and I-10.

In the same group, the antagonist are compounds wherein $R_1$ is CH$_2$OH, C1 hydroxyl is in β configuration, C3 hydroxyl is in β configuration, C14 hydrogen is in α configuration and $R_2$ are the substituents I-1–I-10, preferably substituents I-2, I-3, I-9 and I-10.

The group of agonists is represented by a general formula I wherein $R_1$ is CH$_3$ or CH$_2$OH, C1 hydroxyl is in α configuration, C3 hydroxyl is in β configuration, C14 hydrogen is in β configuration and $R_2$ are the substituents I-1–I-10, preferably substituents I-1, I-2, I-3, I-4, I-9 and I-10.

The group of antagonists is represented by a general formula I wherein $R_1$ is CH$_3$ or CH$_2$OH, C1 hydroxyl is in β configuration, C3 hydroxyl is in β configuration, C14 hydrogen is in β configuration and $R_2$ are the substituents I-1–I-10, preferably substituents I-1, I-2, I-3, I-4, I-9 and I-10.

The group II is represented by compounds having a general formula II

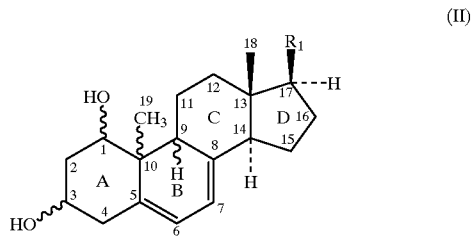

(II)

wherein C1 and C3 are positional isomers α and β which may be the same or different in α-α, β-β, α-β or β-α configuration;

wherein C9 hydrogen and C10 methyl are positional isomers α and β which may be the same or different in α-α, β-β, α-β or β-α configuration;

wherein C16–C17 is a single or double bond;

wherein $R_1$ is a substituent selected from the group consisting of substituents II-1 through II-10

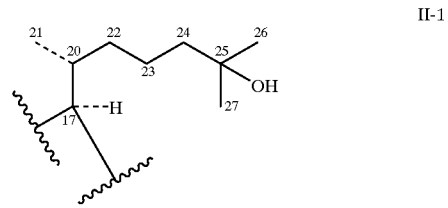

II-1

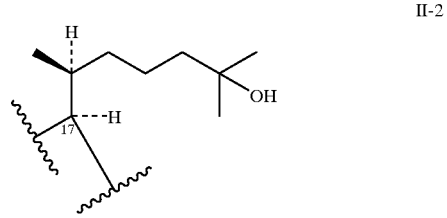

II-2

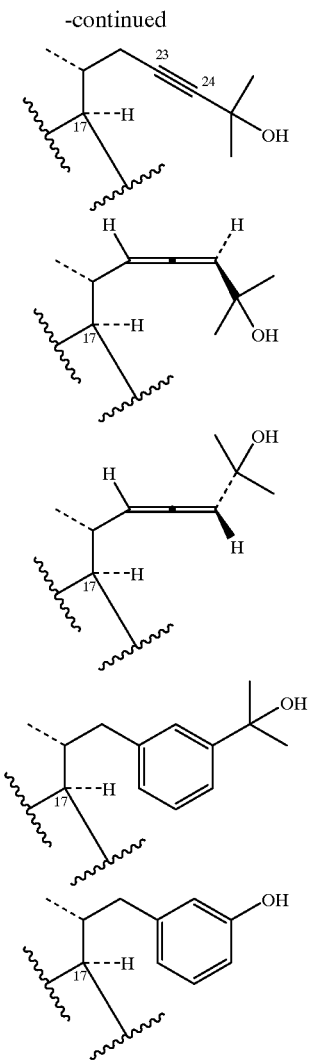
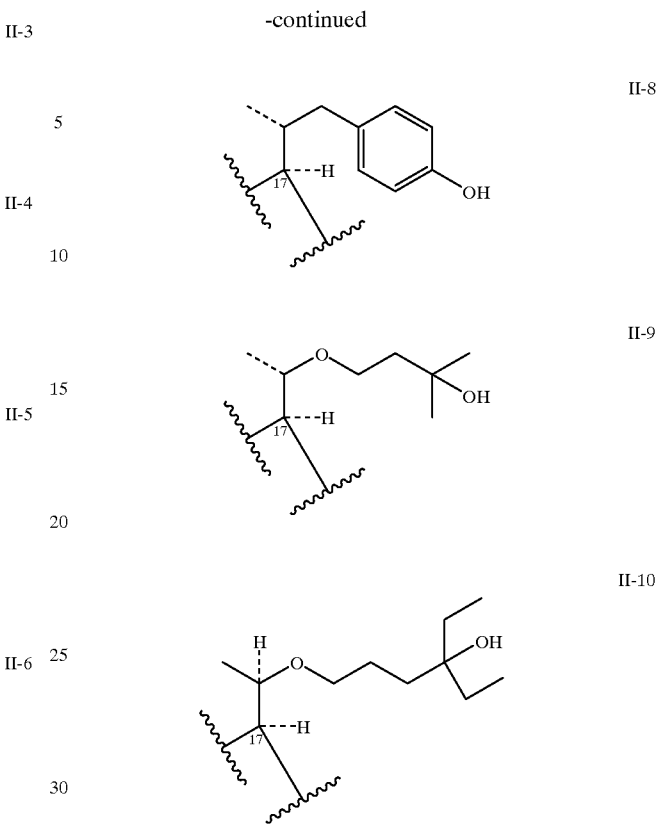
with the proviso that when $C_1$ and $C_3$ are α-β, $C_9$ and $C_{10}$ are α-α, β-β, α-β and β-α, and C16–C17 is a single bond, then $R_1$ is not the substituent II-1.
Compounds of the general formula II are prepared according to the Reaction Scheme 2.
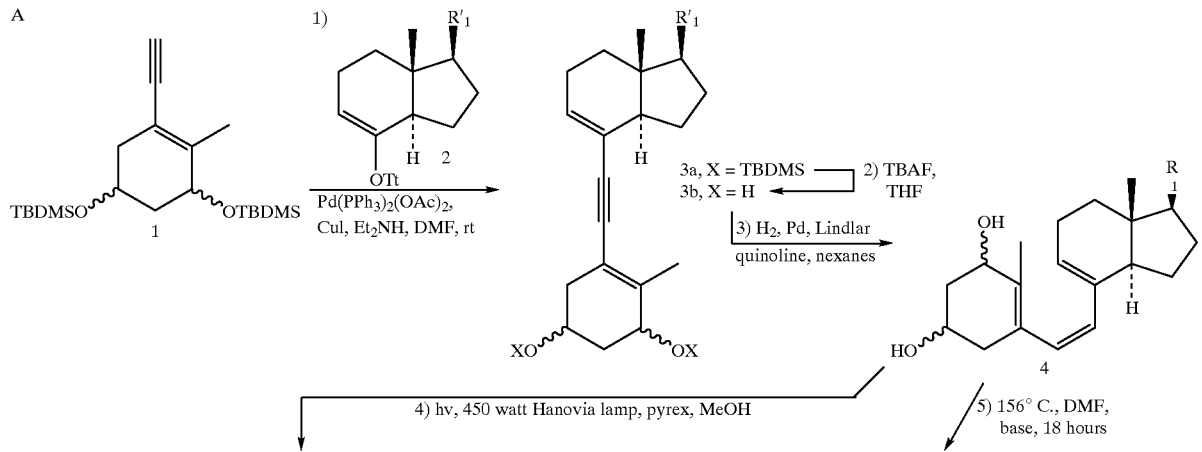

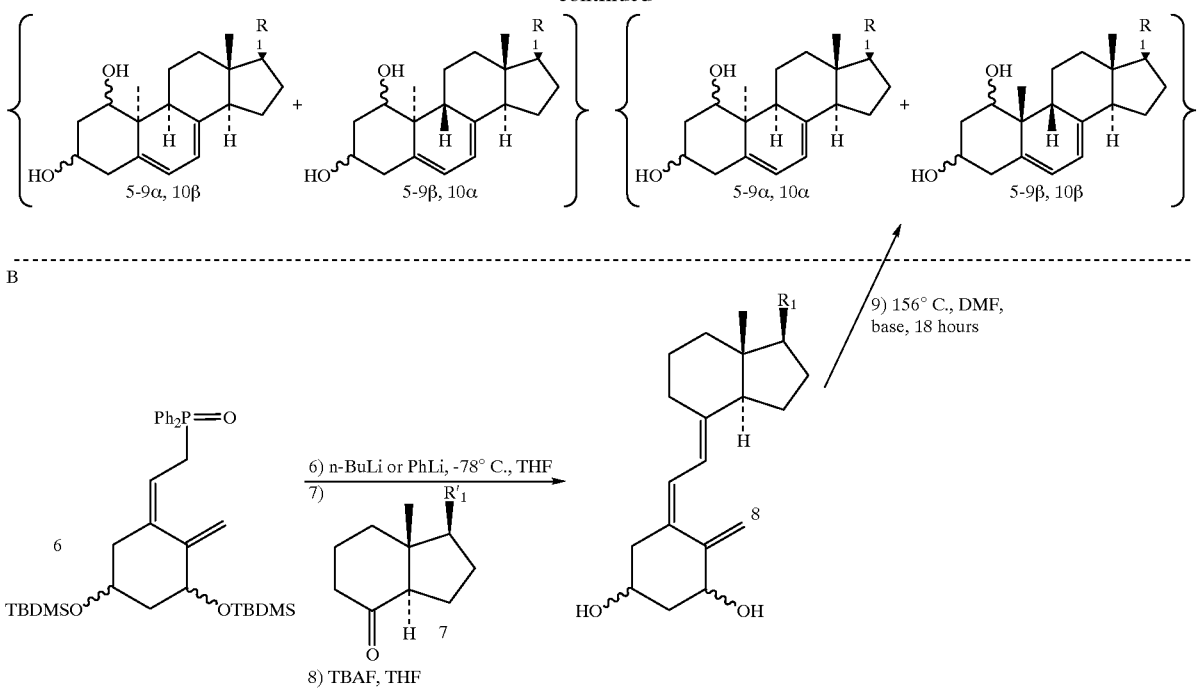

$R_1$ refers to the substituents of generic formula (II) or the suitably protected forms ($R'_1$), usually as the silyl ether; all structures may have single or double bonds across the C16–17 positions.

Reaction Scheme 2 illustrates preparation of compounds of the Group II.

Compounds of the general formula II are prepared according to Scheme 2 using the two general approaches shown as Scheme 2-A and Scheme 2-B. The starting A-ring fragments 1 and 6, wherein the C1–C3 alcohols are masked as their TBDMS ether protecting groups (chemical acronyms throughout this patent document follow the guidelines of the "Notice to Authors" of the Journal of Organic Chemistry), as well as the CD fragments 2 and 7, wherein the substituent R'1 is the alcohol protected form of $R_1$ given in general formula II, are easily prepared as recently reviewed (Zhu, G. -D.; Okamura, W. H. Chemical Reviews 1995, 9, 1877–1952. Synthesis of Vitamin D (Calciferol); and see also Fernández, S.; Ferrero, M.; Gotor, V.; Okamura, W. H. J. Org. Chem, 1995, 60, 6057–6061. Selective Acylation of A-Ring Precursors of Vitamin D Using Enzymes in Organic Solvents; Muralidharan, K. R.; de Lera, A. R.; Isaeff, S. D.; Norman, A. W.; Okamura, W. H. J. Org. Chem. 1993, 58, 1895–1899. Studies on the A-Ring Diastereomers of 1α,25-Dihydroxyvitamin D3; Okamura, W. H.; Aurrecoechea, J. M.; Gibbs, R. A.; Norman, A. W. J. Org. Chem. 1989, 54, 4072–4083. Synthesis and Biological Activity of 9,11-Dihydrovitamin $D_3$ Analogues: Stereoselective Preparation of 6β-Vitamin D Vinylallenes and a Concise Enynol Synthesis for Preparing the A-Ring). As also indicated in Scheme 2, each compound may have a single or double bond across C16–C17. In addition, the four general structures of 5 shown in Scheme 22 may be collectively represented by generic structure II.

Scheme 2-A starts with the palladium(0) mediated coupling of 1 with 2 in step 1 to afford 3a. Deprotection of the latter in step 2 using TBAF and THF gives 3b, which is followed by Lindlar semi-hydrogenation (step 3) affords the previtamin type compound 4. Heating previtamin 4 in step 5 at elevated temperatures as indicated affords the αα and ββ isomers known as the pyrocalciferol and isopyrocalciferol types of vitamin D provitamins 5. By contrast, as shown in step 4, photochemical irradiation through pyrex using a medium pressure mercury lamp affords the 9α,10β, and the 9β,10α provitamin D type isomers known as the dehydrocholesterol and the lumisterol analogs 5.

In a second alternative to Scheme 2-A, the A-ring phosphine oxide 6, after deprotonation in step 6, is coupled with CD ring fragment 7 in step 7, a so-called Horner-Wittig reaction. After deprotection in step 8, the resulting product is 8 which, as described earlier, can be heated in step 9 at elevated temperatures to the same 9α,10α and 9β,10β provitamin D diastereomers 5, respectively.

Table 2 lists subgroups of analogs falling within the scope of the Group II.

TABLE 2

| Formula | C1-C3 | C9H-C10CH3 | C16-C17 | $R_1$ Substituents |
|---|---|---|---|---|
| I/31 | α-α, β-β | αα, αβ, | single double | all |
| II/32 | β α-β, β-α | β-αβ ββ, βα | single double | all |
| II/33 | β-β | β-α | single double | II-1, 2, 4, 10 |
| II/34 | β-β | α-β | single double | all |
| II/35 | β-β | α-β | single double | II-1, 2, 4, 10 |
| II/36 | α-β | α-α | single double | all |
| II/37 | α-β | α-α | single double | II-1, 2, 4, 10 |
| II/38 | α-β | α-α | single | analog JO Check (II-I) |
| II/39 | α-β | β-α | single double | all |
| II/40 | α-β | β-α | single | II-1, 2, 4, 10 |
| II/41 | α-β | β-α | single | analog JN (II-1) |
| II/42 | α-β | β-β | single double | all |

TABLE 2-continued

| Formula | C1-C3 | C9H-C10CH3 | C16-C17 | R₁ Substituents |
|---|---|---|---|---|
| II/43 | α-β | β-β | single double | II-1, 2, 4, 10 |
| II/44 | α-β | β-β | single | analog JP (II-1) |
| II/45 | α-β | β-α | single double | all |
| II/46 | α-β | β-α | single double | II-1, 2, 4, 10 |
| II/47 | α-β | β-α | single | analog JM (II-1) |
| II/48 | α-α | β-α | single double | II-1, 2, 4, 10 |
| II/49 | α-α | α-β | single double | II-1, 2, 4, 10 |
| II/50 | β-α | β-α | single double | II-1, 2, 4, 10 |

The analogs listed in Group II are represented by the analogs identified as JM, JN, JO and JP. These analogs, depending on their structure, have a biological activity as agonists or antagonists of slow genomic responses or the rapid nongenomic responses.

In Group II, the antagonists are represented by the generic formula II wherein C1 hydroxyl is in β configuration, C3 hydroxyl is in β configuration, C9 hydrogen is in β and C10 methyl is in α configuration and R₁ is the substituent II-1, II-2, II-4 and II-10, preferably the substituents II-1, II-2, and II-10, or wherein C1 hydrogen is in β and C3 is in β configuration, C9 hydrogen is in a and C10 methyl is in β configuration and R₁ is the substituent II-1, II-2, II-7, II-10, and is preferably the substituent II-1, II-2 or II-10.

In Group II, the agonists are represented by the generic formula II wherein C1 hydroxyl is in α configuration, C3 hydroxyl is in β configuration, C9 hydrogen is in α and C10 methyl is in α configuration and R₁ is the substituent II-1, II-2, II-4, II-10, and preferably it is the substituent II-1, II-2, and II-13. The specific agonist of this group is the analog JO where R₁ is the substituent II-1. Preparation of the analog JO is described in Example 6.

The other agonists of the Group II are represented by the general formula II wherein C1 hydroxyl is in α and C3 hydroxyl is in β configuration, C9 hydrogen is in β and C10 methyl is in α configuration and R₁ is the substituent II-1, II-2, II-4, II-10 and , preferably, it is the substituent II-1, II-2 and II-10. The specific agonist of this group is the analog JN where R₁ is the substituent II-1. Preparation of the analog JN is described in Example 5.

The other agonists of the Group II are represented by the general formula II wherein C1 hydroxyl is in α and C3 hydroxyl is in β configuration, C9 hydrogen is in β and C10, methyl is in α configuration and R₁ is the substituent II-1–II-10, preferably the substituent II-1, II-2, II-4 and II-10. The specific agonist of this group is the analog JM where R₁ is the substituent II-1. Preparation of the analog JM is described in Example 5.

Still another agonists of the Group II are represented by the general formula II wherein C1 hydroxyl is in α and C3 hydroxyl is in β configuration, C9 hydrogen is in β and C10 methyl is in β configuration and R₁ is the substituent II-1–II-10, preferably II-1, II-2, II-4 and II-10. The specific agonist of this group is the analog JP where R₁ is the substituent II-1. Preparation of the analog JP is described in Example 6.

The group III is represented by compounds having a general formula III

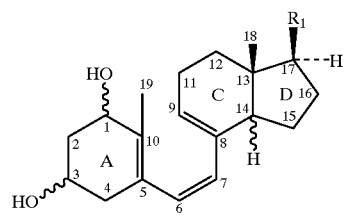

(III)

wherein C1 and C3 are positional isomers α and β which may be the same or different in α-α, β-β, α-β or β-α configuration;

wherein C14 hydrogen is α or β;

wherein C16–C17 is a single or double bond;

wherein R₁ is a substituent selected from the group consisting of substituents III-1 through III-10

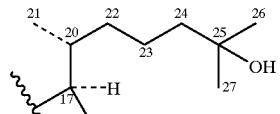

III-1

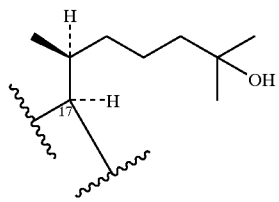

III-2

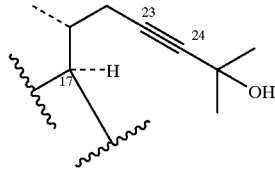

III-3

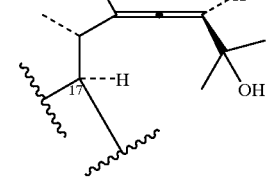

III-4

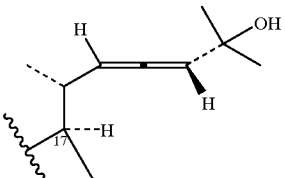

III-5

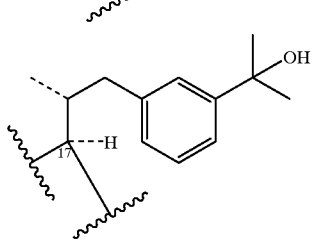

III-6

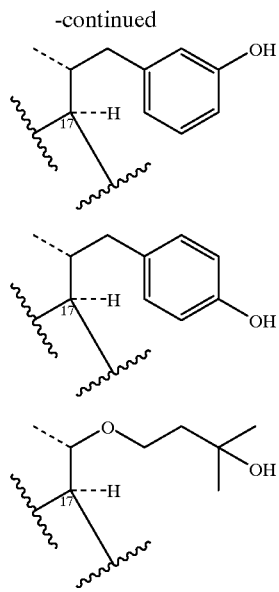
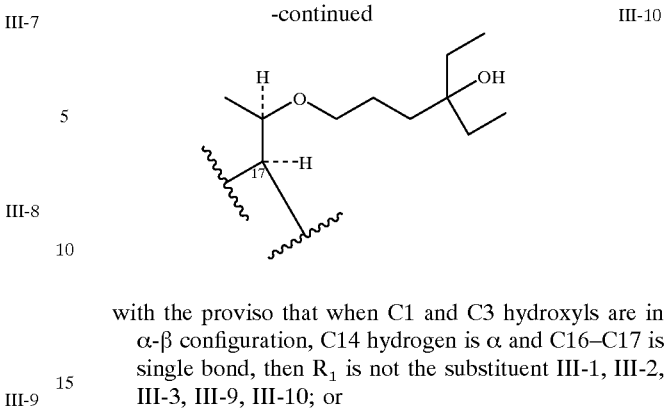
with the proviso that when C1 and C3 hydroxyls are in α-β configuration, C14 hydrogen is α and C16–C17 is single bond, then $R_1$ is not the substituent III-1, III-2, III-3, III-9, III-10; or
when C1 and C3 hydroxyls are α-β and C14 hydrogen is α and C16–C17 is a single or double bond, then $R_1$ is not the substituent III-4 and III-5.
Compounds of the general formula III are prepared according to the Reaction Scheme 3.
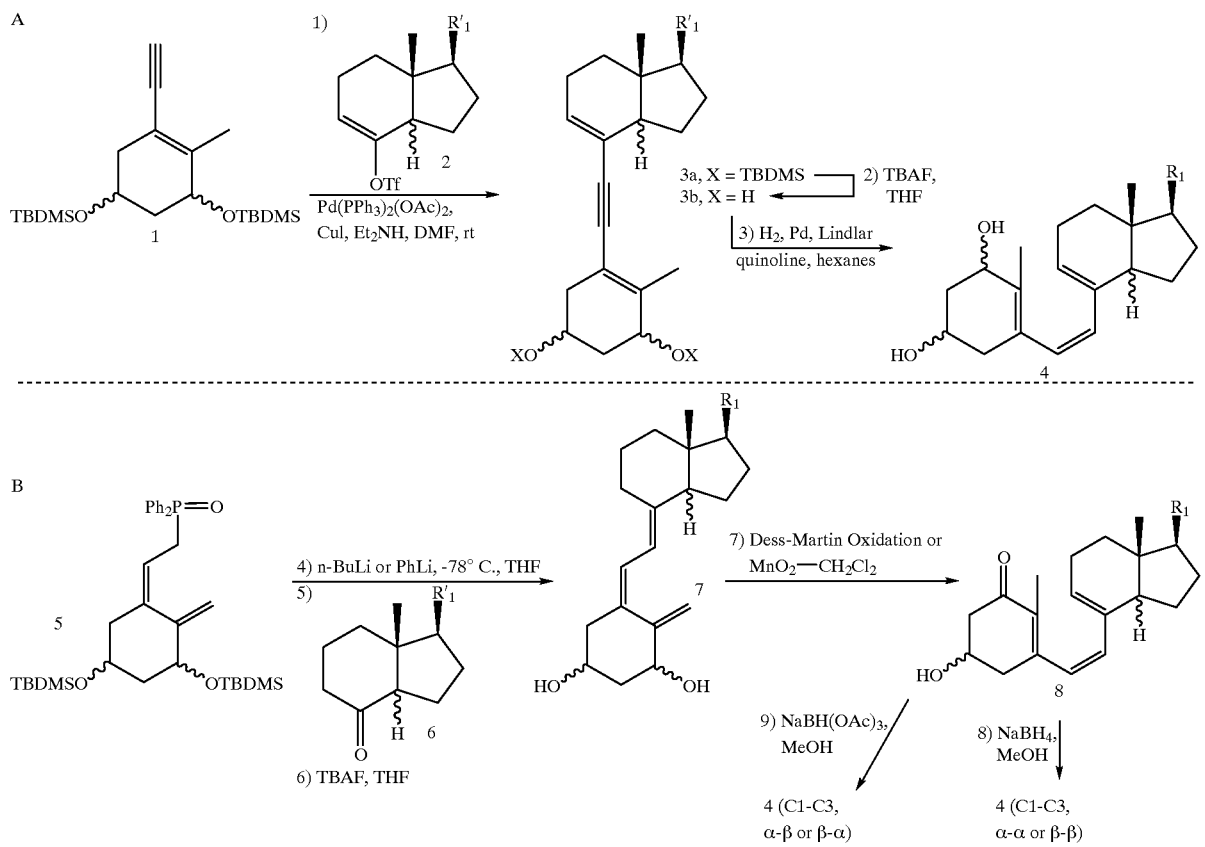

$R_1$ refers to the substituents of generic formula (III) or the suitably protected forms ($R'_1$), usually as the silyl ether; all structures may have single or double bonds across the C16–17 positions.

Reaction Scheme 3 illustrates preparation of compounds of the Group III.

Compounds of the general formula III are prepared according to Scheme 3 using the two general approaches shown as Scheme 3-A and Scheme 3-B. The starting A-ring fragments 1 and 5, wherein the C1–C3 alcohols are masked as their TBDMS ether protecting groups (chemical acronyms throughout this patent document follow the guidelines of the "Notice to Authors" of the Journal of Organic Chemistry), as well as the CD fragments 2 and 6, wherein the substituent $R'_1$ is the alcohol protected form of $R_1$ given in general formula II, are easily prepared according to Zhu, G. -D.; Okamura, W. H. *Chemical Reviews* 95: 1877–1952 (1995). Synthesis of Vitamin D (Calciferol); Fernández, S.; Ferrero, M.; Gotor, V.; Okamura, W. H. *J. Org. Chem.* 60: 6057–6061 (1995). Selective Acylation of A-Ring Precursors of Vitamin D Using Enzymes in Organic Solvents; Muralidharan, K. R.; de Lera, A. R.; Isaeff, S. D.; Norman, A. W.; Okamura, W. H. *J. Org. Chem.* 58: 1895–1899 (1993). Studies on the A-Ring Diastereomers of 1α,25-Dihydroxyvitamin $D_3$; Okamura, W. H.; Aurrecoechea, J. M.; Gibbs, R. A.; Norman, A. W. *J. Org. Chem,* 54: 4072–4083 (1989). Synthesis and Biological Activity of 9,11-Dihydrovitamin $D_3$ Analogues: Stereoselective Preparation of 6β-Vitamin D Vinylallenes and a Concise Enynol Synthesis for Preparing the A-Ring. As indicated above for Scheme 3, each compound may have a single or double bond across C16–C17. Thus, compound 4 is the same as the compound having general formula III.

Reactions illustrated in Scheme 3-A begins with the palladium(0) mediated coupling of 1 with 2 in step 1 to afford compound 3a. Deprotection of 3a in step 2 to gives compound 3b followed by Lindlar semi-hydrogenation (step 3) of the latter (3b) affords the desired previtamin type compound 4. In a second route, shown as scheme 3B, the A-ring phosphine oxide 5, after deprotonation in step 4, is coupled with CD ring fragment 6 in step 5 followed by deprotection in step 6 with TBAF and THF. The latter affords 7, which on selective allylic oxidation using either the Dess-Martin periodinane oxidation method or the more classical manganese dioxide in dichloromethane affords the previtamin ketone type 8 shown in Scheme 3B. On the one hand, normal sodium borohydride reduction in methanol affords the previtamin type alcohol 4 wherein the two A-ring hydroxyls at C1 and C3 are both cis to each other, either α-α or β-β. In contrast, reduction of the same ketone 8 using sodium triacetoxyborohydride in methanol as shown in step 9, affords the alcohol 4 but stereoselectively in such a manner that the two hydroxyls at C1 and C3 are trans to one another, i.e. C1–C3 being α-β or β-α. Muralidharan, K. R.; de Lera, A. R.; Isaeff, S. D.; Norman, A. W.; Okamura, W. H. *J. Org. Chem,* 58: 1895–1899 (1993). Studies on the A-Ring Diastereomers of 1α,25-Dihydroxyvitamin $D_3$).

Table 3 lists subgroups of analogs falling within the scope of the Group III.

TABLE 3

| Formula | C1-C5 | C14 | C16-C17 | $R_1$ Substituents |
|---|---|---|---|---|
| III/51 | αα, αβ, βα, ββ | β or β | single double | all |
| III/52 | β | α | single double | all |
| III/53 | β | α | single double | III-1, 2, 4, 7, 9, 10 |

TABLE 3-continued

| Formula | C1-C5 | C14 | C16-C17 | $R_1$ Substituents |
|---|---|---|---|---|
| III/54 | β | α | single double | all |
| III/55 | β | α | single double | III-1, 2, 4, 7, 9, 10 |
| III/56 | β | β | single double | all |
| III/57 | β | β | single double | III-1, 2, 4, 7, 9, 10 |
| III/58 | β | β | single double | all |
| III/59 | β | β | single double | III-1, 2, 4, 7, 9, 10 |
| III/60 | β | β | single | analog GF (III-1) |

The analogs listed in Group III are represented by the analog identified as GF. These analogs of Group III, depending on their structure and configuration, have a biological activity as agonists or antagonists of slow genomic responses and agonists or antagonists of the rapid nongenomic responses.

In Group III, the agonists and antagonists are represented by the generic formula III wherein C1 hydroxyl is in α or β configuration, C3 hydroxyl is in β configuration, C14 hydrogen is in α or β configuration, C16–C17 is a single or double bond and $R_1$ is the substituent III-1–III-10.

Preferred group of compounds of the Group III are compounds wherein C1 is in α configuration, C3 is in β configuration and the $R_1$ substituent is selected from the group III-1–III-10.

The specific agonist of this group is the analog GF where $R_1$ is the substituent III-1. Preparation of the analog GF is described in Example 2.

The group IV is represented by compounds having a general formula IV

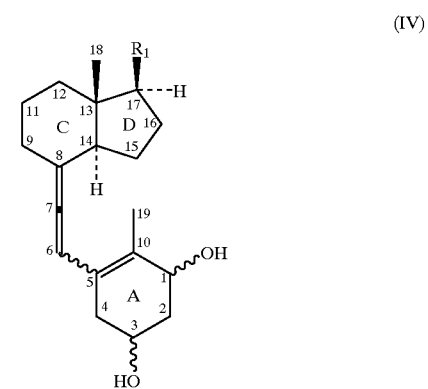

(IV)

wherein C1 and C3 hydroxyls are positional isomers α and β which may be the same or different in α-α, β-β, α-β or β-α configuration;

wherein the C5–C6 is in α or β configuration;

wherein C14 hydrogen is α;

wherein C16–C17 is a single or double bond;

wherein $R_1$ is a substituent selected from the group consisting of substituents IV-1 through IV-10

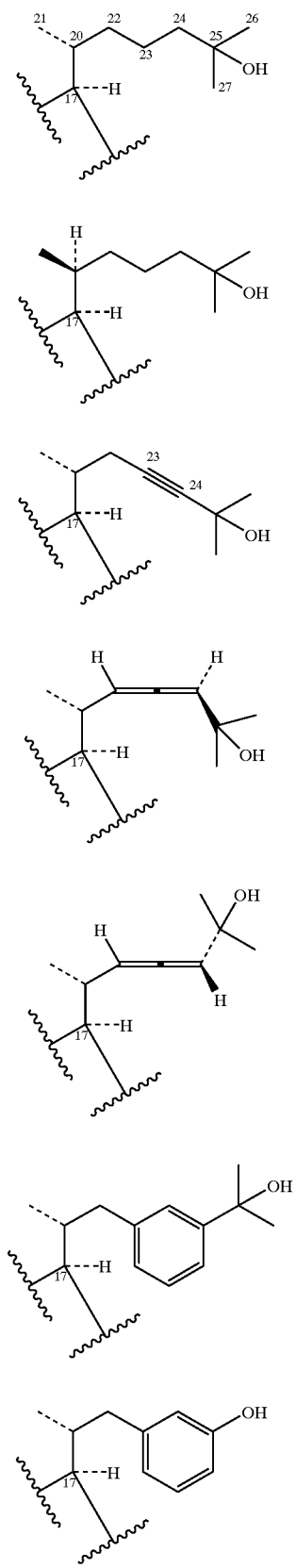
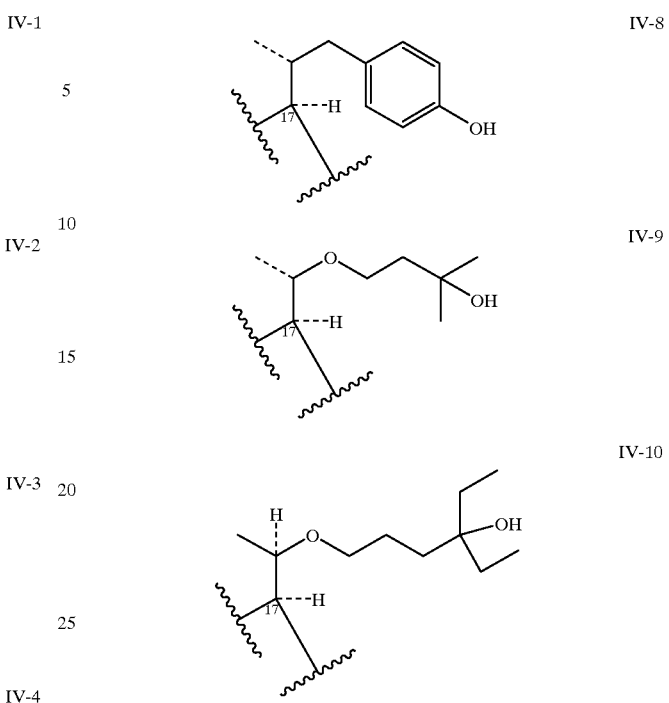
Compounds of the general formula IV are prepared according to the Reaction Scheme 4.
Scheme 4
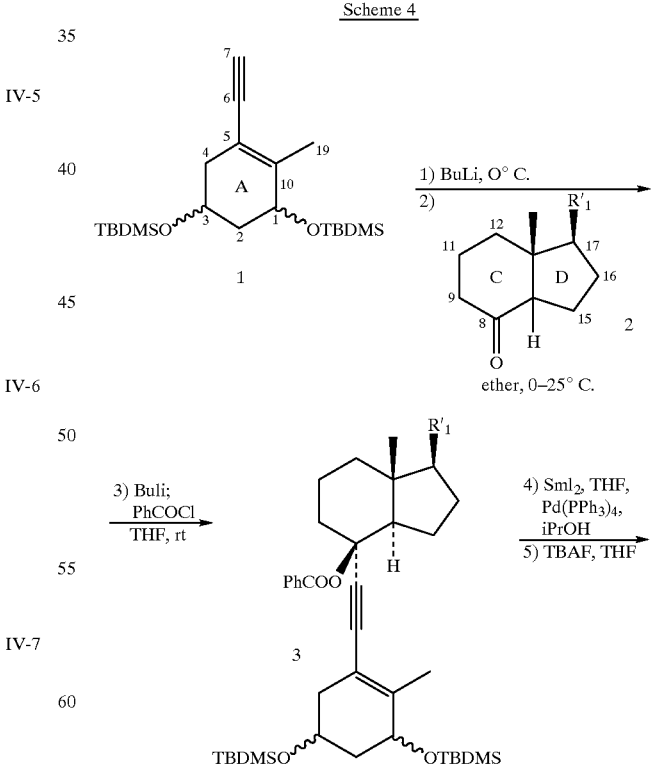

-continued (6β)

6) hv,
450 watt
Hanovia lamp,
quartz,
MeOH (6α)

$R_1$ refers to the substituents of generic formula (IV) or the suitably protected forms ($R'_1$), usually as the silyl ether; all structures may have single or double bonds across the C16–C17 positions.

$R_1$ refers to the substituents of generic formula (IV) or the suitably protected forms ($R'_1$), usually as the silyl ether; all structures may have single or double bonds across the C16–C17 positions.

Reaction Scheme 4 illustrates preparation of compounds of the Group IV. Compounds of the general formula IV are prepared according to the general reaction Scheme 4. The starting A-ring fragment 1, wherein the C1–C3 alcohols are masked as their TBDMS ether protecting groups (chemical acronyms throughout this patent document follow the guidelines of the "Notice to Authors" of the Journal of Organic Chemistry), as well as the CD fragment 2, wherein the substituent $R'_1$ is the alcohol protected form of $R_1$ given in general formula IV, are easily prepared as described in Zhu, G. D.; Okamura, W. H. *Chemical Reviews*, 95: 1877–1952 (1995). Synthesis of Vitamin D (Calciferol); Fernández, S.; Ferrero, M.; Gotor, V.; Okamura, W. H. *J. Org. Chem:*, 60: 6057–6061 (1995). Selective Acylation of A-Ring Precursors of Vitamin D Using Enzymes in Organic Solvents; Muralidharan, K. R.; de Lera, A. R.; Isaeff, S. D.; Norman, A. W.; Okamura, W. H. *J. Org. Chem:*, 58: 1895–1899 (1993). Studies on the A-Ring Diastereomers of 1α,25-Dihydroxyvitamin $D_3$; Okamura, W. H.; Aurrecoechea, J. M.; Gibbs, R. A.; Norman, A. W. *J. Org. Chem.* 54: 4072–4083 (1989). Synthesis and Biological Activity of 9,11-Dihydrovitamin $D_3$ Analogues: Stereoselective Preparation of 6β-Vitamin D Vinylallenes and a Concise Enynol Synthesis for Preparing the A-Ring). As indicated in Scheme 4, each compound may have a single or double bond across C16–C17.

In Scheme 4, the vitamin D A-ring fragment 1 is treated in step 1 with butyllithium and then the resulting lithium salt is added to ketone 2 in step 2 . The resulting product is directly reacted in step 3 with butyllithium and then benzoyl chloride to afford the propargyl benzoate 3. As similarly described in Scheme 1, reduction of 3 using samarium iodide, catalytic palladium(0) reagent, and isopropyl alcohol affords an intermediate allene in step 4 which is directly deprotected using TBAF and THF in step 5 to afford the 6β-vinylallene analog 4. Photochemical irradiation as in step 6 using a 450 watt medium pressure mercury lamp with methanol as solvent affords the corresponding 6α-diastereomer 5. The vinylallenes 4 and 5 are more generally represented by the generic structure IV.

Table 4 lists subgroups of analogs falling within the scope of the Group IV.

TABLE 4

| Formula | C1-C3 | C5-C6 | C16-C17 | $R_1$ |
|---|---|---|---|---|
| IV/61 | αα-ββ<br>αβ-ββ | α or β | single<br>double | all |
| IV/62 | α-α | α | single<br>double | all |
| IV/63 | α-α | α | single<br>double | IV-1, 2, 4, 7, 9, 10 |
| IV/64 | β-β | α | single<br>double | all |
| IV/65 | β-β | α | single<br>double | IV-1, 2, 4, 7, 9, 10 |
| IV/66 | α-β | α | single<br>double | all |
| IV/67 | α-β | α | single<br>double | IV-1, 2, 4, 7, 9, 10 |
| IV/68 | α-β | α | single | analog JW (IV-1) |
| IV/69 | β-α | α | single<br>double | all |
| IV/70 | β-β | α | single<br>double | IV-1, 2, 4, 7, 9, 10 |
| IV/71 | α-α | β | single<br>double | all |
| IV/72 | α-α | β | single<br>double | IV-1, 2, 4, 7, 9, 10 |
| IV/73 | β-β | β | single<br>double | all |
| IV/74 | β-β | β | single<br>double | IV-1, 2, 4, 7, 9, 10 |
| IV/75 | α-β | β | single<br>double | all |
| IV/76 | α-β | β | single<br>double | IV-1, 2, 4, 7, 9, 10 |
| IV/77 | α-β | β | single | analog JV (IV-1) |
| IV/78 | β-α | β | single<br>double | all |
| IV/79 | β-α | α | single<br>double | IV-1, 2, 4, 7, 9, 10 |

The analogs listed in Group IV are represented by the analogs identified as analogs JV and JW. These analogs, depending on their structure and configuration, have a biological activity as agonists of slow genomic responses or as agonists or antagonists of the rapid nongenomic responses.

In Group IV, the agonists and antagonists are represented by the generic formula IV wherein C1 hydrogen is in α or β configuration, and C3 is in α or β configuration, C5–C6 is in α or β configuration, C14 hydrogen is α, C16–C17 is a single or double bond and $R_1$ is a substituent selected from the group consisting of substituents IV-1 through IV-10.

Preferred agonists in this group of compounds of this group are compounds wherein C1 is in α configuration, C3 is in β configuration and the $R^1$ substituent is IV-1. The specific agonists of this group are the analogs JV and JW.

The compounds of Group V are represented by a general formula V

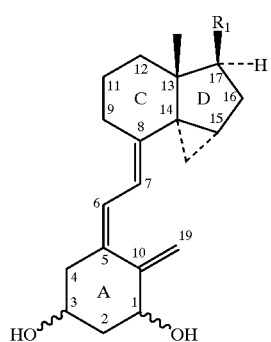

(V)

wherein C1 and C3 are positional isomers α and β which may be the same or different in αα, ββ, αβ or βα configuration, wherein C5–C6 double band is cis and C7C8 double band is trans;

wherein C16–C17 is a single or double bond; and wherein $R_1$ is a substituent is selected from the group consisting of substituents V-1 through V-10

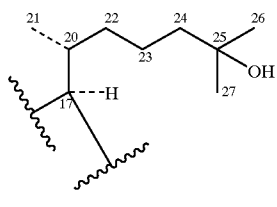

V-1

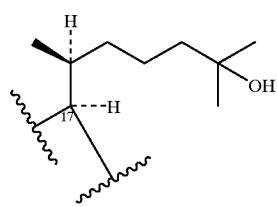

V-2

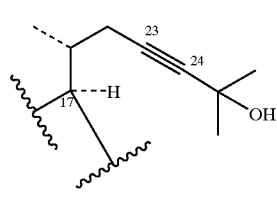

V-3

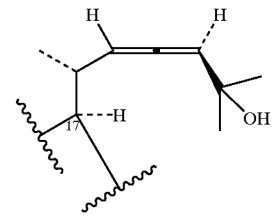

V-4

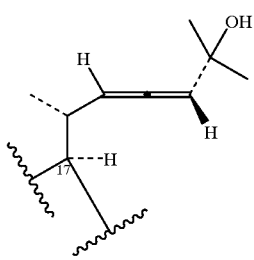

V-5

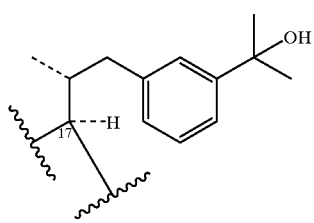

V-6

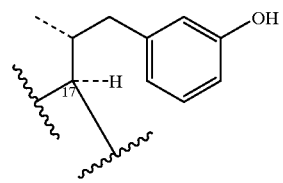

V-7

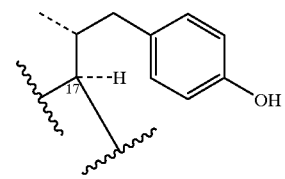

V-8

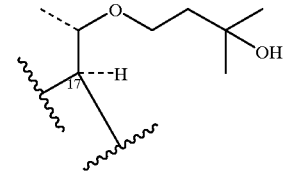

V-9

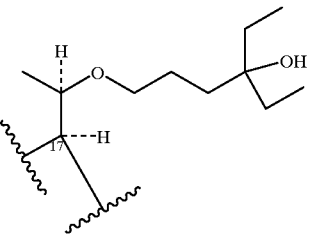

V-10

Compounds of the general formula V are prepared according to Reaction Scheme 5 using the two general approaches shown in Scheme 5-A and Scheme 5-B.

Scheme 5
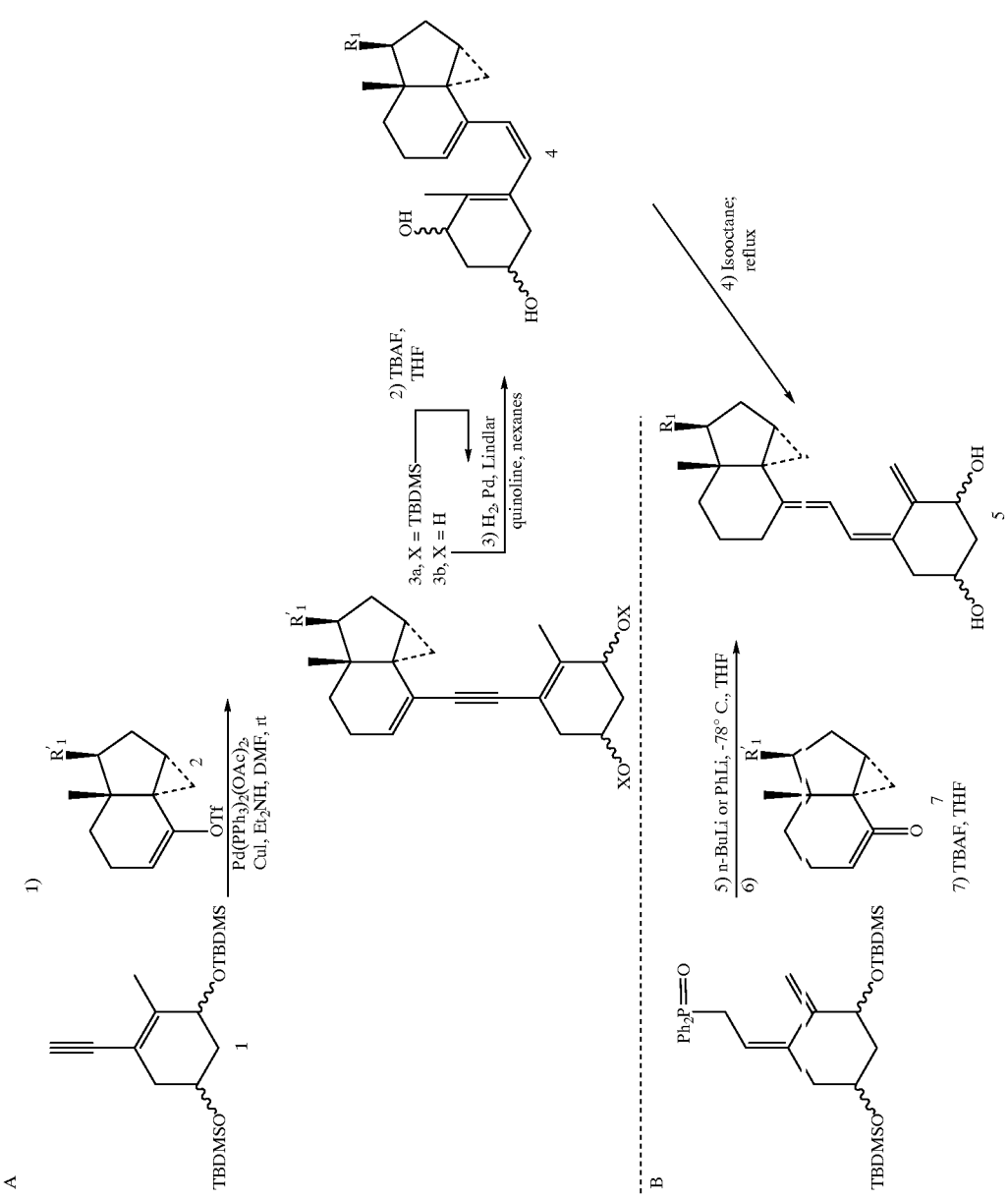

R$^1$ refers to the substituents of generic formula (V) or the suitably protected forms (R'$_1$), usually as the silyl ether. The starting A-ring fragments 1 and 6, wherein the C1–C3 alcohols are masked as their TBDMS ether protecting groups as well as the CD fragments 2 and 7, wherein the substituent R'$_1$ is the alcohol protected form of R$_1$ given in general formula V, are prepared according to *Chemical Reviews.* 95: 1877–1952 (1995). *J. Org. Chem.,* 58: 1895–1899 (1993); *J. Org. Chem.,* 54: 4072–4083 (1989) as cited above. Each compound may have a single or double bond across C16–C17. Thus, 5 is the same as generic structure V.

Scheme 5-A starts with the palladium(0) mediated coupling of 1 with 2 in step 1 to afford 3a, which in turn can be deprotected in step 2 using TBAF and THF to afford the free alcohol 3b. Lindlar catalyzed hydrogenation of 3b affords previtamin 4 which upon heating and refluxing isooctane as given in step 4 produces the desired analog 5. In an alternative scheme, namely Scheme 5-B, the A-ring phosphine oxide 6 is directly treated with strong base as shown in step 5 whereupon Horner-Wittig reaction with ketone 7 produces a protected triene as given in step 6. Deprotection of the resulting product with TBAF and tetrahydrofuran in step 7 of Scheme 5 also affords the same analog 5.

TABLE 5

| Formula | C1–C3 | R$_1$ |
|---|---|---|
| V/82 | αα-ββ | all |
|  | αβ-βα | all |
| V/ | α-α | all |
| V/ | α-β | all |
| V/83 | α-β | analog LO (V-1) |
| V | α-β | all |
| V | β-β | all |

A representative analog of this group is analog LO which is an agonist of slow genomic and rapid nongenomic responses.

II. Biological Activity of 1α,25(OH)$_2$D$_3$ Analogs

Analogs of the invention generate two types of biological responses. One type of the response are those generated via genomic pathways. The second type of responses are rapid responses. The analogs of the invention act as either agonists or antagonists of both slow and rapid biological responses. Some of the analogs act solely as agonists for one or the other type of biological responses. Some analogs act as agonist for both types of responses. Some other analogs, as described in detail herein, act as agonists on one type or biological responses and as antagonists of the other type of biological responses.

Both the slow and rapid biological responses are involved in a wide array of physiological functions.

The scope of the biological responses related to vitamin D and its analogs is best understood through the concept of the vitamin D endocrine system as illustrated in FIG. 1.

FIG. 1 summarizes the vitamin D endocrine system functions. In addition to production of 1α,25(OH)$_2$D$_3$ and 24R,25(OH)$_2$D$_3$ by the endocrine gland function of the kidney, small amounts of 1α,25(OH)$_2$D$_3$ are also produced in a paracrine fashion by both the placenta during pregnancy and under certain physiological states by activated macrophages in both keratinocytes and astrocytes. Target organs and cells for 1α,25(OH)$_2$D$_3$ contain nuclear receptors [VDR$_{nuc}$] for 1α,25(OH)$_2$D$_3$. Also 1α,25(OH)$_2$D$_3$ generates biological effects involving rapid action signal transduction pathways. The precise biological roles of 24R,25(OH)$_2$D$_3$ are not yet defined although it is believed to function via interaction with a specific receptor present in bone and cartilage. The FIG. 1 also indicates possible sites of action of agonist analogs as well as antagonist analogs.

The core elements of the vitamin D endocrine system, seen in FIG. 1, include several steps. First, 7-dehydroxycholestrerol is converted to vitamin D$_3$ or vitamin D$_3$ is supplied by the dietary intake from dietary sources (FIG. 1A). Vitamin D$_3$ is transported by blood to liver where vitamin D$_3$ is converted to 25(OH)D$_3$ which is the major form of vitamin D circulating in the blood (FIG. 1B). In the kidneys, functioning as endocrine glands, 25(OH)D$_3$ is converted into two principal dihydroxylated metabolites, namely to 1α,25(OH)$_2$D$_3$ and 24R,25(OH)$_2$D$_3$ (FIG. 1C). Utilizing vitamin D binding protein (DBP), the 1α,25(OH)$_2$D$_3$ and other metabolites are systemically transported to distal target organs (FIG. 1D). 1α,25(OH)$_2$D$_3$ binds to membrane or nuclear receptors of the target cells eliciting appropriate biological responses through a variety of signal transduction pathways (FIG. 1E), such as rapid actions elicited by agonist analogs, such as analogs JM, JN, JO and JP(FIG. 1F) or binding of agonist analogs to nuclear receptors, or working in hormone-like fashion or classic target organs, such as bone, resulting in mobilization or accretion of Ca$^{2+}$ and Pi; on intestine increasing absorption of calcium, or on kidneys, resulting in reabsorption of Ca$^2$ and Pi (FIG. 1H).

The model seen in FIG. 1 is based on the fact that vitamin D$_3$ is, in reality, a prohormone and is not known to have any intrinsic biological activity by itself. It is only after vitamin D$_3$ is metabolized first into 25(OH)D$_3$ in the liver and then into 1α,25(OH)$_2$D$_3$ and 24R,25(OH)$_2$D$_3$ by the kidney, that biologically active molecules are produced. In toto some 37 vitamin D$_3$ metabolites have been isolated and chemically characterized.

Analogs of the invention essentially work in the same way as the 1α,25(OH)$_2$D$_3$ metabolite. 1α,25(OH)$_2$D$_3$ analogs of the invention initiate selected biological responses via interaction with either a nuclear receptor for 1α,25(OH)$_2$D$_3$ [VDR$_{nuc}$] which regulates gene transcription or a cell membrane receptor [VDR$_{mem}$] which is coupled to signal transduction pathways which can generate rapid actions via opening voltage gated Ca$^{2+}$ channels and Cl channels and as well as by activating MAP-kinases.

Different shapes of the conformationally flexible 1α,25(OH)$_2$D$_3$ or its analogs bind to the VDR$_{nuc}$ and VDR$_{mem}$ and initiate biological responses via activation of signal transduction mechanisms which are coupled to either the VDR$_{nuc}$ or the VDR$_{mem}$. Thus, the totality of biological responses mediated by 1α,25(OH)$_2$D$_3$ and the analogs of the invention represents an integration of both nuclear receptor and membrane-receptor initiated events. FIG. 1 also indicates how analogs of 1α,25(OH)$_2$D$_3$ both conformationally flexible and conformationally restricted, acting as agonists or antagonists, may generate biological responses in the treatment of selected disease states. The presence of both a nuclear receptor [VDR$_{nuc}$] in over 30 target cells and a putative membrane receptor [VDR$_{mem}$] linked to the generation of rapid responses are specified.

Biological properties of the analogs of the invention and their conformational identification as well as their full chemical name and their code name are listed in Table 6.

TABLE 6

Properties of Analogs of 1α, 25(OH)$_2$D$_3$

| Code | Analog Name | Conformation | Genomic Response | Rapid Response | Antagonist |
|---|---|---|---|---|---|
| C | 1β, 25(OH)$_2$D$_3$ | Flexible | Yes | Yes | No |
| DE | 22-(m-hydroxyphenyl)1β, 25(OH)$_2$D$_3$ | Flexible | Yes | Yes | No |
| DF | 22-(p-hydroxyphenyl)1α, 25(OH)$_2$D$_3$ | Flexible | Yes | Yes | No |
| EV | 22-(m-dimethylhydroxymethyl)phenyl-23, 24, 25, 26, 27-pentanor-1α(OH)D$_3$ | Flexible | Yes | Yes | No |
| GE | 14-epi-1α, 25(OH)$_2$D$_3$ | Flexible | Yes | Yes | No |
| GF | 14-epi-1α, 25(OH)$_2$-pre-D$_3$ | Flexible | Yes | Yes | No |
| HH | 1β, 25(OH)$_2$-epi-D$_3$ | Flexible | No | No | Yes |
| HJ | 1α, 25(OH)$_2$-epi-D$_3$ | Flexible | Yes | Yes | No |
| HL | 1β, 25(OH)$_2$D$_3$ | Flexible | No | No | Yes |
| HQ | (22S)-1α, 25(OH)2-22, 23-diene-D$_3$ | Flexible | Yes | Yes | No |
| HR | (22R)-1α, 25(OH)2-22, 23-diene-D$_3$ | Flexible | Yes | Yes | No |
| HS | 1α, 18, 25(OH)$_2$D$_3$ | Flexible | Yes | Yes | No |
| IB | 23-(m-dimethylhydroxymethyl)phenyl-22-yne-24, 25, 26, 27-tetranor-1αOH)D$_3$ | Flexible | Yes | Yes | No |
| JM | 1α, 25(OH)$_2$-7-dehydrocholesterol | 6-s-cis locked | No. | Yes | No |
| JN | 1α, 25(OH)$_2$-7-lumisterol | 6-s-cis locked | No | Yes | No |
| JO | 1α, 25(OH)$_2$-pyrocalciferol | 6-s-cis locked | No | Yes | No |
| JP | 1α, 25(OH)$_2$-isopyrocalciferol | 6-s-cis locked | No | Yes | No |
| JR | 1α, 25(OH)$_2$-7, 8-cis-D$_3$ | Flexible | Yes | Yes | No |
| JS | 1α, 25(OH)$_2$-5, 6-trans-7, 8-cis-D$_3$ | Flexible | Yes | Yes | No |
| JV | (1S, 3R, 6S)-7, 19-retro-1α, 25(OH)$_2$D$_3$ | Flexible | Yes | Yes | No |
| JW | (1S, 3R, 6R)-7, 19-retro-1α, 25(OH)$_2$D$_3$ | Flexible | Yes | Yes | No |
| JX | 22-(p-hydroxyphenyl)-, 23, 24, 25, 26, 27-pentanor-D$_3$ | Flexible | Yes | Yes | No |
| JY | 22-(m-hydroxyphenyl)-, 23, 24, 25, 26, 27-pentanor-D$_3$ | Flexible | Yes | Yes | No |
| LO | 14α, 15α-methano-1α, 25(OH)$_2$D$_3$ | Flexible | Yes | Yes | No |

Analogs of 1α,25(OH)$_2$D$_3$ listed in Table 6 are identified by a code under which analogs were synthesized and tested. The Table 6 identify analogs by their slow genomic and/or rapid biological responses as well as their structural conformation. Analogs listed in genomic and rapid response columns were found to be agonists. Additionally, Table 3 identifies analogs which were confirmed (analog HL) or suspected (analog HH) antagonists. Analogs listed in Table 3 have a variety of biological properties as seen in FIG. 1 and also in FIG. 3.

Analogs listed in Table 6 are further identified by their conformational flexibility as either conformationally flexible represented by the analogs DE, DF, EV, GE, GF, HH, HJ, HL, HQ, HR, HS, JR, JS, JV, JW, JX, JY and LO, or as conformationally restricted 6-s-cis locked analogs represented by the analogs JM, JN, JO and JP.

General mode of action by which 1α,25(OH)$_2$D$_3$ generates biological responses in target cells is shown in FIG. 2. The conformationally flexible 1α,25(OH)$_2$D$_3$ interacts in a target cell with both the nuclear VDR$_{nuc}$ or membrane VDR$_{mem}$ to generate biological responses, as seen in FIG. 2. Similarly, analogs of 1α,25(OH)$_2$D$_3$ which are conformationally flexible interact in a target cell with both the nuclear VDR$_{nuc}$ and membrane VDR$_{mem}$ to generate biological responses (FIG. 2C). However, 6-s-cis locked conformationally restricted analogs of 1α,25(OH)$_2$D$_3$ may interact in a target cell with only the VDR$_{mem}$ to generate rapid biological responses.

The model seen in FIG. 2 describes the general mode of action of 1α,25(OH)$_2$D$_3$ metabolite. The model invokes ligand domains for receptors (the VDR$_{nuc}$ and VDR$_{mem}$ ) with different specificities for different shapes or conformers of 1α,25(OH)$_2$D$_3$. Thus, there exists two general classes of analogs; those that have complete flexibility around the 6,7 carbon-carbon bond, as does 1α,25(OH)$_2$D$_3$, and those analogs which are conformationally restricted, such as a 6,7-locked analogs, such as example 1α,25(OH)$_2$-7-dehydrocholesterol (JM) or 1α,25(OH)$_2$-lumisterol (JN).

FIG. 2 compares mode of actions of two types of analogs, such as example 1α,25(OH)$_2$-7-dehydrocholesterol (JM) or 1α,25(OH)$_2$-lumisterol (JN).

FIG. 2 compares mode of actions of two types of analogs, namely conformationally flexible analogs and conformationally restricted 6-s-cis analogs. As seen in FIG. 2A, 1α,25(OH)$_2$D$_3$ which is conformationally flexible interacts with both the membrane receptor depicted as VDR$_{mem}$ located in the cell membrane, and with cell nuclei receptor depicted as VDR$_{nuc}$ located in the cell nucleus of the target cell. As seen in FIG. 2A, 1α,25(OH)$_2$D$_3$ interacts directly either with VDR$_{mem}$ or VDR$_{nuc}$ thereby eliciting appropriate biological responses. The slow genomic responses appear after 1α,25(OH)$_2$D$_3$ interaction with VDR$_{nuc}$. Rapid responses are generated upon interaction with VDR$_{mem}$.

As seen in FIG. 2B, conformationally flexible analogs of the intention act similarly to 1α,25(OH)$_2$D$_3$ generating the biological responses as seen in FIG. 2A.

In FIG. 2C, where the action of conformationally restricted 6-s-cis analogs is illustrated, the only interaction which is observed is the interaction between the analog and VDR$_{mem}$ receptor thereby resulting solely in rapid nongenomic selected biological responses, as those seen in FIG. 1F.

Figure 3:
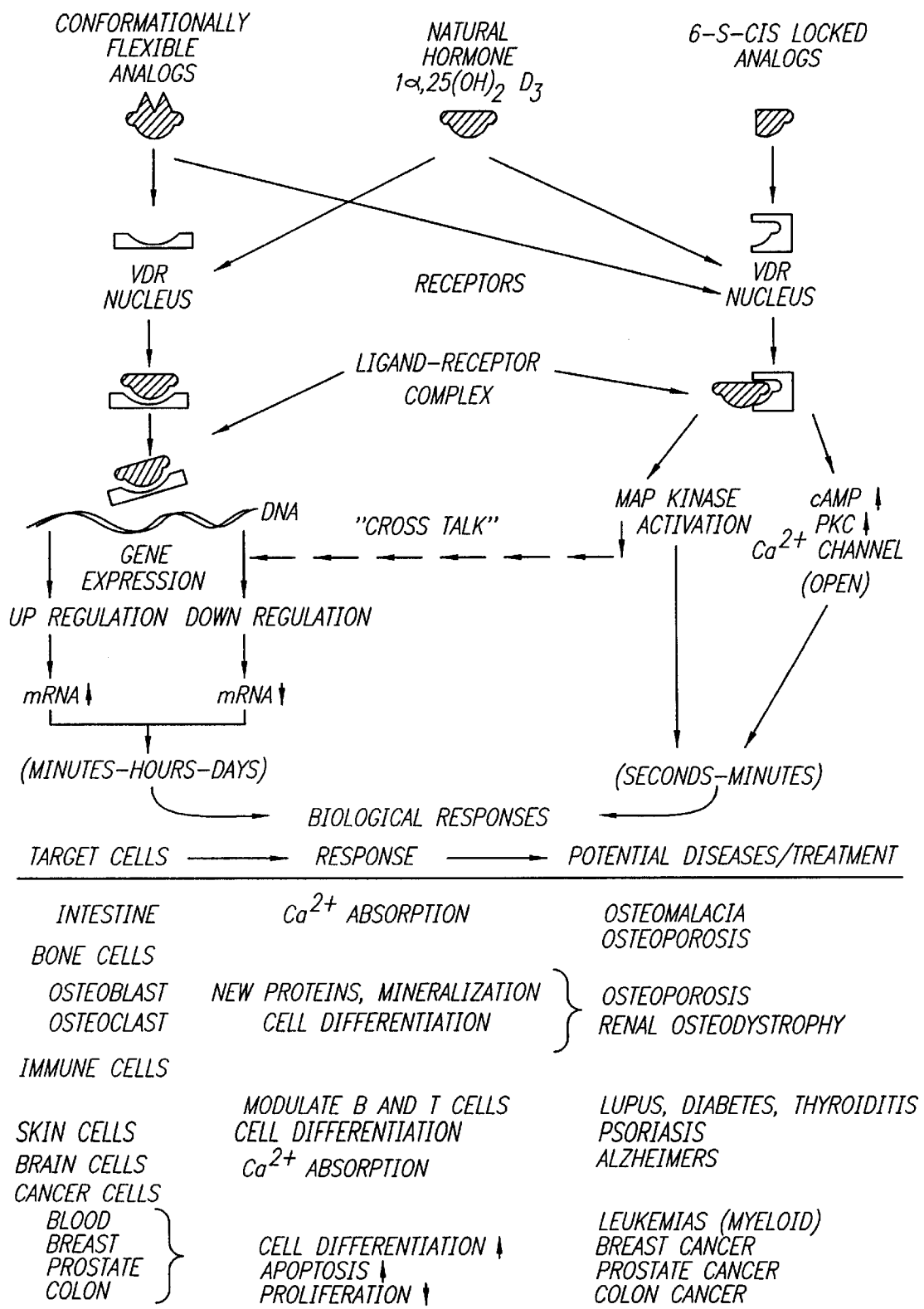
FIG. 3 represents a summary of mechanisms of action of 1α,25(OH)₂D₃ or its analogs in generating biological responses in target cells.

FIG. 3 is a model of the mechanisms of action by which 1α,25(OH)$_2$D$_3$ generates biological responses in target cells. The conformationally flexible natural hormone, 1α,25(OH)$_2$D$_3$, and conformationally flexible analogs interact with both the VDR$_{nuc}$ and VDR$_{mem}$ FIG. 3A. However, 6-s-cis locked analogs can interact only with the VDR$_{mem}$ (FIG. 3B). After occupancy of the receptors, appropriate signal transduction systems are initiated which ultimately lead to the generation of biological responses. The bottom panel of the FIG. 3 lists some target cells for 1α,25(OH)$_2$D$_3$ and identifies typical responses which occur therein. Disease states for treatment with analogs of 1α,25(OH)$_2$D$_3$ are listed in FIG. 3C.

FIG. 3 thus presents a general description summarizing the mechanisms of action by which 1α,25(OH)$_2$D$_3$ or its analogs generate biological responses in target cells and tabulates target cells linked to selected disease states which are treated via analogs of 1α,25(OH)$_2$D$_3$.

FIG. 3A shows the mechanism of action of conformationally flexible analogs which act with both the nuclear VDR$_{nuc}$ receptor or with membrane VDR$_{mem}$ receptor, depicting either the slow genomic responses or rapid responses. Slow responses proceed through formation of ligand-receptor complex, DNA expression of regulatory protein via mRNA up-regulating or down regulating biological responses in target cells. This process takes minutes/hours/days to achieve the desirable effect. However, its therapeutic value is very high as it achieves a correction of a disease caused either by overproduction or deficiency of the protein regulating the conditions causing the disease in the target cells.

The rapid response to the administration of the analog happens within seconds or minutes. In this respect, conformationally restricted 6-s-cis analogs are very effective as their administration elicits solely the rapid response rather than lengthy genomic response via gene expression. The mechanism of the rapid response is illustrated in FIG. 3B. However, as seen in FIG. 3, these 6-s-cis analogs may also modulate slow genomic responses by rapidly activating MAP-kinase. MAP-kinase activation discovered during the development of this invention, described in 60/060,173 provisional application filed on Oct. 26, 1997, results both in electing the rapid response or affecting slow genoric responses by so called "cross talking" to the nuclear DNA and causing modulation of gene transcription.

To exemplarize the utility of the invention, when, for example, a human subject suffers from osteomalacia, levels of 1α,25(OH)$_2$D$_3$ are low to undetectable, while in a healthy subject such levels are measured between 20 and 45 pg/ml of plasma. While the agonist analogs of the invention are administered to the subject suffering from osteomalacia, for example orally or intravenously, they enter the blood stream and are carried to the target cells via a specific vitamin D binding protein. In this case, the target cells are intestine mucosa cells in which the analog enhances calcium transport and absorption as well as phosphate (PO$_4$) transport and absorption. This example illustrates a rapid response where upon administration of the analog, the analog is carried to the intestine, binds to intestine mucosa cells and through cAMP and PKC increase, causes calcium channels in intestine cells to open allowing calcium absorption to increase and resulting in curing the disease. Similarly, one 1α,25(OH)$_2$D$_3$ is transplanted via DBP to bone cells where it interacts with the VDR$_{nuc}$. This results in an increased production of the bone proteins osteocalcium and osteopontin which are essential to the bone mineralization process.

Utility

The analogs of the invention are potent agonist for the genomic responses or antagonists of the rapid nongenomic responses connected with the biological action of vitamin D$_3$. They are therefore useful for treatment and prevention of diseases connected with either insufficiency or with overproduction of 1 α,25- dihydroxy vitamin D$_3$.

EXAMPLES

The following examples describe preparation of specific analogs. Schemes A-J illustrate preparation of the analogs as indicated.

Scheme A shows synthesis of analogs DE, DF and EV described in Examples 1–3.

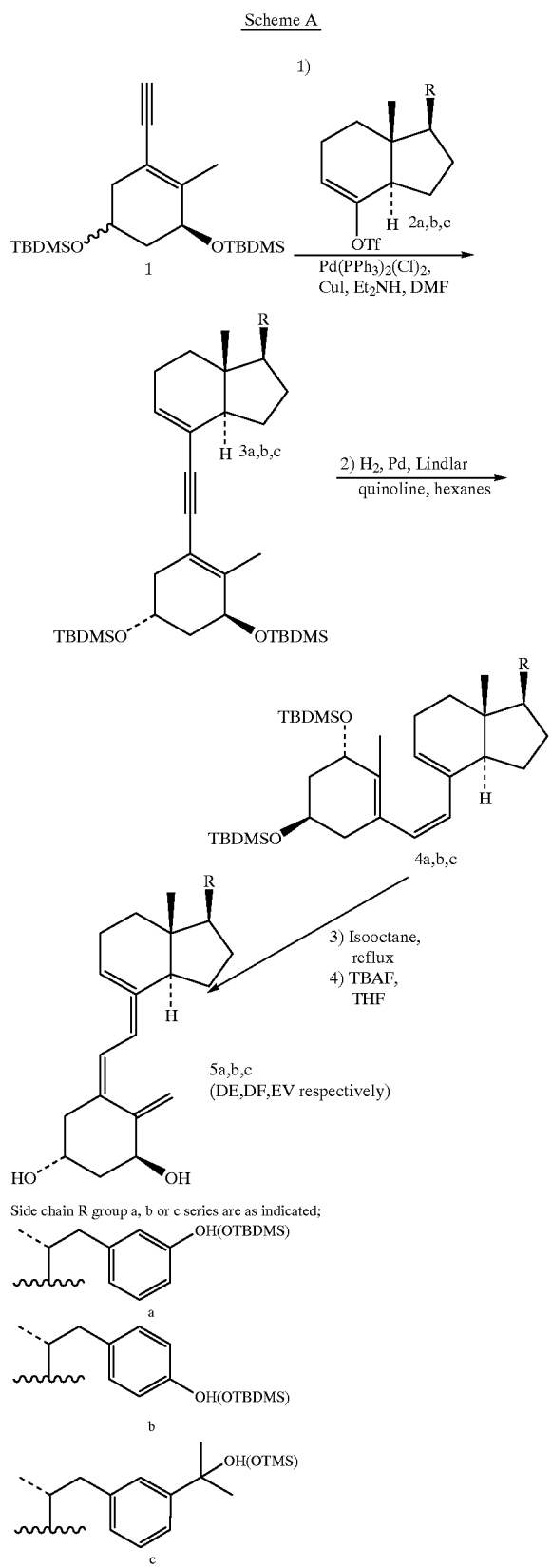

In compounds 2, 3 and 4, the side chain is protected as the silyl ether; in compound 5, it is the free OH.

Example 1

Chemical Synthesis of Analog DE

This example describes preparation of analog DE, namely 22-(m-hydroxyphenyl)-23,24,25,26,27-pentanor-1α(OH)D$_3$ according to Scheme A.

1α,3β-Di-(tert-butyldimethylsilyloxy)-22-(m-tert-butyldimethylsilyloxy)phenyl-24-nor-9,10-seco-chola-5(10),8-dien-6-yne, compound (3a)

The A-ring fragment 1 (0.077 g, 0.14 mmol) and 0.060 g (0.16 mmol) of the CD ring triflate (2a) were dissolved in 0.6 mL of dry DMF. Bis-triphenylphosphine palladium dichloride complex (Pd(PPh$_3$)Cl$_2$, 3 mg) and diethylamine (0.076 mL, 0.55 mmol) were then introduced. The mixture was heated to 80° C. for 5 h and then after cooling to room temperature, water was added and the mixture was extracted with ether. The combined ether extracts were washed successively with a solution 10% HCl, a solution saturated of NaHCO$_3$ and brine. After drying (MgSO$_4$) and concentrating the solution, the crude residue was passed through a short column of silica gel (1% EtOAc/hexanes) and then purified by HPLC (Rainin bynamax-60A column, 0.4% EtOAc/hexanes, 8 mL/min) to afford 86 mg (81%) of the dienyne 3a as a colorless residue.

Spectral Data: $^1$H-NMR: δ0.09 (6H, Me$_2$Si, s), 0.12 (6H, Me$_2$Si, s), 0.21 (6H, Me$_2$Si, s), 0.76 (3H, C$_{18}$—Me, s), 0.86 (3H, C$_{21}$—Me, d, J¯6.3 Hz), 0.91 (9H, t-Bu, s), 0.92 (9H, t-Bu, s), 1.00 (9H, t-Bu, s), 1.93 (3H, C$_{19}$—Me, s), 2.43 (1H, dd, J¯3.6 Hz, 16.2 Hz), 2.87 (1H, dd, J¯2.1 Hz, 13.2 Hz), 4.12 (1H, H$_1$, m), 4.22 (1H, H$_1$, m), 6.00 (1, H$_9$, m), 6.64 (1H, ArH$_2$, s), 6.68 (1H, Ar, d, J¯8.4 Hz), 6.76 (1H, Ar, d, J¯7.5 Hz), 7.13 (1H, ArH$_5$, t, J¯7.8 Hz).

$^{13}$C-NMR: δ−4.5, −4.4, −4.3, −4.1, −4.0, 11.3, 18.3, 18.4, 18.6, 19.4, 24.5, 25.4, 26.0, 26.1, 26.2, 28.9, 36.1, 39.1, 40.1, 41.5, 42.2, 42.8, 50.5, 55.3, 64.4, 70.3, 88.4, 92.6, 115.7, 117.5, 121.5, 122.6, 122.7, 129.1, 133.5, 140.7, 143.3, 155.6.

HRMS: m/z 762.5303 (calcd. for C$_{46}$H$_{78}$O$_3$Si$_3$, 762.5259).

MS: m/z 762 (2, M), 623 (25), 631 (57), 630 (base), 628 (11), 574 (10), 499 (18), 498 (41), 441 (6), 407 (2), 381 (2), 355 (2), 324 (19), 277 (11), 268 (10), 249 (11), 222 (32), 193 (4), 165 (4), 132 (3), 105 (3), 75 (52), 56 (2).

22-(m-Hydroxyphenyl)-23,24,25,26,27-pentanor-1α-hydroxyvitamin D$_3$ (5a) analog DE Dienyne, compound 3a (26 mg, 0.034 mmol) in 16 mL of EtOAc, 52 mg of Lindlar catalyst and quinoline (52 μL, 0.107 M in hexanes) were stirred for 1 h at room temperature under a positive pressure of hydrogen. The mixture was passed through a pad of diatomaceous earth and then the filtrate was evaporated to dryness. The residue in isooctane (14 mL) was refluxed for 2 h. The solvent was evaporated and to the residue was added 0.95 mL of THF and 0.23 mL of a solution of tetrabutylammonium fluoride (1 M in THF). After stirring the mixture at room temperature for 12 h, 2 mL of a saturated solution of NaCl was added. The mixture was extracted four times with EtOAc and the combined organic extracts were dried (MgSO$_4$) and then concentrated to dryness. After filtration of the residue through a pad of silica gel (EtOAc), HPLC purification (Rainin Dynamax, 1×25 cm, 8 μm, 4 mL/min, 100% EtOAc) to afford 8.3 mg (63%) of the vitamin D, compound 5(a) as a colorless, amorphous solid.

Spectral Data: $^1$H-NMR: δ0.58 (3H, C$_{18}$—Me, s), 0.83 (3H, C$_{21}$—Me, d, J¯6.3 Hz), 2.32 (1H, dd, J¯6.6 Hz, 13.2 Hz), 2.61 (1H, dd, J¯1.5 Hz, 13.5 Hz), 2.84 (1H, apparent dt, J¯2.1 Hz, 12.9 Hz; this signal most likely consists of two doublets both with J¯12.9 Hz assignable to H$_{9β}$ and probably one of the two H$_{22}$ protons), 4.24 (1H, H$_3$, broad s), 4.44 (1H, H$_1$, broad s), 4.60 (1H, ArOH, broad s), 5.02 (1H, H$_{19}$, s), 5.34 (1H, H$_{19}$, s), 6.04 (1H, H$_7$, d, J¯11.4 Hz), 6.39 (1H, H$_6$, d, J¯11.4 Hz), 6.63 (1H, ArH$_2$, s), 6.64 (1H, Ar, d, J¯7.5 Hz), 6.71 (1H, Ar, d, J¯7.5 Hz), 7.13 (1H, ArH$_5$, t, J¯7.5 Hz). UV: (95% EtOH) λ$_{max}$ 268 nm (ε20,600).

HRMS: 422.2839 (calcd. for C$_{28}$H$_{38}$O$_3$, 422.2821). MS: m/z 422 (10, M), 404 (base), 386 (12), 363 (3), 349 (2), 334 (2), 315 (4), 297 (6), 269 (10), 251 (8), 227 (6), 195 (9), 159 (15), 155 (12), 152 (7), 134 (31), 107 (85), 91 (34), 79 (25), 67 (16), 55 (23).

Example 2

Chemical Synthesis of Analog DF

This example illustrate preparation of analog DF, namely 22-(p-hydroxyphenyl)-23,24,25,26,27-pentanor-1α-hydroxyvitamin-D$_3$. The preparation of analog DF seen in Scheme A.

Preparation of 1α,3β-Di-(tert-butyldimethylsilyloxy) -22-(p-tert- butyldimethylsilyloxy)phenyl-24-nor-9,10-seco-chola-5(10),8-dien-6-yne, compound(3b)

The CD-ring triflate 2b (0.053 g, 0.1 mmol) and the A-ring 1 (0.046 g, 0.12 mmol) were dissolved under argon in 0.4 mL of dry DMF (distilled from benzene and then from BaO). Diethylamine (0.054 mL, 0.39 mmol) and bistriphenylphosphine palladium dichloride (2 mmol, 2 mg, Pd(PPh$_3$)$_2$Cl$_2$) were added and the mixture was heated at 80° C. for 4.5 h. The solution was cooled and then diluted with ether. The organic layer was separated, washed with a solution 10% HCl, a saturated solution of NaHCO$_3$ and then brine. After drying (MgSO$_4$) and concentrating, the residue was purified by HPLC (Rainin Dynamax-60A column, 0.4% EtOAc/hexanes, 8 mL/min) to afford 0.061 g (80%) of the dienyne 3b as a colorless, residual oil.

Spectral Data: $^1$H-NMR: δ0.08 (6H, Me$_2$Si, s), 0.12 (6H, Me$_2$Si, s), 0.20 (6H, Me$_2$Si, s), 0.75 (3H, C$_{18}$—Me, s), 0.84 (3H, C$_{21}$—Me, d, J¯6.0 Hz), 0.91 (9H, t-Bu, s), 0.92 (9H, t-Bu, s), 0.99 (9H, t-Bu, s), 1.93 (3H, C$_{19}$—Me, s), 2.43 (1H, dd, J¯3.6 Hz, 16.2 Hz), 2.85 (1H, dd, J¯2.1 Hz, 13.2 Hz), 4.13 (1H, H$_3$, m), 4.21 (1H, H$_1$, broad s), 5.99 (1H, H$_9$, m), 6.76 (2H, ArH$_{3,5}$, d, J¯8.4 Hz), 7.00 (2H, ArH$_{2,6}$, d, J¯8.1 Hz). $^{13}$C-NMR: δ−4.8, −4.7, −4.6, −4.4, −4.3, 11.1, 18.0, 18.2, 19.2, 24.3, 25.2, 25.7, 25.8, 25.9, 28.6, 35.8, 39.1, 39.8, 41.3, 41.8, 42.0, 50.2, 55.1, 64.2, 70.0, 88.2, 92.4, 115.5, 119.6, 122.5, 130.3, 133.3, 134.1, 140.4, 153.5.

HRMS: m/z 762.5289 (calcd. for C$_{46}$H$_{78}$O$_3$Si$_3$, 762.5259).

MS: m/z 762 (2, M), 632 (18), 631 (43), 630 (78), 574 (6), 500 (11), 499 (30), 498 (73), 441 (3), 409 (2), 277 (8), 249 (8), 222 (22), 221 (base), 195 (2), 165 (19), 132 (6), 105 (3), 75 (93), 56 (3).

Preparation of analog DF 22-(p-hydroxyphenyl)-23, 24,25,26,27-pentanor-1α-hydroxyvitamin-D$_3$, compound (5b)

A mixture of dienyne 3b (0.019 g, 0.025 mmol) in ethyl acetate (11 mL), quinoline (0.17 M in hexanes, 0.040 mL, 0.42 mmol) and Lindlar's catalyst (0.040 g) was stirred under an atmosphere of hydrogen for 1 h. After filtration of the mixture through a short pad of silica gel and concentration, the crude residue was purified by HPLC (Rainin Dynamax, 1.0×25 cm, 8 μm silica gel column, 0.4% EtOAc/hexanes). The inseparable previtamin and vitamin mixture was dissolved in isooctane (7 mL) and heated to reflux for 2 h, following which the solvent was removed. The residue was dissolved in THF (0.5 mL) and tetrabutylammonium fluoride (1 M in THF, 0.117 mL, 0.117 mmol) was added at room temperature. The solution was stirred at 20° C. for 12 h. A saturated solution of NaCl (1 mL) was added and then the mixture was extracted with ethyl acetate (4×2 mL). The combined organic extracts were dried (MgSO$_4$) and then concentrated to dryness. The crude material, after passage through a short pad of silica gel (EtOAc), was purified by HPLC (Rainin Dynamax 1.0×25 cm, 8 μm, 100% EtOAc) to afford the vitamin 5b (3.6 mg, 34%) as an amorphous, white solid.

Spectral Data: $^1$H-NMR: δ0.57 (3H, C$_{18}$—Me, s), 0.81 (3H, C$_{21}$—Me, d, J~6.6 Hz), 2.33 (1H, dd, J~13.5 Hz, 6.6 Hz), 2.61 (1H, dd, J~13.5 Hz, 2.7 Hz), 2.82 (2H, apparent dd, J~13.5 Hz, 2.4 Hz; this signal most likely consists of overlapping doublets assignable to H$_{9β}$ and probably one of the H$_{22}$ protons), 4.24 (1H, H$_3$, m), 4.44 (1H, H$_1$, m), 5.01 (1H, H$_{19}$, s), 5.34 (1H, H$_{19}$, s), 6.03 (1H, H$_7$, d, J~11.1 Hz), 6.38 (1H, H$_6$, d, J~11.1 Hz), 6.74 (2H, ArH$_{3,5}$, d, J~8.3 Hz), 6.99 (2H, ArH$_{2,6}$, d, J~8.3 Hz).

UV: (abs. EtOH) λ$_{max}$ 266 nm (ε 20,000).

HRMS: m/z 422.2824 (calcd. for C$_{28}$H$_{38}$O$_3$, 422.2821).

MS: m/z 422 (19, M), 404 (15), 386 (25), 363 (8), 348 (8), 320 (3), 297 (9), 279 (5), 241 (6), 223 (7), 197 (12), 157 (16), 155 (12), 152 (3), 134 (32), 107 (base), 95 (14), 81 (13), 71 (14), 57 (15), 55 (26).

Example 3

Chemical Synthesis of Analog EV

This example illustrates preparation of the analog EV, namely 22-[3-(1'-Methyl-1'-hydroxyethyl)phenyl]-23,24, 25,26,27-pentanor-1α-hydroxyvitamin D$_3$. Preparation of analog EV is seen in Scheme A.

Preparation of 1α,3β-Di(tert-butyldimethylsilyloxy)-22-[3-(1'-methyl-1'-trimethylsilyloxyethyl)phenyl]-24-nor-9,10-seco-chola-5(10),8-dien-6-yne, compound (3c)

CD ring triflate 2c (0.032 g, 0.06 mmol) and A-ring enyne 1 (0.025 g, 0.06 mmol) were stirred in DMF (0.4 mL) in the presence of 1.5 mg of Pd(PPh$_3$)$_2$(OAc)$_2$, 1 mg of cuprous iodide and 0.4 mL of Et$_2$NH. After stirring the mixture for 2 h at room temperature, water was added and the mixture was extracted with ether. The combined ether extracts were washed with a 10% solution of HCl, a saturated solution of NaHCO$_3$ and brine. After drying (MgSO$_4$), the solvent was evaporated and the residue was filtered through a pad of silica gel, (1% EtOAc-hexanes). The crude dienyne 3c was purified by HPLC (Rainin Dynamax, 1.0×25 cm, 8 μm, 0.5% EtOAc/hexanes, 4 mL/min) to afford 42 mg (93%) of dienyne as a chromatographically homogeneous, colorless oil.

Spectral Data: $^1$H-NMR: δ0.09 (12H, 4MeSi, s), 0.11 (9H, 3MeSi, s), 0.76 (3H, C$_{18}$—Me, s), 0.86 (3H, C$_{21}$—Me, d, J~6.6 Hz), 0.90 (9H, t-Bu, s), 0.91 (9H, t-Bu, s), 1.59 and 1.60 (3H and 3H, diastereotopic Me$_2$C, two s), 1.93 (3H, C$_{19}$—Me, s), 2.43 (1H, dd, J~2.7 Hz, 15.9 Hz), 2.93 (1H, dd, J~2.1 Hz, 13.2 Hz), 4.11 (1H, H$_3$, broad m), 4.21 (1H, H$_1$, br s), 5.99 (1H, H$_9$, m), 7.01 (1H, Ar, d, J~6.6 Hz), 7.24 (3H, Ar, m).

$^{13}$C-NMR: δ−4.8, −4.7, −4.6, −4.3, 2.3, 11.1, 14.1, 18.0, 18.1, 18.3, 19.2, 22.7, 24.3, 25.2, 25.8, 25.9, 26.0, 28.7, 31.6, 32.3, 32.7, 35.8, 39.0, 39.8, 41.3, 42.0, 42.8, 50.2, 55.1, 64.2, 70.0, 75.2, 88.2, 92.4, 115.5, 121.9, 122.5, 126.0, 127.3, 127.5, 133.3, 140.4, 140.9, 149.7.

HRMS: 762.5207 (calcd. for C$_{46}$H$_{78}$O$_3$Si$_3$, 762.5259).

MS: m/z 762 (2, M), 747 (4), 705 (2), 633 (5), 632 (18), 631 (44), 630 (78), 574 (5), 541 (10), 540 (18), 494 (9), 438 (2), 408 (13), 362 (3), 308 (2), 277 (4), 249 (4), 207 (4), 131 (20), 75 (base), 73 (37).

Preparation of analog EV, namely 22-[3-(1'-Methyl-1'-hydroxyethyl)phenyl]-23,24,25,26,27-pentanor-1α-hydroxyvitamin D$_3$, compound (5c)

Dienyne 3c (0.020 g, 0.026 mmol) was dissolved in 13 mL of EtOAc and 42 μL of a solution of quinoline (0.17 M in hexanes) and then 42 mg of Lindlar catalyst were added. The mixture was stirred for 1 h under a positive pressure of hydrogen at room temperature and then filtered through a short column of silica gel. After concentrating the filtrate, the crude residue was purified by flash chromagraphy (1% EtOAc/hexanes) to afford 17 mg of the mixture of vitamin and previtamin. This mixture was added to 10 mL of isooctane and the solution was heated at reflux for 2 h. After evaporation of solvent, the crude product was dissolved in 0.7 mL of dry THF and 0.17 mL of a THF solution 1 M of tetrabutylammonium fluoride. The mixture was stirred at room temperature for 12 h protected from the light and then 2 mL of a saturated solution of NaCl was added. The mixture was extracted with EtOAc and then the combined organic extracts were dried over MgSO$_4$ and concentrated. After passing the residue through a short column of silica gel, the crude product was purified by HPLC (Rainin Dynamax, 1.0×25 cm, 8 μm, 100% EtOAc, 4 mL/min) to afford 3.9 mg (32%) of the vitamin 5c as a white, amorphous solid.

Spectral Data: $^1$H-NMR: δ0.58 (3H, C$_{18}$—Me, s), 0.82 (3H, C$_{21}$—Me, d, J~6.6 Hz), 1.55 and 1.58 (3H and 3H, diastereotopic Me$_2$C, two s), 2.32 (1H, dd, J~6.3 Hz, 13.2 Hz), 2.61 (1H, dd, J~2.7 Hz, 13.2 Hz), 2.83 (1H, br d, J~12.6 Hz), 2.93 (1H, dd, J~2.4 Hz, 13.2 Hz), 4.23 (1H, H$_3$, m), 4.44 (1H, H$_1$, m), 5.02 (1H, H$_{19}$, br s), 5.34 (1H, H$_{19}$, br s), 6.04 (1H, H$_7$, d, J~11.1 Hz), 6.39 (1H, H$_6$, d, J~11.1 Hz), 7.02

(1H, Ar, d, J~6.9 Hz), 7.26 (3H, Ar, m). The signals at δ2.83 and 2.93 are probably assignable to H$_{9\beta}$ and one of the H$_{22}$ protons, respectively, or vice versa.

UV: (95% EtOH) $\lambda_{max}$ 266 nm (ε 19,500).

HRMS: m/z 464.3307 (calcd. for C$_{31}$H$_{44}$O$_3$, 464.3290). MS: m/z 464 (14, M), 446 (33), 428 (55), 410 (base), 384 (10), 369 (5), 341 (5), 313 (7), 297 (11), 277 (10), 251 (20), 225 (12), 209 (24), 195 (16), 171 (18), 155 (19), 152 (7), 134 (18), 131 (27), 105 (25), 95 (12), 81 (9), 69 (5), 59 (5).

Scheme B relates to analogs GE and GF described in Examples 4 and 5.

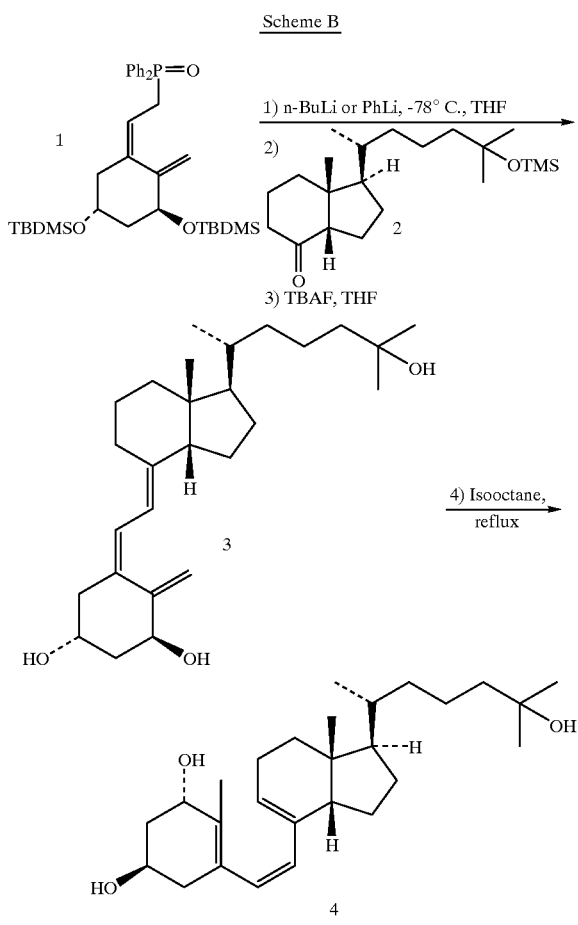

Example 4

Chemical Synthesis of Analog GE

This example illustrates preparation of the analog GE, namely 14-Epi-1α,25-dihydroxyvitamin D$_3$ according to Scheme B.

Preparation of 14-Epi-1α,25-dihydroxyvitamin D$_3$ (Analog GE, Compound 3)

To a stirred solution of 1 (67 mg, 0.11 mmol) in anhydrous THF (1.4 mL) at −78° C. under argon was added n-butyllithium (74 μL, 0.12 mmol, 1.55 M solution in hexanes) to give a deep orange solution. After adding CD ketone 2 (27.1 mg, 0.076 mmol) in dry THF (0.46 mL), the solution was stirred for 3 h at −78° C. and then warmed to rt. After concentration, the residue dissolved in ether (3 mL) and washed with a saturated solution of NaHCO$_3$ (3 mL) and brine (3 mL). After drying (MgSO$_4$) and concentrating the ether solution, the crude residue was purified by flash chromatography to afford 48.2 mg (86% yield) of protected vitamin, which was treated with TBAF (0.79 mL, 0.79 mmol, 1 M solution in THF). After 3 h, the solvent was removed and the crude residue dissolved in EtOAc (5 mL). The solution was washed (water, 3 mL; and brine, 3 mL), dried (Na$_2$SO$_4$), filtered and concentrated. Purification by HPLC (50% EtOAc/hexanes, Rainin Dynamax 60 Å column) afforded after vacuum drying 11 mg (81%) of vitamin 3.

$^1$H-NMR (300 MHZ): (CDCl$_3$) δ0.87 (3H, C$_{21}$—CH$_3$, d, J~6.4 Hz), 0.90 (3H, C$_{18}$—CH$_3$, s), 1.22 (6H, C$_{26,27}$—CH$_3$, s), 2.31 (1H, dd, J~13.2 Hz, 7.2 Hz), 2.46 (1H, br d, J~14.3 Hz), 2.60 (1H, dd, J~13.3 Hz, 3.5 Hz), 4.23 (1H, H$_3$, m), 4.44 (1H, H$_1$, t, J~5.4 Hz), 5.00 (1H, H$_{19}$, br s), 5.34 (1H, H$_{19}$, br s), 6.14 and 6.33 (2H, H$_{6,7}$-AB pattern, d, J~11.2 Hz).

Example 5

Chemical Synthesis of Analog GF

This example illustrates preparation of the analog GF, namely 14-Epi-1α,25-dihydroxyprevitamin D$_3$. Preparation of analog GF is seen in Scheme B.

Preparation of 14-Epi-1α,25-dihydroxyprevitamin D$_3$, compound (4)

A solution of vitamin 3 (4.9 mg, 0.012 mmol) in benzene-d$_6$ (2 mL) was subjected to three freeze-thaw cycles under vacuum and then placed in a thermostated bath at 80.0° C. After 4 h, the solution was cooled to rt and the vitamin/previtamin ratio determined by $^1$H-NMR integration (~7:93). The solution was concentrated and purified by HPLC (100% EtOAc, Rainin Dynamax 60 Å column) to afford, in order of elution, epi-vitamin 3 (0.3 mg) and epi-previtamin 4 (3.7 mg).

$^1$H-NMR (300 MHZ): (CDCl$_3$) δ0.91 (3H, C$_{18}$—CH$_3$, s), 0.94 (3H, C$_{21}$—CH$_3$, d, J~6.3 Hz), 1.22 (6H, C$_{26,27}$—CH$_3$, s), 1.75 (3H, C$_{19}$—CH$_3$, br s), 2.55 (1H, br d, J~16.6 Hz), 4.05 (1H, H$_3$, m), 4.18 (1H, H$_1$, br s), 5.65 (1H, H$_9$, m), 5.80 and 5.85 (H$_{6,7}$, AB pattern, d, J~12.5 Hz).

Scheme C relates to analogs HH, HJ and HL described in Examples 6–8.

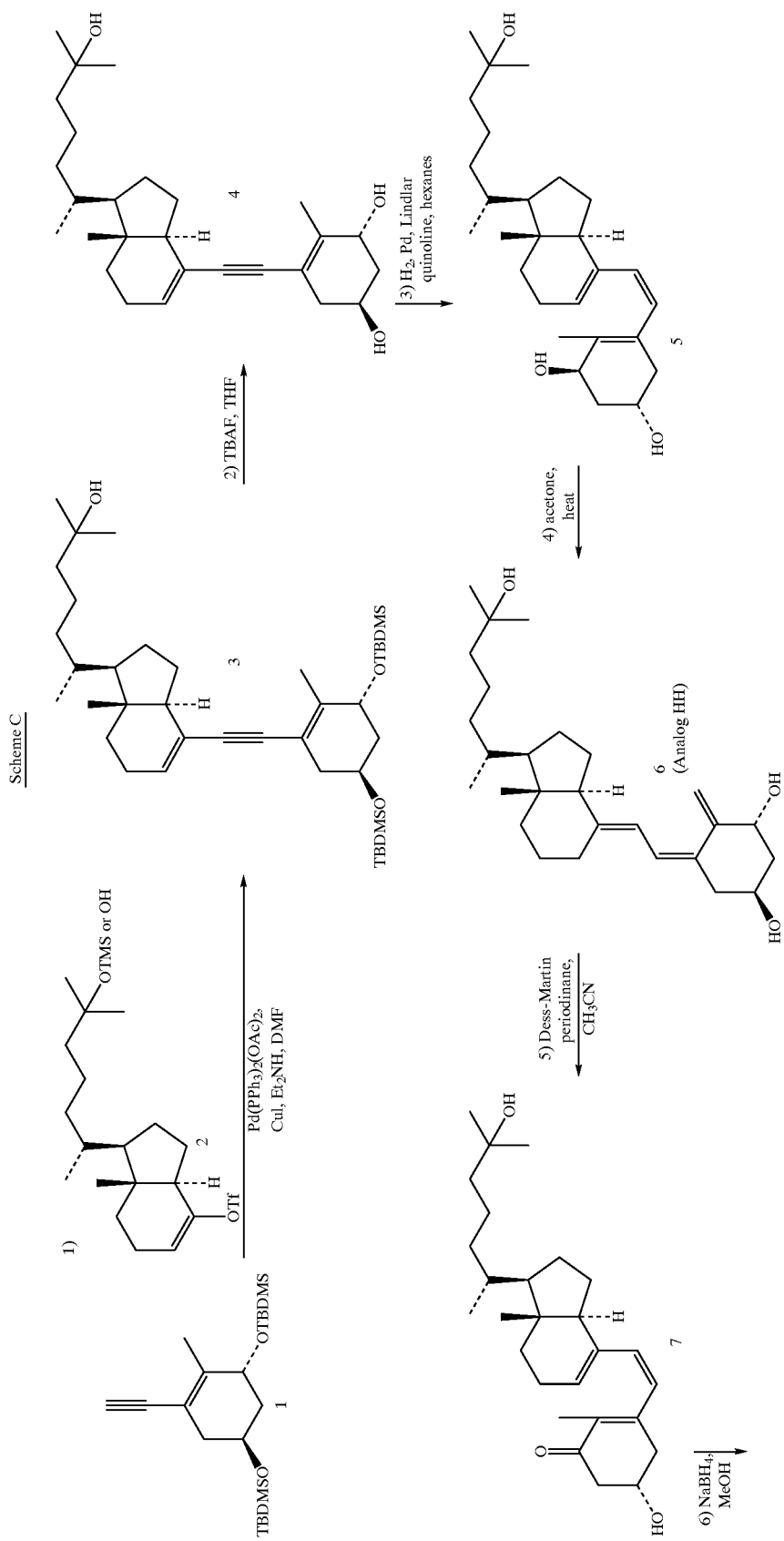

-continued
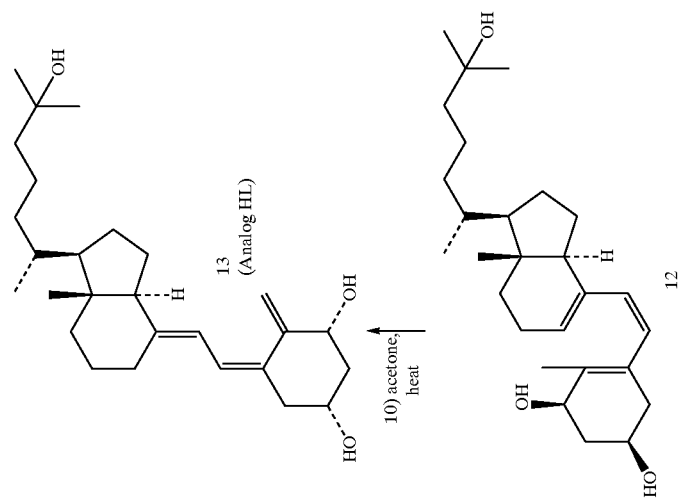
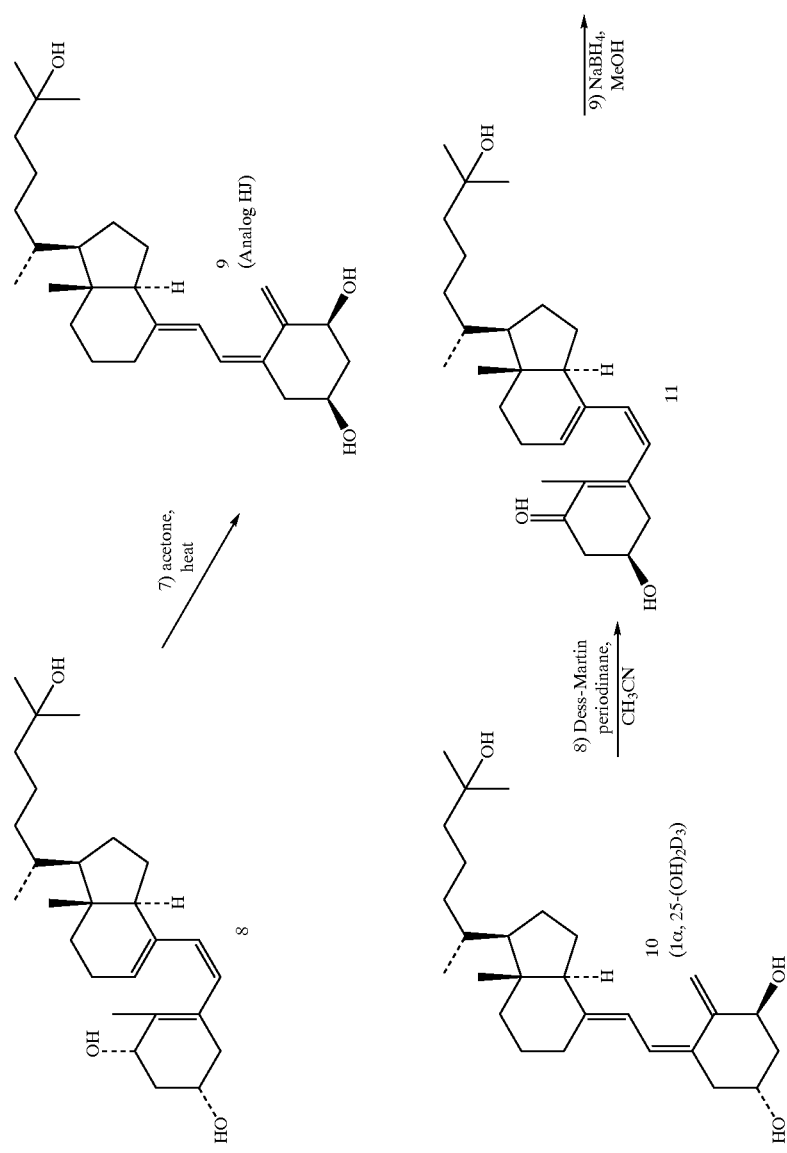

Example 6

Chemical Synthesis of Analog HH

This example illustrates preparation of the analog HH, namely 1β,25-dihydroxy-3-epivitamin $D_3$. Preparation of analog HH is according to as seen in Scheme C.

Preparation of 1β-[(tert-butyldimethylsilyl)oxy]-6,7-dehydro-25-hydroxy-3-epiprevitamin $D_3$ tert-Butyldimethylsilyl ether, compound (3)

To a mixture of enol triflate 2 (80 mg, 0.2 mmol) and 1β,3α-enyne 1 (84 mg, 0.22 mmol) in diethylamine (1 mL) and dimethylformamide (1 mL) was added CuI (4.8 mg, 0.003 mmol) and bis[triphenylphosphine]palladium(II) acetate (5.0 mg, 0.007 mmol). The reaction mixture was stirred at room temperature for 1.5 h under argon. Ether was added and the mixture was washed with $H_2O$ (3×5 mL), dried ($MgSO_4$) and evaporated in vacuo. The crude dark brown oil was purified by flash chromatography (10% ethyl acetate-hexane) to afford after vacuum drying 102 mg (79%) of the dienyne 3 as a viscous oil, which was sufficiently pure for the next step.

$^1$H-NMR (300 MHZ): ($CDCl_3$) δ0.06 (6H, Si—$CH_3$, s), 0.09 (6H, Si—$CH_3$, s), 0.70 (3H, $C_{18}$—$CH_3$, s), 0.88 (18H, Si-t-Bu, two s), 0.95 (3H, $C_{21}$—$CH_3$, d, J¯6.6 Hz), 1.21 (6H, $C_{26,27}$—2$CH_3$, s), 1.89 (3H, $C_{19}$—$CH_3$, s), 2.45 (1H, $C_{14}$—H, dd, J¯16.5 Hz, 4.5 Hz), 4.0–4.1 (1H, $H_3$, br m), 4.18 (1H, $H_1$, m), 5.96 (1H, $H_9$, d, J¯3.0 Hz).

$^{13}$C-NMR (75.5 MHZ): ($CDCl_3$) δ−4.8, −4.7, −4.6, −4.3, 11.1, 18.0, 18.1, 18.7, 19.1, 20.8, 24.2, 25.2, 25.8, 25.9, 28.0, 29.2, 29.4, 35.9, 36.2, 36.4, 39.8, 41.3, 41.9, 44.4, 50.2, 54.7, 64.2, 70.0, 71.1, 88.1, 92.4, 115.5, 122.6, 133.2, 140.3. A satisfactory mass spectrum of this substance could not be obtained. It was best characterized as the corresponding deprotected alcohol.

Preparation of 1β,25-dihydroxy-6,7-dehydro-3-epiprevitamin $D_3$ compound (4)

To a solution of dienyne 3 (76 mg, 0.12 mmol) in 5 mL THF under argon was added tetrabutylammonium fluoride (0.6 mL of 1.0 M solution in THF, 0.6 mmol). The reaction mixture was stirred at room temperature in the dark for 12 h. It was diluted with ethyl acetate and washed with brine (2×10 mL). The aqueous layer was extracted with ethyl acetate (2×10 mL) and the combined organic layer was dried ($MgSO_4$) and evaporated in vacuo. Flash chromatography of the residual oil (elution with 50% ethyl acetate-hexane followed by 90% ethyl acetate-hexane) afforded after vacuum drying 38 mg (76%) of the triol 4 as a colorless oil, which was sufficiently pure for characterization and further reaction.

$^1$H-NMR (300 MHZ): ($CDCl_3$) δ0.69 (3H, $C_{18}$—$CH_3$, s), 0.95 (3H, $C_{21}$—$CH_3$, d, J¯6.6 Hz), 1.21 (6H, $C_{26,27}$—$CH_3$, s), 1.98 (3H, $C_{19}$—$CH_3$, br s), 2.54 (1H, $H_{14}$, dd, J¯16.0 Hz, 4.0 Hz), 4.04–4.12 (1H, $H_3$, br m), 4.23–4.28 (1H, $H_1$, narrow m), 5.97–5.98 (1H, $H_9$, narrow m).

$^{13}$C-NMR (75.5 MHZ): ($CDCl_3$) δ11.1, 18.7, 18.8, 20.8, 24.2, 25.2, 28.0, 29.2, 29.3, 35.9, 36.2, 36.4, 39.2, 40.0, 41.9, 44.3, 50.1, 54.7, 63.4, 69.3, 71.1, 87.5, 93.4, 116.2, 122.4, 133.8, 139.4.

UV: (95% EtOH) $\lambda_{max}$ 272 nm (ε 14,400), 286 nm (ε 11,000).

HRMS: (FAB, NBA matrix) m/z 414.3146 (calcd. for $C_{27}H_{42}O_3$, 414.3134).

MS: (FAB, NBA matrix) m/z 414 (15, M), 413 (11), 397 (base, M−OH), 379 (11), 363 (3), 341 (3), 323 (2), 267 (6), 255 (3), 237 (3), 197 (7), 179 (10), 165 (19).

Preparation of analog HH, 1β,25-Dihydroxy-3-epivitamin $D_3$, compound (6)

A stirred mixture of dienyne 4 (27 mg, 0.065 mmol), Lindlar catalyst (27 mg) and quinoline (308 μl, 0.17 M in hexanes) in methanol (2.5 mL) was exposed to a positive pressure of hydrogen gas for 22 min. The mixture was filtered and concentrated to afford a residual oil which was purified by flash chromatography (elution with 50% ethyl acetate-hexane followed by 90% ethyl acetate-hexane) to afford 27 mg of the crude previtamin 5. $^1$H-NMR analysis of the latter material showed the complete absence of starting material. A solution of the crude previtamin (27 mg, 0.065 mmol) in acetone (1 mL) was placed in a screw capped vial and heated for 4 h in a constant temperature bath set at 80° C. The residue was concentrated under vacuum and purified by HPLC (85% ethyl acetate-hexane, 4 mL/min, Rainin Dynamax 60A column) to afford after vacuum drying 15 mg (56%) of the vitamin 6 as a colorless oil.

$^1$H-NMR (300 MHZ): ($CDCl_3$) δ0.54 (3H, $C_{18}$—$CH_3$, s), 0.93 (3H, $C_{21}$—$CH_3$, d, J¯6.0 Hz), 1.21 (6H, $C_{26,27}$—$CH_3$, s), 2.30 (1H, $H_{4\beta}$, dd, J¯13.0 Hz, 7.5 Hz), 2.62 (1H, $H_{4\alpha}$, dd, J¯13.0 Hz, 3.7 Hz), 2.82 (1H, $H_{9\beta}$, dd, J¯11.8 Hz, 3.0 Hz), 4.15–4.30 (1H, $H_3$, m), 4.40–4.50 (1H, $H_1$, m), 5.00 (1H, $H_{19}$, narrow m), 5.32 (1H, $H_{19}$, narrow m), 6.01 and 6.39 (2H, $H_{6,7}$, AB pattern, J¯11.4 Hz).

$^{13}$C-NMR (75.5 MHZ): ($CDCl_3$) δ12.0, 18.8, 20.8, 22.3, 23.6, 27.6, 29.1, 29.2, 29.4, 29.7, 36.1, 36.4, 40.5, 42.8, 44.4, 45.5, 45.9, 56.3, 56.5, 66.8, 71.4, 112.6, 117.0, 125.0, 132.7, 143.3, 147.3.

IR: ($CCl_4$) ν 3357 (OH, br s), 2944 (sp$^3$CH, br s), 1377 (s), 1216 (s), 1053 (s), 667 (s) cm$^{-1}$.

UV: (95% EtOH) $\lambda_{max}$ 264 nm (ε 17,000).

HRMS: m/z 416.3288 (calcd. for $C_{27}H_{44}O_3$, 416.3292).

MS: m/z 416 (21, M), 398 (72, M−$H_2O$), 380 (36, M−2$H_2O$), 362 (3), 329 (3), 285 (11), 251 (10), 227 (9), 197 (8), 152 (29, A-ring portion after $C_{7,8}$-cleavage), 134 (base, m/z 152−$H_2O$).

Example 7

Chemical Synthesis of Analog HJ

This example illustrates preparation of the analog HJ, namely 1α,25-dihydroxy-3-epivitamin $D_3$. The analog HJ is prepared according to Scheme C.

Preparation of 1-αxo-25-hydroxy-3-epiprevitamin $D_3$ compound (7)

1β,25-dihydroxy-3-epivitamin $D_3$ compound (6), (28.0 mg, 0.067 mmol) was added to the Dess-Martin periodinane reagent (40 mg, 0.10 mmol) in dry $CH_3CN$ (12 mL). The reaction mixture was stirred at room temperature for 60 min under argon. The resulting bright yellow solution was diluted with ether and washed with a 1:1 mixture (v/v) of saturated aqueous $Na_2S_2O_3$ and $NaHCO_3$ solution (20 mL). The organic layer was then dried ($MgSO_4$) and evaporated to dryness. The residue was purified by flash column chromatography on silica gel using 1:3 hexane:ethyl acetate to afford after vacuum drying 25 mg (90%) of 1-oxo-25-hydroxy-3-epiprevitamin $D_3$ as a pale yellow oil, which was sufficiently pure for spectral characterization and further reaction.

$^1$H-NMR (300 MHZ): ($CDCl_3$) δ0.71 (3H, $C_1$—$CH_3$), 0.96 (3H, $C_{21}$—$CH_3$, d, J¯6.6 Hz), 1.21 (6H, $C_{26,27}$—2$CH_3$, s), 1.78 (3H, $C_{19}$—$CH_3$, s), 2.4–2.6 (1H, m), 2.70–2.85 (1H, m), 4.16 (1H, $H_3$, m), 5.47 (1H, $H_9$, m), 6.05 and 6.11 (2H, $H_{6,7}$, AB pattern, J¯11.7 Hz).

UV: (95% EtOH) $\lambda_{max}$ 242 nm (ε 10,000), 298 nm (ε 11,200).

HRMS: (CI, NH$_3$) m/z 414.3145 (calcd. for C$_{27}$H$_{42}$O$_3$, 414.3136).

MS: (CI, NH$_3$) m/z 415 (15, MH), 414 (7, M), 396 (86, M–H$_2$O), 379 (base, MH–2 H$_2$O), 363 (4), 338 (2), 323 (3), 295 (2), 267 (10), 253 (4), 239 (3), 213 (6), 199 (4), 171 (9), 157 (6), 135 (3), 121 (4), 107 (3), 95 (6), 81 (4), 69 (2).

Preparation of analog HJ, 1α,25-dihydroxy-3-epivitamin D$_3$ compound (9)

Sodium borohydride (38 mg, 1.0 mmol) was added to an ice cold solution of 1-oxo-25-hydroxy-3-epiprevitamin D$_3$ compound (7) (25 mg, 0.06 mmol) in MeOH (2 mL). After the reaction mixture was stirred for 1 h, tlc (75% ethyl acetate/hexane) showed complete disappearance of starting material. The mixture was extracted three times with ether and the ether extract was dried (MgSO$_4$) and then concentrated in vacuo. The crude product was purified by HPLC (10% iPrOH/hexane) to yield 17 mg (69%) of the previtamin 8. The latter dissolved in acetone (1 mL) was placed in a screw capped vial and heated for 4 h in a constant temperature bath set at 80° C. The reaction solution was concentrated in vacuo and then the residue was purified by HPLC (10% iPrOH/hexane) to afford after vacuum drying 15 mg (90%) of the vitamin 9 as a colorless oil.

$^1$H-NMR (300 MHZ): (CDCl$_3$) δ0.54 (3H, C$_{18}$—CH$_3$, s), 0.93 (3H, C$_{21}$—CH$_3$, d, J˜6.2 Hz), 1.21 (6H, C$_{26,27}$—CH$_3$, s), 2.43 (1H, H$_{4\beta}$, dd, J˜13.5 Hz, 5.5 Hz), 2.56 (1H, H$_{4\alpha}$, dd, J˜13.5 Hz, 2.9 Hz), 2.83 (1H, H$_{9\beta}$, dd, J˜11.8 Hz, 3.0 Hz), 4.0–4.1 (1H, H$_3$, m), 4.25–4.35 (1H, H$_1$, m), 5.0 (1H, H$_{19}$, narrow m), 5.29 (1H, H$_{19}$, narrow m), 6.02 and 6.43 (2H, H$_{6,7}$, AB pattern, J˜11.3 Hz).

$^{13}$C-NMR (75.5 MHZ): (CDCl$_3$) δ12.0, 18.8, 20.8, 22.2, 23.5, 27.7, 29.1, 29.2, 29.4, 36.1, 36.4, 40.5, 40.7, 44.4, 45.5, 45.9, 56.3, 56.5, 68.2, 71.1, 73.2, 112.9, 117.0, 125.6, 131.6, 143.2, 147.2.

IR: (CCl$_4$) v3018 (OH, br, s), 2965 (sp$^3$ CH, br, s), 1377 (s), 1215 (s), 668 (m) cm$^{-1}$. UV: (95% EtOH) λ$_{max}$ 264 nm (ε 16,900).

HRMS: m/z 416.3279 (calcd. for C$_{27}$H$_{44}$O$_3$, 416.3292).

MS: m/z 416 (19, M), 398 (28, M–H$_2$O), 380 (10, M–2H$_2$O), 330 (3), 285 (12), 251 (7), 227 (6), 152 (base, A-ring portion due to C$_{7,8}$-cleavage), 134 (73, m/z 152–H$_2$O), 107 (26), 95 (26), 81 (27), 55 (30).

Example 8

Chemical Synthesis of Analog HL

This example illustrates preparation of the analog HL, namely 1β,25-dihydroxyvitamin D$_3$. Analog HL was prepared according to Scheme C.

1-oxo-25-hydroxyprevitamin D$_3$ compound (11)

A solution (obtained by gently warming at 35° C. the originally obtained suspension) of 20 mg (0.05 mmol) of 1α,25-dihydroxyvitamin D$_3$ (10) in 4 mL of anhydrous CH$_3$CN was added dropwise to a well stirred suspension of Dess-Martin reagent (26 mg, 0.065 mmol) in CH$_3$CN (4 mL) under argon at room temperature. After 60 min stirring at room temperature, an additional 6 mg (0.3 molar equivalents) of oxidant was added in one portion and stirring was maintained for another 60 min. Ether (10 mL) was added and the resulting mixture was washed with a 1:1 mixture of saturated aqueous Na$_2$S$_2$O$_3$ and NaHCO$_3$ solution (20 mL). The organic layer was then dried (MgSO$_4$) and evaporated to dryness. The residue was purified by flash column chromatography on silica gel using hexane:ethyl acetate (1:3) to afford 17.5 mg (88% yield) of 1-oxo-25-hydroxyprevitamin D$_3$ (11). This substance was prepared in lower yield (<40%) using MnO$_2$.

$^1$H-NMR: (300 MHZ): (CDCl$_3$) δ0.72 (3H, C$_{18}$—CH$_3$, s), 0.97 (3H, C$_{21}$—CH$_3$, d, J˜6.6 Hz), 1.23 (6H, C$_{26,27}$—2CH$_3$, s), 1.80 (3H, C$_{19}$—CH$_3$, s), 4.17 (1H, H$_3$, m), 5.50 (1H, H$_9$, m), 6.04 and 6.14 (2H, H$_{6,7}$, AB pattern, J˜11.7 Hz).

$^{13}$C-NMR: (75 MHZ): (CDCl$_3$) δ11.2, 11.7, 18.7, 20.8, 23.3, 25.1, 28.4, 29.2, 29.3, 35.9, 36.1, 36.4, 38.8, 42.1, 44.4, 47.0, 50.6, 54.3, 67.0, 71.1, 71.2, 127.3, 132.5, 134.1, 136.4, 151.2, 197.7.

UV: (95% EtOH) λ$_{max}$ 240 nm (ε 15,000), 300 nm (ε 11,800); (ether) λ$_{max}$ 234 nm (ε 15,100), 288 nm (ε 11,200).

Preparation of analog HL, 1β,25-Dihydroxyvitamin D$_3$, compound (13)

Sodium borohydride (38 mg, 1.0 mmol) was reacted with 1-oxo-25-hydroxyprevitamin D$_3$ (11) (25 mg, 0.06 mmol) in MeOH (2 mL) and then worked up as described for the preparation of the 1α,3α-diastereomer 8. The product was purified by HPLC (10% iProH/hexane) to yield after vacuum drying 17 mg (69%) of the previtamin 12. The latter was dissolved in acetone (1 mL) and placed in a screw capped vial and heated in a constant temperature bath set at 80° C. for 4 h. It was concentrated in vacuo and purified by HPLC (80% EtOAc/hexane) to afford after vacuum drying 12 mg (70%) of the vitamin 13 as a colorless oil.

$^1$H-NMR (300 MHZ): (CDCl$_3$) δ0.55 (3H, C$_{18}$—CH$_3$, s), 0.94 (3H, C$_{21}$—CH$_3$, d, J˜5.7 Hz), 1.22 (6H, C$_{26,27}$—CH$_3$, s), 2.50 (2H, m), 2.83 (1H, m), 4.11 (1H, m), 4.36 (1H, m), 5.01 (1H, H$_{19}$, d, J˜1.5 Hz), 5.29 (1H, H$_{19}$, d, J˜1.2 Hz), 6.05 and 6.45 (2H, H$_{6,7}$, AB pattern, J˜11.4 Hz).

UV: (100% EtOH) λ$_{max}$ 264 nm (ε17,100).

Scheme D relates to analogs HQ and HR described in Examples 9 and 10.

Scheme D

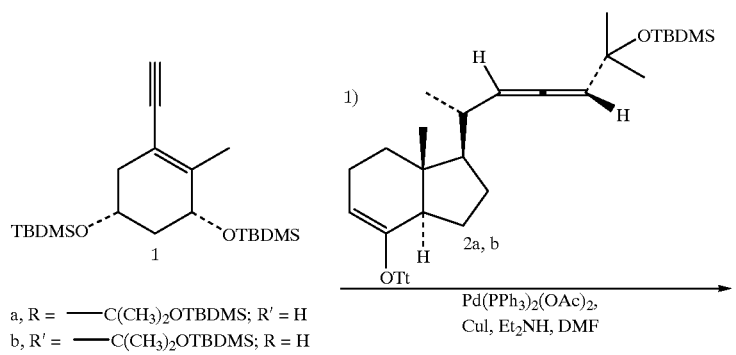

a, R = —C(CH$_3$)$_2$OTBDMS; R' = H
b, R' = —C(CH$_3$)$_2$OTBDMS; R = H

Pd(PPh$_3$)$_2$(OAc)$_2$, CuI, Et$_2$NH, DMF

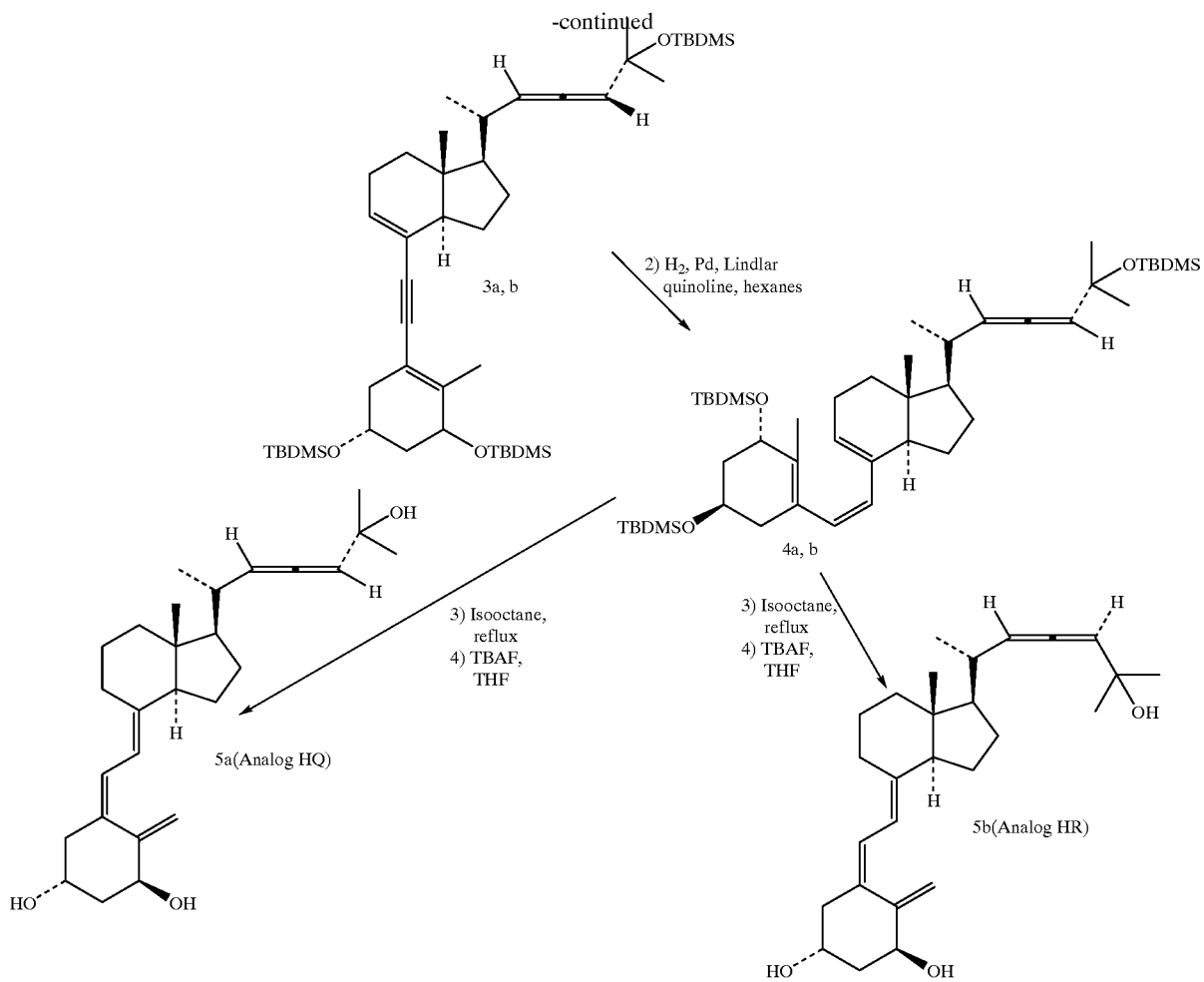

Chemical Synthesis of Analog HO

Thus example illustrates preparation of the analog HQ, namely (22S)-1α,25-Dihydroxy-22,23,23,24-tetradehydrovitamin $D_3$. Analog HO is prepared according to Scheme D.

Preparation of (22S)-1α,25-di(tert-butyldimethylsilyloxy)-6,7,22,23,23,24-hexadehydro-previtamin $D_3$ tert-butyldimethylsilyl ether, compound (3a)

Bis(triphenylphosphine)palladium(II)acetate (5.0 mg, 6.7 mmol) and copper(I) iodide (4.8 mg, 25.2 mmol) were added at ambient temperature to a mixture of enol triflate 2a (54.8 mg, 0.105 mmol), enyne 1 (48.0 mg, 0.126 mmol) in DMF (1.0 mL) and diethylamine (1.0 mL) under an argon atmosphere. The mixture was stirred at room temperature for 2.5 h after which time ether (10 mL) was added and the mixture washed with brine (3×10 mL). The organic layer was dried ($MgSO_4$), filtered and concentrated to afford a dark brown residue. The crude product was passed down a short silica gel column (15% ethyl acetate/hexanes) followed by HPLC separation (Rainin Dynamax, 1.0×25 cm, 8 µm, 1% ethyl acetate/hexanes) to afford after drying, spectroscopically homogeneous dienyne 3a (59 mg, 75%) as a colorless oil.

$^1$H-NMR: δ_0.06 (6H, Si—$Me_2$, s), 0.07 (6H, Si—$Me_2$, s), 0.09 (6H, Si—$Me_2$), 0.72 (3H, $C_{18}$—Me, s), 0.85 (9H, t-Bu, s), 0.88 (9H, t-Bu, s), 0.89 (9H, t-Bu, s), 1.09 (3H, $C_{21}$—Me, d, J⁻6.6 Hz), 1.30 (3H, $C_{26,27}$—$CH_3$, s), 1.31 (3H, $C_{26,27}$—$CH_3$, s), 1.90 (3H, $C_{19}$—Me, br s), 4.09 (1H, $H_3$, broad m, W⁻15 Hz), 4.19 (1H, $H_1$, m), 5.18 (1H, $H_{22}$, dd, J⁻6.6 Hz, 6.6 Hz), 5.28 (1H, $H_{24}$, dd, J⁻6.6 Hz, 1.8 Hz), 5.97 (1H, $H_9$, narrow m).

Preparation of (22S)-1α,25-Di(tert-butyldimethylsilyloxy)-22,23,23,24-tetradehydro-previtamin $D_3$ tert-butyldimethylsilyl ether, compound (4a)

A mixture of dienyne 3a (10.0 mg, 0.013 mmol), quinoline (75 µL, 0.17 M in hexanes, 0.013 mmol) and Lindlar catalyst (21 mg) in hexanes (3.5 mL) was stirred under an atmosphere of hydrogen for 1 h. The mixture was filtered through a short pad of silica gel and the residue concentrated to afford a colorless oil. The crude product was purified by HPLC (Rainin Dynamax, 1.0×25 cm, 8 µm, 0.1% ethyl acetate/hexanes) to afford after vacuum drying, the spectroscopically pure previtamin 4a (8.0 mg, 81%) as a colorless oil.

$^1$H-NMR: δ_0.05 (3H, Si—Me, s), 0.06 (3H, Si—Me, s), 0.07 (6H, Si—$Me_2$, s), 0.09 (6H, Si—$Me_2$, s), 0.71 (3H, $C_{18}$—Me, s), 0.85 (9H, t-Bu, s), 0.886 (9H, t-Bu, s), 0.895 (9H, t-Bu, s), 1.09 (3H, $C_{21}$—Me, d, J⁻6.6 Hz), 1.30 (3H, $C_{26,27}$—Me, s), 1.31 (3H, $C_{26,27}$—Me, s), 1.65 (1H, $C_{19}$—Me, br s), 4.01–4.10 (1H, $H_3$, m), 4.11 (1H, $H_1$, br s), 5.17 (1H, $H_{22}$, dd, J⁻6.9 Hz, 6.9 Hz), 5.27 (1H, $H_{24}$, dd, J⁻6.6 Hz, 1.8 Hz), 5.55 (1H, $H_9$, narrow m), 5.73 and 5.88 (2H, $H_6$ and $H_7$, AB pattern, J⁻12.0 Hz).

Preparation of analog HQ, (22S)-1α,25-dihydroxy-22,23,23,24-tetradehydrovitamin $D_3$, compound (5a)

A solution of previtamin 4a (12.0 mg, 15.9 mmol) in isooctane (8.0 mL) was refluxed (~100° C.) under an argon atmosphere for 2.4 h. The solvent was removed under vacuum to afford a colorless residue, which was determined to be a 88:12 inseparable mixture of vitamin and previtamin. A solution of this mixture in THF (1.0 mL) was treated with tetra-butylammonium fluoride (275 μL, 1.0 M in THF, 0.275 mmol) at room temperature for 15 h, protected from the light. The reaction was quenched by the addition of brine (2 mL) and the mixture was extracted with ethyl acetate (4×2 mL). The combined organic extracts were dried ($MgSO_4$) and concentrated and the crude product passed through a short pad of silica gel. Purification was effected by HPLC (Rainin Dynamax, 1×25 cm, 8 μm, 4 mL/min, 100% ethyl acetate) to afford after drying 4.7 mg (71%) of the vitamin (5a) as a viscous colorless oil.

$^1$H-NMR: δ_0.57 (3H, $C_{18}$—Me, s), 1.08 (3H, $C_{21}$—Me, d, J~6.6 Hz), 1.34 (6H, $C_{26,27}$—2$CH_3$, s), 2.32 (1H, $H_{4\beta}$, dd, J~13.2 Hz, 6.0 Hz), 2.60 (1H, $H_{4\alpha}$, dd, J~13.2 Hz, 3.0 Hz), 2.83 (1H, $H_{9\beta}$, dd, J~11.7 Hz, 3.0 Hz), 4.23 (1H, $H_3$, m, W~20 Hz), 4.43 (1H, $H_1$, m, W~12 Hz), 5.00 (1H, $H_{19Z}$, narrow m), 5.33 (1H, $H_{19E}$, narrow m), 5.28–5.35 (2H, $H_{22}$ and $H_{24}$, m, partially obscured by $H_{19E}$), 6.02 and 6.38 (2H, $H_6$ and $H_7$, AB pattern, J~11.2 Hz).

Example 10

Chemical Synthesis of Analog HR

This example illustrates preparation of the analog HR, namely (22R)-1α,25-dihydroxy-22,23,23,24-tetradehydrovitamin $D_3$. Analog HR was prepared according to Scheme D.

Preparation of (22R) -1α,25-di(tert-butyldimethylsilyloxy)-6,7,22,23,23,24-hexadehydro-previtamin $D_3$ tert-butyldimethylsilyl ether, compound (3b)

Bis(triphenylphosphine)palladium(II) acetate (6.0 mg, 8.1 mmol) and copper(I) iodide (5.8 mg, 30.4 mmol) were added at ambient temperature to a mixture of enol triflate 2b (64 mg, 0.123 mmol), enyne 1 (56 mg, 0.147 mmol) in DMF (1.2 mL) and diethylamine (1.2 mL) under an argon atmosphere. The mixture was stirred at room temperature for 2.5 h after which ether (10 mL) was added and the mixture washed with brine (3×10 mL). The organic layers was dried ($MgSO_4$), filtered and concentrated to afford a dark brown residue. Purification was effected by a short path flash chromatography (silica gel, 15% ethyl acetate/hexanes) followed by HPLC separation (Rainin Dynamax, 1.0×25 cm, 8 μm, 1% ethyl acetate/hexanes) to afford after drying, spectroscopically homogeneous dienyne 3b (86 mg, 93%) as a colorless oil.

$^1$H-NMR: δ_0.06 (6H, Si—$Me_2$, s), 0.07 (6H, Si—$Me_2$, s), 0.09 (6H, Si—$Me_2$, s), 0.72 (3H, $C_{18}$—Me, s), 0.85 (9H, t-Bu, s), 0.88 (9H, t-Bu, s), 0.89 (9H, t-Bu, s), 1.09 (3H, $C_{21}$—Me, d, J~6.6 Hz), 1.29 (3H, $C_{26,27}$—$CH_3$, s), 1.30 (3H, $C_{26,27}$—CH, s), 1.89 (3H, $C_{19}$—Me, br s), 4.1 (1H, $H_3$, br m), 4.19 (1H, $H_1$, m), 5.15 (1H, $H_{22}$, dd, J~6.6 Hz, 6.6 Hz), 5.27 (1H, $H_{24}$, dd, J~6.6 Hz, 1.8 Hz), 5.97 (1H, $H_9$, narrow m).

Preparation of (22R)-1α,25-di(tert-butyldimethylsilyloxy) -22,23,23,24-tetradehydro-previtamin $D_3$ tert-butyldimethylsilyl ether, compound (4b)

A mixture of dienyne 3b (10.0 mg, 0.013 mmol), quinoline (80 μL, 0.17 M in hexanes, 0.013 mmol) and Lindlar catalyst (20 mg) in hexanes (3.0 mL) was stirred under an atmosphere of hydrogen for 40 min. The mixture was filtered through a short pad of silica gel and the residue concentrated to afford after drying, a colorless oil. HPLC separation (Rainin Dynamax, 1.0×25 cm, 8 μm, 0.1% ethyl acetate/hexanes) afforded the spectroscopically pure previtamin 4b (7.0 mg, 70%) as a colorless oil.

$^1$H-NMR: δ_0.05 (3H, Si—Me, s), 0.06 (3H, Si—Me, s), 0.07 (6H, Si—$Me_2$, s), 0.09 (6H, Si—$Me_2$, s), 0.71 (3H, $C_{18}$—Me, s), 0.85 (9H, t-Bu, s), 0.886 (9H, t-Bu, s), 0.894 (9H, t-Bu, s), 1.09 (3H, $C_{21}$—Me, d, J~6.6 Hz), 1.29 (3H, $C_{26,27}$—$CH_3$, s), 1.31 (3H, $C_{26,27}$—$CH_3$, s), 1.65 (3H, $C_{19}$—Me, broad s), 4.01–4.10 (1H, $H_3$, m), 4.11 (1H, $H_1$, broad s), 5.14 (1H, $H_{22}$, dd, J~6.6 Hz, 6.6 Hz), 5.27 (1H, $H_{24}$, dd, J~6.6 Hz, 2.1 Hz), 5.54 (1H, $H_9$, narrow m), 5.72 and 5.90 (2H, $H_6$ and $H_7$, AB pattern, J~12.0 Hz).

Preparation of analog HR, (22R)-1α,25-dihydroxy-22,23,23,24-tetradehydrovitamin $D_3$, compound (5b)

A solution of previtamin 4b (15 mg, 19.9 mmol) in isooctane (10 mL) was refluxed (~100° C.) for 2 h under an argon atmosphere. The solvent was removed under vacuum to give a colorless residue, which after HPLC separation (Rainin Dynamax, 0.1% ethyl acetate/hexanes) afforded a 9:1 mixture of vitamin and previtamin. The mixture was dissolved in THF (1 mL) and treated with tetrabutylammonium fluoride (273 μL, 1.0 M in THF, 0.273 mmol) at room temperature for 15 h, protected from the light. The reaction was quenched by the addition of brine (2 mL) and then the mixture was extracted with ethyl acetate (4×2.0 mL). The combined organic extracts were dried ($MgSO_4$), filtered and concentrated. Purification was effected by short column flash chromatography (silica gel, 100% ethyl acetate) followed by HPLC separation (Rainin Dynamax, 100% ethylacetate) to afford after vacuum drying vitamin 5b (5.4 mg, 66%) as a colorless foam.

$^1$H-NMR: δ_0.57 (3H, $C_{18}$—Me, s), 1.09 (3H, $C_{21}$—Me, d, J~6.6 Hz), 1.34 (6H, $C_{26,27}$—2$CH_3$, s), 2.32 (1H, $H_{4\beta}$, dd, J~13.2 Hz, 6.0 Hz), 2.60 (1H, $H_{4\alpha}$, dd, J~13.2 Hz, 3.0 Hz), 2.83 (1H, $H_{9\beta}$, dd, J~12.0 Hz, 3.0 Hz), 4.23 (1H, $H_3$, m, W~20 Hz), 4.43 (1H, $H_1$, m, W~12 Hz), 5.00 (1H, $H_{19Z}$, s), 5.33 (1H, $H_{19E}$, s), 5.26–5.35 (2H, $H_{22}$ and $H_{24}$, m, partially obscured by $H_{19E}$), 6.02 and 6.38 (2H, $H_6$ and $H_7$, AB pattern, J~11.2 Hz).

Scheme E relates to the analog HS described in Example 11.

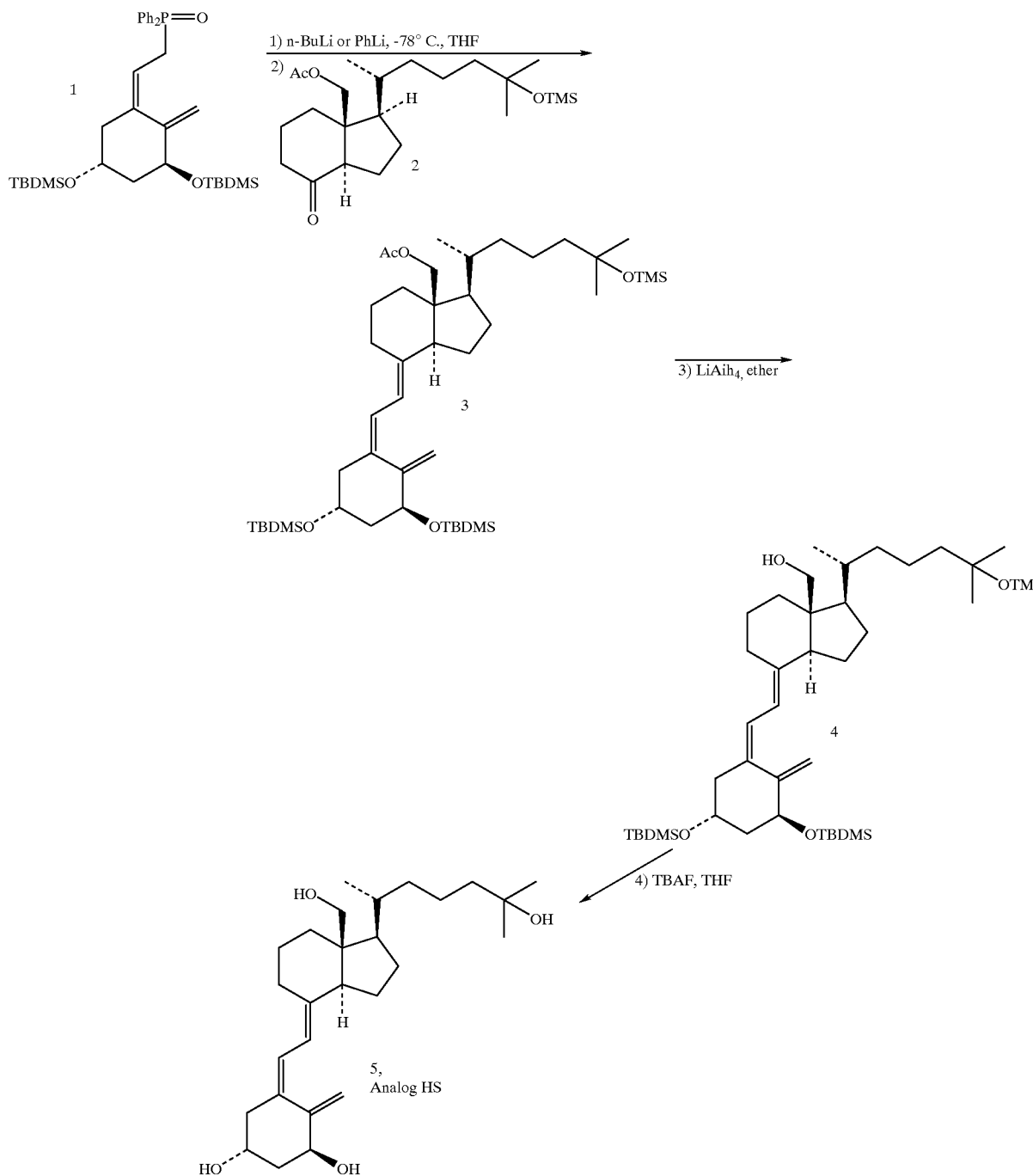

Scheme E

Example 11

Chemical Synthesis of Analog HS

This example illustrates preparation of the analog HS, namely 1α,18,25(OH)$_2$D$_3$, as seen in Scheme E.

Preparation of 18-acetoxy-25-trimethylsilyloxy-1α-tert-butyldimethylsilyloxy-vitamin D$_3$ tert-butyldimethylsilyl ether, compound (3)

A solution of A-ring phosphine oxide 1 (122 mg, 0.21 mmol) in dry THF (3 mL) was treated with n-butyllithium (0.14 mL, 0.21 mmol, 1.55 M in hexanes) and then with CD-ring ketone 2 (57 mg, 0.14 mmol) in dry THF (2.2 mL). After work up, there was obtained 81 mg (83%) of the protected vitamin 3 of sufficient purity for the next step.

$^1$H-NMR: (CDCl$_3$) δ0.07 (12H, Si—Me,series of s), 0.10 (9H, TMS), 0.87 (9H, t-Bu, s), 0.89 (9H, t-Bu, s), 1.03 (3H, C$_{21}$—CH$_3$, d, J~4.0 Hz), 1.20 (6H, C$_{26,27}$—CH$_3$, s), 2.01 (3H, Ac, s), 2.87 (1H, H$_{9\beta}$, d, J~12.8 Hz), 3.86 (2H, 2H$_{18}$, s), 4.1–4.3 (1H, H$_3$, m), 4.37 (1H, H$_1$, apparent t, J~4.9 Hz), 4.86 (1H, $H_{19}$, d, J~1.9 Hz), 5.18 (1H, $H_{19}$, br s), 6.03 and 6.19 (2H, $H_{6,7}$, AB pattern, d, J~11.1 Hz).

Preparation of 18-hydroxy-25-trimethylsilyloxy-1α-tert-butyldimethylsilyloxy-vitamin $D_3$ tert-butyldimethylsilyl Ether (4)

Compound 3 (139 mg, 1.8 mmol) was dissolved in anhydrous ethyl ether (0.2 mL) and was added dropwise to a solution of $LiAlH_4$ (21 mg, 5.4 mmol) in ether (0.5 mL). The reaction mixture was stirred for 30 minutes, by which time the solution had become viscous and an additional 0.2 mL of ether was added. After stirring for 20 minutes, the reaction mixture was quenched with ethyl acetate (1 mL) and then filtered through a sintered glass funnel. The grey solid was washed with ethyl acetate (5 mL) and the combined filtrate concentrated. The crude residue was purified by flash chromatography (20% ethyl acetate/hexanes) to afford, after vacuum drying, 102 mg (78%) of the protected alcohol precursor, compound 4.

The analytical data for the precursor is:

$^1$H-NMR (300 MHZ): ($CDCl_3$) δ0.06 (12H, Si—$CH_3$, s), 0.10 (9H, TMS, s), 0.87 (9H, t-Bu, s), 0.89 (9H, t-Bu, s), 1.04 (3H, $C_{21}$, $CH_3$, d, J~6.3 Hz), 1.20 (6H $C_{26,27}$—$CH_3$, s), 0.9–2.5 (remaining ring and side chain hydrogens, series of m), 2.88 (1H, br d, J~11.8 Hz), 3.44 (1H, $H_{18}$, d, J~11.5 Hz), 3.53 (1H, $H_{18}$, d, J~11.5 Hz), 4.18 (1H, $H_3$, m), 4.37 (1H, $H_1$, m), 4.84 (1H $H_{19}$, br s), 5.18 (1H, $H_{19}$, br s), 6.04 and 6.22 (2H, $H_{6,7}$ AB pattern, d, J~11.1 Hz).

$^{13}$C-NMR (75.5 MHZ): ($CDC_3$) δ−5.1, −4.8, −4.7, 2.6, 18.1, 18.2, 19.3, 20.7, 22.0, 23.9, 25.8, 25.9, 27.6, 28.8, 29.8, 30.0, 35.7, 36.1, 36.6, 44.8, 45.3, 46.0, 49.7, 55.3, 56.9, 61.5, 67.5, 72.0, 74.1, 111.3, 118.1, 122.8, 135.9, 141.0, 148.3.

IR: ($CCl_4$) v 3500 (OH, br), 2960 (C—H, s), 2930 (C—H s), 2860 (C—H, m), 1650 (w), 1470 (w), 1360 (w), 1250 (s), 1090 (s), 1045 (s), 910 (m), 840 (s) $cm^{-1}$.

UV: (95% EtOH) $\lambda_{max}$ 264 nm (ε18,000): $\lambda_{min}$ 232 nm (ε10,900).

Anal. calcd. for $C_{42}H_{80}O_4Si_3$: 68.79; H, 11.00. Found: C, 68.74; H, 11.17.

Preparation of 1α,18,25(OH)$_2D_3$, compound 5

The analog HS (5) was prepared by adding tetra-n-butyl-ammonium fluoride (2.16 μL, 0.216 mmol, 1 M in THF) to a solution of the protected alcohol precursor compound 4 (18.1 mg, 0.024 mmol) in anhydrous THF (2 mL). The mixture was stirred for 20 hours at room temperature, then concentrated to dryness. The resulting crude material was directly flash chromatographed through a short column of silica gel (EtOAc) and then purified by HPLC (Rainin Dynamax, 1.0×25 cm, 8 μm silica column, EtOAc) to give, after vacuum drying, the analog HS (5, 7 mg, 70%) as a white foam.

The analytical data for the analog HS (5) is:

$^1$H-NMR (300 MHZ): ($CD_3OD$) δ1.07 (3H, $C_{21}$—$CH_3$, d, J~6.4 Hz), 1.16 (6H, $C_{26,27}$—$CH_3$, s), 1.0–2.2 (remaining ring and side chain hydrogens, series of m), 2.24 (1H, dd, J~13.2 Hz, 7.2 Hz), 2.51 (2H, br d, J~13.0 Hz), 2.91 (1H, br d, J~11.2 Hz), 3.35 (2H, $H_{18}$, d, J~11.8 Hz), 3.41 (1H, $H_{18}$, d, J~11.8 Hz), 4.10 (1H, $H_3$, m), 4.34 (1H, $H_1$, t, J~5.6 Hz), 4.87 (1H, $H_{19}$, s), 5.28 (1H, $H_{19}$, s), 6.06 and 6.32 (2H, $H_{6,7}$, AB pattern, d, J~11.1 Hz).

UV: (95% EtOH) $\lambda_{max}$ 264 nm (ε18,100): $\lambda_{min}$ 230 nm (ε10,300).

HRMS: m/z 432.3242 (calcd. for $C_{27}H_{44}O_4$, 432.3241). MS: m/z 432 (1, M), 414 (4, M–$H_2O$), 396 (1, M–$2H_2O$), 257 (2), 171 (3), 152 (1, A-ring fragment due to $C_{7,8}$ cleavage), 134 (8, 152–$H_2O$), 105 (6), 91 (10), 79 (17), 69 (20), 59 (base).

Scheme F relates to the analog IB described in Example 12.

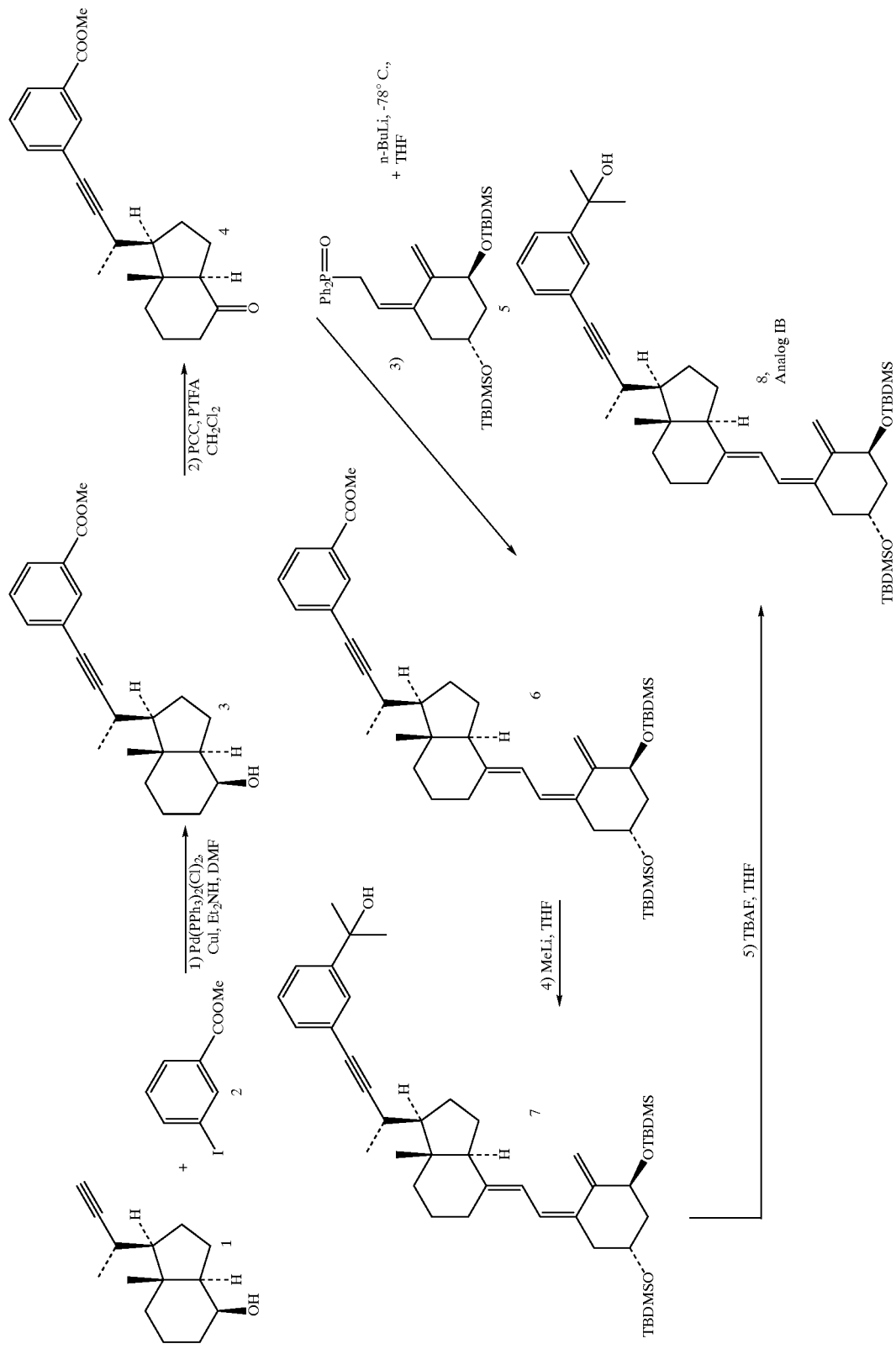

Example 12

Chemical Synthesis of Analog IB

This example illustrates preparation of the analog IB, namely 23-(m-dimethylhydroxymethyl)phenyl)-22-yne-24,25,26,27-tetranor-1α(OH)D$_3$, as seen in Scheme F.

Preparation of 23-[3-(1'-methyl-1'-hydroxyethyl)phenyl]-22,23-tetradehydro-24,25,26,27-tetranor-1α-OH—D$_3$ In step 1, 1 and 2 are reacted in the presence of palladium (0) resulting in 3, which was obtained pure by flash chromatography using the solvent 20% ethyl acetate in hexane.

In step 2, 55 mg of the product of step 1 was reacted with 183 mg pyridinium chlorochromate (PDC), 12 mg pyridinium trifluoroacetate (PTFA) and 100 mL CH$_2$Cl$_2$ according to a standard procedure. The reaction was carried out at room temperature for 5 hours. The resulting black mixture was filtered and washed with CH$_2$Cl$_2$ and extracted with ethyl acetate to produce a pale yellow oil. This oil was flash chromatographed to produce pure 4.

In step 3, the product of step 2 was reacted with 70 mg phosphine oxide 5, 82 μL n-butyllithium and 35 mg of the CD ketone 4 in 2 mL of a solution of THF. The n-butyllithium was added dropwise to the solution of phosphine oxide in THF. The resulting orange colored solution was stirred at −78° C. for 10 minutes and the CD ring ketone in THF was added dropwise. The reaction mixture was stirred at −78° C. for 4 hours. At this point the solution turned pale yellow. The solution was quenched with H$_2$O, extracted with ethyl acetate and dried over Na$_2$SO$_4$. The solvent was vacuum evaporated and the resulting product purified by flash chromatography.

In step 4, 10 mg of compound 6 reacted with 53 μL MeLi in 2 mL THF. To the solution of 6 in THF at room temperature was added MeLi dropwise. The mixture was stirred at room temperature for 1 hour, quenched with H$_2$O. The resulting ether extract was washed with H$_2$O and dried. The product 7 was then isolated.

In step 5, 10 mg of the product 7 was dissolved in 1 mL THF. 60 μL TBAF (1 M in THF) was added dropwise and the solution stirred at room temperature overnight. The resulting mixture was passed through a short volume of Al$_2$O$_3$ (neutral) and extracted with ethyl acetate. The resulting product was identified as compound 8 (Analog IB) by NMR and UV.

Scheme G relates to analogs JM, JN, JO and JP described in Examples 13–16.

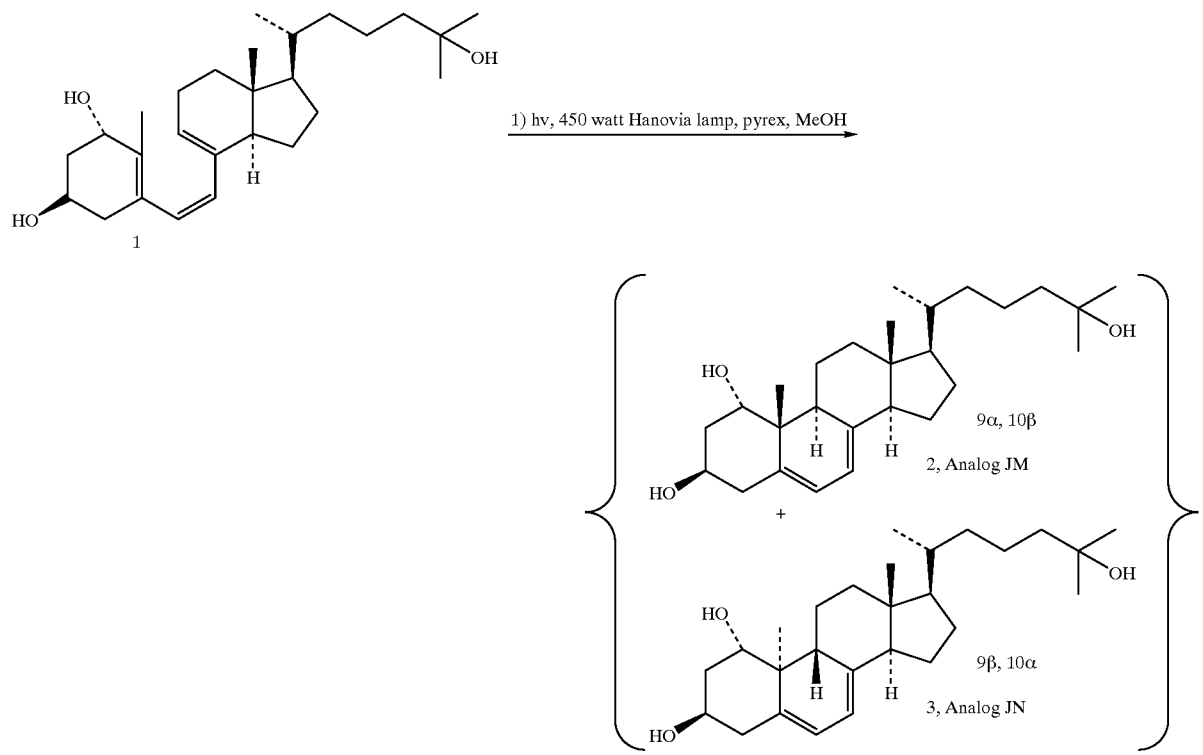

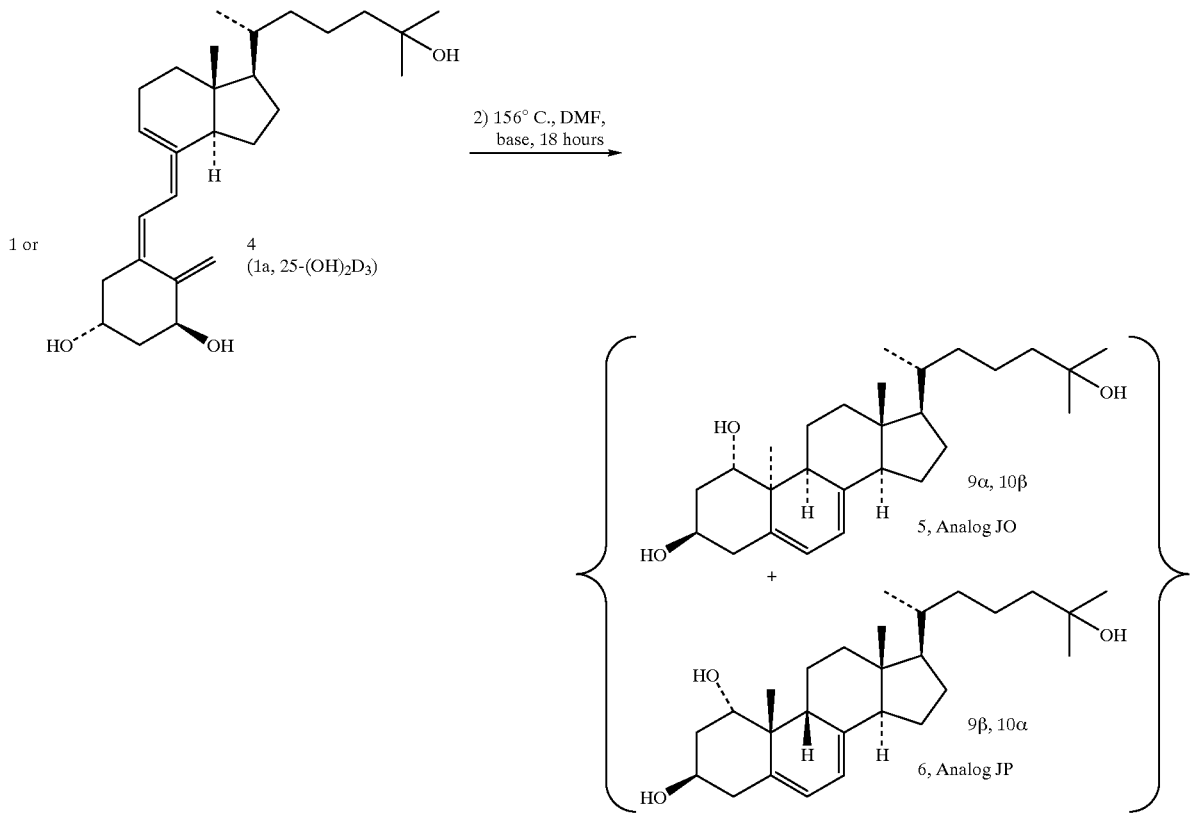

Example 13

Chemical Synthesis of Analog JM

This example illustrates preparation of the analog JM, namely 1α,25-Dihydroxy-7-dehydrocholesterol, 9α,10β-isomer, as seen in Scheme G.

After 1α,25-dihydroxyprevitamin D$_3$ (1) (120 mg) in methanol was saturated with argon for 1 h, the solution was photochemically irradiated (Hanovia 450 watt medium pressure mercury lamp, pyrex filter, λ>300 nm) for 3 h at room temperature. The solution was concentrated and subjected to HPLC (Raining Microsorb, 5 μm silica, 10 mm×25 cm, 11% isopropanol/hexanes) to afford in order of elution JM (2) (9.1 mg, 7.6%), JN (3) (15.0 mg, 12.5%) and the starting previtamin (10.6 mg, 8.8%). Analysis of the crude mixture by $^1$H-NMR spectroscopy showed the ratio of JN:JM to be 3:1. Data for analog JM:

$^1$H-NMR (300 MHZ): (CDCl$_3$) δ0.63 (3H, C$_{18}$—CH$_3$, s), 0.95 (3H, C$_{19}$—CH$_3$, s), 0.96 (3H, C$_{21}$—CH$_3$, d, J~5.6 Hz), 1.22 (6H, C$_{26,27}$—CH$_3$, s), 0.85–2.2 (remaining ring and side chain hydrogens, various m), 2.35 (1H, apparent t, J~12.7 Hz), 2.55 (1H, d with fine structure, J~14.2 Hz), 2.70 (1H, m), 3.77 (1H, H$_1$, br s), 4.07 (1H, H$_3$, m), 5.38 (1H, H$_{6\ or\ 7}$, ddd, J~5.5 Hz, 2.8 Hz, 2.8 Hz), 5.73 (1H, H$_{7\ or\ 6}$, dd, J~5.5 Hz, 2.2 Hz).

13C-NMR (75.5 MHZ): (CDCl$_3$) δ11.9, 16.3, 18.8, 20.8, 20.9, 23.0, 28.1, 29.2, 29.4, 36.1, 36.4, 38.0, 38.5, 39.2, 40.0, 43.1, 44.4, 54.7, 55.8, 65.5, 71.1, 73.0, 115.2, 122.1, 141.4.
UV: (100% EtOH) λ$_{max}$ 294 nm (ε8,400), 282 nm (ε13,400), 272 nm (ε12,800); λ$_{min}$ 290 nm (ε7,800), 278 nm (ε11,500); λ$_{sh}$ 264 nm (ε9,600).

HRMS: (CI, CH$_4$) m/z 417.3365 (calcd. for C$_{27}$H$_{44}$O$_3$ plus H, 417.3370).

MS: (CI, CH$_4$) m/z 417 (28, MH), 400 (67), 381 (31), 354 (11), 338 (6), 323 (6), 297 (4), 267 (4), 251 (8), 225 (10), 211 (10), 197 (11), 171 (19), 157 (15), 119 (12), 105 (15), 91 (14), 81 (14), 69 (27), 59 (base).

Example 14

Chemical Synthesis of Analog JN

This example illustrates preparation of the analog JN, namely analog JN, 1α,25-Dihydroxylumisterol, 9β,10α-Isomer (3), as seen in Scheme G.

Analog JN (3) is prepared similarly to and accompanies preparation of the analog JM (2) in the synthesis described in Example 13. The spectroscopic data for JN are as follows.

$^1$H-NMR (300 MHZ): (CDCl$_3$) δ0.61 (3H, C$_{18}$—CH$_3$, s), 0.78 (3H, C$_{19}$—CH$_3$, s), 0.91 (3H, C$_{21}$—CH$_3$, d, J~5.2 Hz), 1.21 (6H, C$_{26,27}$—CH$_3$, s), 0.70–2.30 (remaining ring and side chain hydrogens, various m), 2.50 (2H, m), 4.10 (1H, H$_1$, dd, J~9.2 Hz, 4.8 Hz), 4.14 (1H, H$_3$, dd, J~3.0 Hz, 3.0 Hz), 5.45 (1H, H$_{6\ or\ 7}$, m), 5.75 (1H, H$_{7\ or\ 6}$, dd, J~5.1 Hz, 1.7 Hz).

$^{13}$C-NMR (75.5 MHZ): (CDCl3) δ7.4, 18.3, 18.5, 20.9, 21.7, 22.6, 28.8, 29.2, 29.4, 29.7, 36.2, 37.5, 38.9, 39.5, 41.4, 43.9, 44.4, 46.2, 49.5, 57.3, 66.2, 71.1, 75.8, 115.5, 123.6, 137.2, 142.2.

UV: (100% EtOH) λ$_{max}$ 282 nm (ε 6,900), 274 nm (ε 7,300); λ$_{sh}$ 294 nm (ε 3,900), 264 nm (ε 5,900).

HRMS: m/z (CI, CH$_4$) 417.3365 (calcd. for C$_{27}$H$_{44}$O$_3$ plus H, 417.3370).

HS (CI, CH$_4$): m/z 417 (86, MH), 400 (base), 382 (60), 366 (13), 343 (8), 325 (6), 311 (5), 287 (15), 269 (13), 251 (9), 227 (13), 213 (9), 174 (46), 157 (21), 143 (14), 119 (7), 105 (8), 95 (8), 81 (8), 69 (14), 59 (38).

Example 15

Chemical Synthesis of Analog JO

This example illustrates preparation of the analog JO, namely 1α,25-dihydroxypyrocholecalciferol, 9α,10α-isomer (5), as seen in Scheme G.

An argon flushed solution of 1α,25-dihydroxyprevitamin D$_3$ (1) (54.2 mg; or 1α,25-dihydroxyvitamin D$_3$ (2) may be used) dissolved in DMF (15 mL) containing a drop of 2,4,6-trimethylpyridine was heated in a screw cap vial (156° C.) for 18 h. The cooled solution was then concentrated and the crude residue was purified by HPLC (Rainin Microsorb, 5 μm silica, 10 mm×25 cm, 11% isopropanol/hexanes) to afford in order of elution analog JP (6) (7.3 mg, 13.5%), analog JO (5) (20.1 mg, 37.1%) and 1α,25-dihydroxyvitamin D$_3$ (2.1 mg, 3.9%). Analysis of the crude mixture by $^1$H-NMR spectroscopy showed the ratio of JO to JP to be 3:1.

Data for analog JO:

$^1$H-NMR (300 MHZ): (CDCl$_3$) δ0.53 (3H, C$_{18}$—CH$_3$, s), 0.90 (3H, C$_{21}$—CH$_3$, d, J~6.0 Hz), 1.02 (3H, C$_{19}$—CH$_3$, s), 1.21 (6H, C$_{26,27}$—CH$_3$, s), 0.80–2.05 (remaining ring and side chain hydrogens, various m), 2.15 (1H, dd, J~12.6 Hz, 7.6 Hz), 2.26 (1H, d with fine structure, J~6.1 Hz), 2.54 (1H, br, d, J~6.1 Hz), 4.16 (1H, H$_3$, dddd, J~2.8 Hz, 2.8 Hz, 2.8 Hz, 2.8 Hz), 4.31 (1H, H$_1$, dd, J~12.0 Hz, 4.6 Hz), 5.34 (1H, H$_6$ or 7, d, J~5.7 Hz), 5.61 (1H, H$_{7\ or\ 6}$, dd, J~5.7 Hz, 2.5 Hz).

$^{13}$C-MNR (75.5 MHZ): (CDCl$_3$) δ12.2, 17.4, 18.7, 20.8, 20.9, 26.0, 28.5, 29.2, 29.4, 29.7, 36.2, 36.4, 37.6, 38.0, 41.1, 44.4, 48.7, 50.6, 56.4, 57.6, 66.7, 66.9, 71.1, 111.7, 121.1, 134.8, 140.1.

UV: (100% EtOH) λ$_{max}$ 286 nm (ε 9,400), 276 nm (ε 9,300); λ$_{min}$ 280 nm (ε 8,800); ε$_{sh}$ 296 nm (ε 5,700), 266 nm (ε 7,000).

HRMS: (CI, CH$_4$) m/z 417.3366 (calcd. for C$_{27}$H$_{44}$O$_3$ plus H, 417.3370). MS: (CI, CH$_4$) m/z 417 (49, MH), 400 (base), 382 (54), 364 (9), 343 (4), 326 (4), 312 (3), 287 (4), 269 (4), 251 (4), 227 (6), 213 (4), 197 (6), 157 (12), 143 (8), 111 (9), 95 (13), 81 (17), 69 (24), 59 (85).

Example 16

Chemical Synthesis of Analog JP

This example illustrates preparation of analog JP, namely JP, 1α,25-dihydroxyisopyrocholecalciferol, 9β,10β-isomer (6), as seen in Scheme G.

Analog JP (6) accompanies preparation of JO (5) in the synthesis described in Example 15. The spectroscopic data for JP follows.

Data for analog JP:

$^1$H-NMR (300 MHZ): (CDCl$_3$) δ0.65 (3H, C$_{18}$—CH$_3$, s), 0.92 (3H, C$_{21}$—CH$_3$, d, J~5.3 Hz), 1.21 (6H, C$_{26,27}$—CH$_3$, s), 1.30 (3H, C$_{19}$—CH$_3$, s), 0.80–2.08 (remaining ring and side chain hydrogens, various m), 2.39–2.66 (3H, overlapping m), 3.71 (1H, H$_1$, dd, J~2.8 Hz, 2.8 Hz), 3.94 (1H, H$_3$, dddd, J~10.9 Hz, 10.9 Hz, 5.5 Hz, 5.5 Hz), 5.34 (1H, H$_{6\ or\ 7}$, ddd, J~5.5 Hz, 2.7 Hz, 2.7 Hz), 5.95 (1H, H$_{7\ or\ 6}$, d, J~5.5 Hz).

$^{13}$C-NMR (75.5 MHZ): (CDCl$_3$) δ18.3, 18.6, 20.4, 20.9, 22.4, 26.1, 28.8, 29.2, 29.3, 29.7, 36.1, 37.5, 39.2, 41.2, 42.0, 43.5, 44.4, 49.2, 57.3, 69.8, 71.1, 74.5, 115.2, 122.8, 135.5, 142.8.

UV: (100% EtOH) λ$_{max}$ 286 nm (ε 7,800), 278 nm (ε 7,900); λ$_{sh}$ 296 nm (ε 5,200), 270 nm (ε 6,500).

HRMS: (CI, CH$_4$) m/z 417.3351 (calcd. for C$_{27}$H$_{44}$O$_3$ plus H, 417.3370).

MS: (CI, CH$_4$) m/z 417 (36, MH), 400 (base), 382 (51) 364 (12), 342 (4), 312 (3), 288 (6), 270 (10), 252 (10), 215 (9), 197 (6), 171 (11), 157 (7), 143 (5), 123 (6), 105 (13), 91 (8), 81 (8), 69 (17), 59 (40).

Scheme H relates to analogs JR, JS, JV and JW described in Examples 17–20.

Scheme H

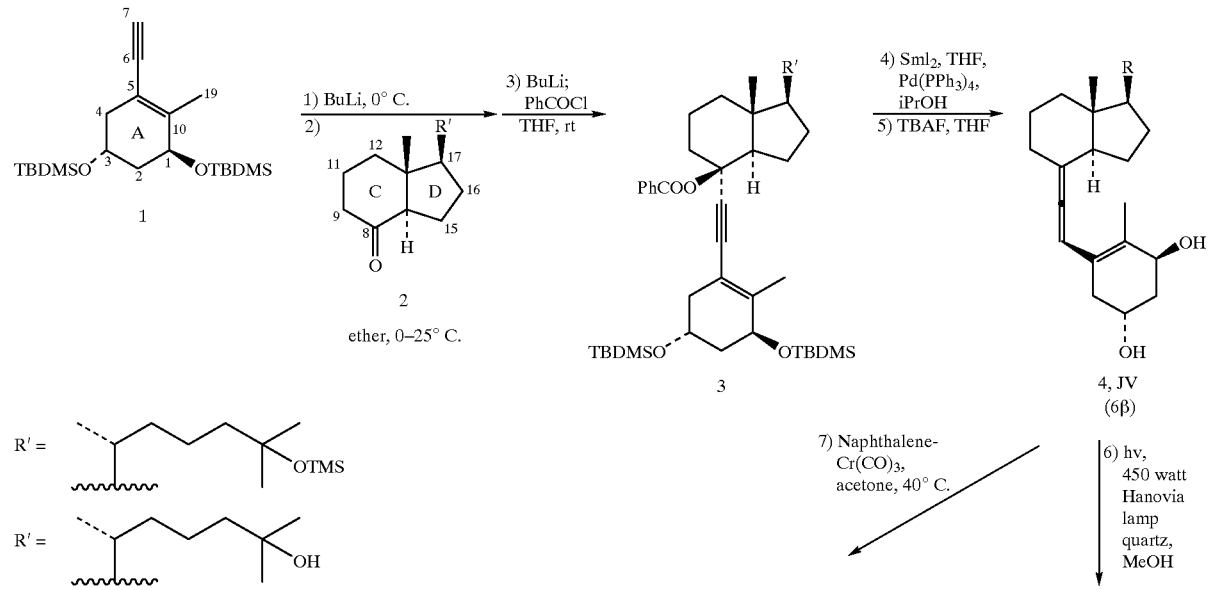

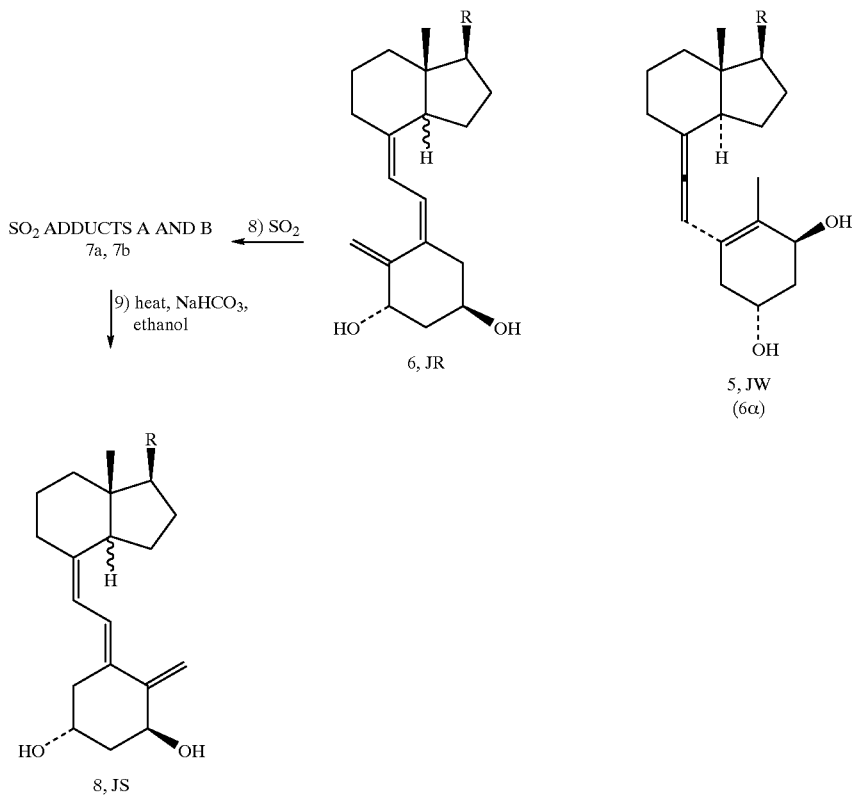

Example 17

Chemical Synthesis of Analog JR

This example illustrates preparation of analog JR, namely 7,8-cis-1α,25-dihydroxyvitamin $D_3$ as seen in Scheme H.

Preparation of analog JR, 7,8-cis-1α,25-dihydroxyvitamin $D_3$

To the vinylallene trial 4 (19.7 mg, 0.047 mmol), and ($\eta^6$-naphthalene)tricarbonylchromium (14.7 mg, 0.0557 mmol) in a 10 mL flask with a stir bar was added 1 mL of acetone (distilled from $CaSO_4$). After deoxygenation of the mixture by four freeze-pump-thaw cycles, the solution was stirred at 40° C. under a positive pressure of argon for 4 h. Acetone was removed under reduced pressure and the product was purified by flash chromatography (silica gel, 80% ethyl acetate/hexanes) followed by separation by HPLC (80% ethyl acetate/hexanes, Rainin Microsorb column, 4.0 mL/min flow rate) to afford three components in the following order of elution: major product A (17.0 mg, 86.4%), recovered starting material B (1.4 mg, 7.1%), and minor product C (1.5 mg, 7.6%). Each purified component was characterized by spectroscopic analysis. Compound A was identified as 7,8-cis-1α,25-dihydroxyvitamin $D_3$ (6, analog JR), compound B as the starting vinylallenol JV (4) and compound C as 1α,25-dihydroxy-cis-isotachysterol.

$^1$H-NMR (300 MHZ): ($CDCl_3$) δ0.64 (3H, $C_{18}$—$CH_3$, s), 0.95 (3H, $C_{21}$—$CH_3$, d, $J^{18}$ 6.4 Hz), 1.22 (6H, $C_{26,27}$—$2CH_3$, s), 1.0–2.1 (remaining ring and side chain hydrogens, series of m), 2.24 (1H, dd, J⁻12.4 Hz, 9.0 Hz), 2.55 (1H, dd, J⁻12.5 Hz, 3.4 Hz), 4.17 (1H, $C_3$—H, dddd,J⁻4.2 Hz, 4.2 Hz, 4.2 Hz), 4.42 Hz), 4.42 (1H, $C_1$—H, br s), 5.01 (1H, $C_{19}$—H, br s), 5.32 (1H, $C_{19}$—H, br s), 6.20 and 6.54 (2H, $C_6$—H and $C_7$—H, AB pattern, J⁻11.5 Hz).

$^{13}$C-NMR (75.5 MHZ): ($CDCl_3$) δ12.6, 19.1, 20.9, 24.1, 26.3, 28.4, 29.2, 29.4, 36.1, 36.5, 39.0, 40.7, 42.7, 44.4, 45.9, 46.7, 55.0, 56.1, 66.6, 71.1, 72.1, 113.9, 121.2, 126.2, 133.1, 142.5, 146.3.

UV: (100% EtOH) $\lambda_{max}$ 266 nm (ε 15,000); $\lambda_{min}$ 228 nm (ε9,300). HRMS: m/z 416.3281 (calcd. for $C_{27}H_{44}O_3$, 416.3292).

MS: m/z 416 (8), 398 (10), 380 (17), 362 (8), 347 (6), 306 (2), 267 (7), 251 (41), 225 (10), 197 (30), 181 (11), 131 (25), 105 (57), 91 (49), 81 (32), 69 (56), 59 (base).

Example 18

Chemical Synthesis of Analog JS

This example illustrates preparation of analog JS, namely 5,6-trans-7,8-cis-1α,25-dihydroxyvitamin $D_3$, as seen in Scheme H.

Preparation of sulfur dioxide adducts A and B of 7,8-cis-1α,25-dihydroxyvitamin $D_3$, compounds (7a) and (7b).

A solution of the 7,8-cis-isomer 6 (15.6 mg, 0.0374 mmol) in dichloromethane (4 mL) was cooled to −15° C. Sulfur dioxide (5 mL), pre-dried by passage through concentrated sulfuric acid, was condensed into the cooled reaction flask. The solution was stirred for 3 h at −15° C. and then the mixture was slowly warmed to room temperature, allowing the $SO_2$ to boil off. The solvent was removed under reduced pressure and pure product was obtained by HPLC (100% ethyl acetate, Rainin Microsorb column, 4 mL/min flow rate) as two fractions, A (7.2 mg, 40%; colorless, solid residue) and B (5.5 mg, 31%; colorless, solid residue). A and B were identified as the two epimeric sulfone adducts 7a and 7b, but absolute stereochemical identification was not attempted.

Spectral Data for Adduct A (7a):

$^1$H-NMR (300 MHZ): (CDCl$_3$) δ0.68 (3H, C$_{18}$—CH$_3$, S), 0.96 (3H, C$_{21}$—CH$_3$, d, J~6.2 Hz), 1.22 (6H, C$_{26,27}$—2CH$_3$, s), 1.25–2.38 (remaining ring and side chain hydrogens, series of m), 3.68 (1H, C$_{19}$—H, d, J~16.2 Hz), 3.98 (1H, C$_{19}$—H, d, J~16.2 Hz), 4.24 (1H, C$_3$—H, dddd, J~4.3 Hz, 4.3 Hz, 4.3 Hz, 4.3 Hz), 4.40 (1H, C$_1$—H, br s), 4.93 and 5.02 (2H, C$_6$—H and C$_7$—H, AB pattern, J~11.2 Hz).

$^{13}$C-NMR (75.5 MHZ): (CDCl$_3$) δ12.9, 19.1, 20.9, 23.8, 26.5, 28.1, 29.3, 34.4, 36.2, 36.4, 39.0, 40.2, 40.4, 44.3, 46.2, 55.0, 55.1, 55.8, 63.8, 65.5, 66.9, 71.1, 111.8, 128.8, 134.0, 150.6.

IR: (CCl$_4$) ν3200–3600 (C—OH, br s), 2880–2980 (C—H, s), 1660–1680 (C=C, w), 1315 (sulfone, s), 1115 (sulfone, m) cm$^{-1}$.

HRMS: FAB (NBA), m/z 479.2849 (calcd. for C$_{27}$H$_{44}$O$_5$S minus H, 479.2833).

Spectral data for Adduct B (7b):

$^1$H-NMR (300 MHZ): (CDCl$_3$) δ0.73 (3H, C$_{18}$—CH$_3$, s), 0.95 (3H, C$_{21}$—CH$_3$, d, J~6.4 Hz), 1.21 (6H, C$_{26,27}$—2CH$_3$, s), 1.25–2.09 (remaining ring and side chain hydrogens, series of m), 2.29 (1H, br d, J~13.1 Hz), 2.46 (1H, br d, J~17.5 Hz), 3.70 (1H, C$_{19}$—H, d, J~15.8 Hz), 4.01 (1H, C$_{19}$—H, d, J~15.8 Hz), 4.23 (1H, C$_3$—H, m), 4.40 (1H, C$_1$—H, br s), 4.87 and 4.98 (2H, C$_6$—H and C$_7$—H, AB pattern, J~11.0 Hz).

$^{13}$C-NMR (75.5 MHZ): (CDCl$_3$) δ12.7, 19.1, 20.9, 23.9, 25.8, 28.4, 29.1, 29.4, 33.8, 35.9, 36.5, 39.1, 40.0, 40.6, 44.3, 46.9, 55.0, 55.3, 55.7, 64.0, 65.0, 66.9, 71.2, 112.4, 128.6, 134.0, 150.8.

IR: (CCl$_4$) ν 3200–3600 (C—OH, br s), 2860–2980 (C—H, s), 1650–1680 (C=C, w), 1315 (sulfone, s), 1115 (sulfone, m) cm$^{-1}$.

HRMS: FAB (NBA), m/z 479.2822 (calcd. for C$_{27}$H$_{44}$O$_5$S minus H, 479.2833).

Preparation of 5,6-trans-7,8-cis-1α,25-dihydroxyvitamin D$_3$ (8, Analog JS) via Sulfur Dioxide Adducts The sulfone Isomer A (7a, 4.0 mg, 0.0083 mmol) and NaHCO$_3$ (14 mg) were dissolved in ethanol (5 mL). The solution was flushed with argon for 10 min, then heated at 78° C. for 1.5 h. Solvent was removed and the crude product, obtained by flash chromatography (silica gel, 80% ethyl acetate/hexanes), was subjected to HPLC purification (80% ethyl acetate/hexanes, Rainin Microsorb column, 4 mL/min flow rate) to afford pure 5,6-trans-7,8-cis-1α,25-dihydroxyvitamin D$_3$ (3.3 mg, 95%) as a colorless, viscous foam. Likewise, treatment of sulfone Isomer B (7b, 3.3 mg, 0.0069 mmol) with NaHCO$_3$ (15 mg) in ethanol (5 mL) followed by work up and purification exactly as above afforded pure 8 (2.5 mg, 86%) as a colorless, viscous foam.

Spectral data:

$^1$H-NMR (300 MHZ): (CDCl$_3$) δ0.66 (3H, C$_{18}$—CH$_3$, s), 0.96 (3H, C$_{21}$—CH$_3$, d, J~6.3 Hz), 1.22 (6H, C$_{26,27}$—2CH$_3$, s), 1.24–2.34 (remaining ring and side chain hydrogens, series of m), 2.78 (1H, dd, J~12.9 Hz, 2.7 Hz), 4.20–4.28 (1H, C$_3$—H, m, W~26 Hz), 4.45–4.52 (1H, C$_1$—H, m, W~23 Hz), 4.95 (1H, C$_{19}$—H, br s), 5.05 (1H, C$_{19}$—H, br s), 6.15 and 6.75 (2H, C$_6$—H and C$_7$—H, AB pattern, d, J~11.8 Hz).

$^{13}$C-NMR (75.5 MHZ): (CDCl$_3$) δ12.7, 19.1, 20.9, 24.2, 26.4, 28.4, 29.2, 29.4, 29.7, 35.9, 36.1, 36.5, 39.4, 40.7, 42.0, 44.4, 46.8, 55.0, 56.2, 66.0, 70.9, 109.1, 120.1, 124.6, 133.1, 144.2, 152.0.

UV: (100% EtOH) λ$_{max}$ 274 nm (ε 17,400); λ$_{min}$ 234 nm (ε5,500).

HRMS: m/z 416.3284 (calcd. for C$_{27}$H$_{44}$O$_3$, 416.3292).

MS: m/z 416 (15, M), 398 (12), 380 (10), 365 (4), 342 (3), 329 (2), 313 (3), 287 (7), 269 (7), 251 (9), 227 (5), 209 (6), 175 (12), 152 (28), 134 (base), 107 (22), 95 (30), 81 (29), 69 (30), 59 (42).

Example 19

Chemical Synthesis of Analog JV

This example illustrates preparation of JV, namely (1S,3R,6S)-1,3,25-trihydroxy-9,10-secocholesta-5(10),6,7-triene as seen in Scheme H.

Preparation (1S,3R,8S)-8-benzoyloxy-1,3-di[(tert-butyldimethylsilyl)oxy]-25-trimethylsilyloxy-9,10-secocholest-5(10)-en-6-yne (3)

To A-ring enyne 1 (483 mg, 1.36 mmol) in dry ether (1.6 mL) under an argon atmosphere at 0°C. was added n-BuLi (1.4 mmol, 0.88 mL, 1.6 M in hexanes). The solution was stirred for 1 h at 0° C., then the ketone 2 (402 mg, 1.14 mmol) in ether (3 mL) was added dropwise. The solution was stirred at 0° C. for 10 min, then warmed to room temperature. After stirring the mixture for 1 h, brine (1 mL) was added, the mixture was diluted with ether (10 mL), and the aqueous layer was extracted with ether (2×10 mL). The combined ether extracts were dried (MgSO$_4$). The residual oil after evaporation was purified by flash chromatography (silica gel, 5% ethyl acetatee/hexanes) followed by HPLC (5% ethyl acetate/hexanes, Rainin Dynamax column, 8 mL/min flow rate) to afford pure product (1S,3R,8S)-8-Hydroxy-1,3-di(tert-butyldimethylsilyloxy)-25-trimethylsilyloxy-9,10-secocholest-5(10)-en-6-yne (661 mg, 79% yield). The propargyl alcohol was identified by spectroscopic analysis.

$^1$H-NMR (300 MHZ): (CDCl$_3$) δ0.06 (6H, Si—2CH$_3$, s), 0.09 (6H, Si—2CH$_3$, S), 0.10 (9H, Si—3CH$_3$, s), 0.9–1.0 (24H, series of overlapping signals due to 2 Si-tBu, C$_{18}$—CH$_3$ and C$_{21}$—CH$_3$), 1.20 (6H, C$_{26,27}$—CH$_3$, s), 1.87 (3H, C$_{19}$—CH$_3$, br s), 0.97–2.39 (remaining ring and side chain hydrogens, series of m), 4.03–4.12 (1H, C$_1$—H, m, W~26.7 Hz), 4.17 (1H, C$_3$—H, br s).

$^{13}$C-NMR (75.5 MHZ): (CDCl$_3$) δ-4.8, -4.7, -4.6, -4.3, 2.6, 13.0, 18.0, 18.1, 18.4, 18.6, 19.1, 20.8, 21.1, 25.8, 25.9, 26.7, 29.8, 29.9, 35.3, 36.2, 39.7, 40.0, 40.4, 41.2, 42.5, 45.2, 56.3, 56.9, 64.1, 69.8, 69.9, 74.1, 82.1, 96.6, 114.7, 141.3.

HRMS: (FAB) m/z 731.5295 (calcd. for C$_{42}$H$_{80}$O$_4$Si$_3$, 733.318).

MS: m/z 731 (5, M—H), 715 (11, M—OH), 676 (2), 625 (2), 600 (21), 583 (12), 569 (3), 493 (3), 469 (3), 437 (4), 379 (6), 355 (5), 323 (5), 301 (7), 275 (8), 249 (18), 223 (9), 191 (11), 165 (25), 157 (10), 147 (54), 131 (base).

To the propargyl alcohol (586 mg, 0.818 mmol) in dry ether (3 mL) at −78° C. under an argon atmosphere was added n-BuLi (0.88 mmol, 0.55 mL, 1.6 M in hexanes). The solution was warmed to room temperature and stirred for 2.3 h then recooled to −78° C. Freshly distilled benzoyl chloride (103 μL, 0.883 mmol) was added dropwise. The solution was warmed to room temperature and stirred for 2 h. The reaction was quenched with saturated aqueous NaHCO$_3$ (1 mL) and diluted with ether (20 mL). The organic layer was washed with NaHCO$_3$ (2×5 mL) and brine (1×5 mL) and dried (MgSo$_4$). The concentrated oil was purified by flash chromatography (silica gel, 2.5% ethyl acetate/hexanes) followed by HPLC (2.5% ethyl acetate/hexanes, Rainin Dynamax column, 8 mL/min flow rate) to afford pure benzoate 3 (405 mg, 59%) and recovered propargyl alcohol (156 mg, 27%), in that order of elution. The propargyl benzoate 3 was characterized by spectroscopic analysis.

$^1$H-NMR (300 MHZ): (CDCl$_3$) δ0.05 (6H, Si—2CH$_3$, s), 0.08 (6H, Si—2CH$_3$, s), 0.11 (9H, Si—3CH$_3$, s), 0.87 (9H, Si-tBu, s), 0.88 (9H, Si-tBu, s), 0.93 (3H, C$_{21}$—CH$_3$, d, J~6.5 Hz), 1.04 (3H, C$_{18}$—CH$_3$, s), 1.21 (6H, C$_{26,27}$—CH$_3$, s), 1.88 (3H, C$_{19}$—CH$_3$, s), 1.26–2.08 (remaining ring and side chain hydrogens, series of m), 2.36 (1H, dd, J~16.7 Hz, 4.5 Hz), 3.12 (1H, d, J~10.1 Hz), 4.01–4.09 (1H, C$_3$—H, m, W~32 Hz), 4.14 (1H, C$_1$—H, br s), 7.43 (2H, m-Ar, t, J~7.4 Hz, 7.7 Hz), 7.55 (1H, p-Ar, t, J~7.3 Hz), 8.05 (2H, o-Ar, d, J~7.4 Hz).

$^{13}$C-NMR (75.5 MHZ): (CDCl$_3$) δ-4.8 , -4.7 , -4.6 , -4.3, 2.7, 13.9, 18.0, 18.1, 18.5, 18.7, 19.1, 20.8, 21.4, 25.8, 25.9, 26.6, 29.9, 30.0, 35.4, 35.8, 36.1, 39.5, 39.7, 41.3, 42.6, 45.2, 57.0, 57.5, 64.1, 64.9, 74.1, 77.1, 84.5, 92.1, 114.8, 128.3, 129.6, 131.5, 132.6, 141.8, 164.5.

IR: (CCl$_4$) ν 3590 (monosubstituted benzene, w), 2870–2980 (C—H, s), 2220 (C$_{-C, w}$), 1745 (C=O, s) cm$^{-1}$.

UV: (100% EtOH) λ$_{max}$ 232 nm (ε 23,700).

HRMS: (FAB) m/z 835.5564 (calcd. for C$_{49}$H$_{84}$O$_5$Si$_3$ minus H, 835.5551).

MS: m/z 836 (2), 716 (13), 675 (2), 584 (12), 541 (2), 493 (4), 463 (4), 437 (5), 355 (8), 301 (9), 223 (11), 179 (30), 131 (59), 105 (base).

Preparation of analog JV, (1S,3R,6S)-1,3,25-trihydroxy-9,10-secocholesta-5(10),6,7-triene (4)

Freshly purified 1,2-diiodoethane (412 mg, 1.46 mmol) and samarium metal (286 mg, 1.90 mmol) were dried under vacuum and suspended in 4 mL THF under an argon atmosphere. This solution was stirred for 2 h until it became deep blue. A solution of propargyl benzoate 3 (477 mg, 0.570 mmol) and Pd(PPh$_3$)$_4$ (65.8 mg, 0.037 mmol) in 6 mL THF was added via cannula. Freshly distilled isopropanol (from CaO, 0.5 mL) was added and the solution was stirred under a positive argon atmosphere for 14 h. Saturated aqueous Na$_2$CO$_3$ (2 mL) was added to quench the reaction. The organic layer was diluted with ether and then the mixture was washed with Na$_2$CO$_3$ (3×10 mL), dried with MgSO$_4$ and concentrated. The product was purified by flash chromatography (silica gel, 2% ethyl acetate/hexanes) followed by HPLC (2% ethyl acetate/hexanes, Rainin Dynamax column, 8 mL/min flow rate) to afford silyl protected vinylallene (1S,3R,6S)-1,3-di(tert-butyldimethylsilyloxy)-25-trimethylsilyloxy-9,10-secocholesta-5(10),6,7-triene (0.3085 g, 75.5%). The product was identified only by $^1$H-NMR analysis and immediately deprotected as described below. This material appeared to be more stable as the triol 4.

Spectral data:

$^1$H-NMR (300 MHZ): (CDCl$_3$) δ0.06 (6H, Si—2CH$_3$, s), 0.10 (9H, Si—3CH$_3$, s), 0.11 (6H, Si—2CH$_3$, S), 0.73 (3H, C$_{21}$—CH$_3$, s), 0.89 (9H, Si-tBu, s), 0.91 (9H, Si—tBu, s), 0.94 (3H, C$_{18}$—CH$_3$, d, J~6.5 Hz), 1.20 (6H, C$_{26,27}$—CH$_3$, s), 1.76 (3H, C$_{19}$—CH$_3$, s), 1.26–2.50 (remaining ring and side chain hydrogens, series of m), 4.09–4.13 (1H, C$_3$—H, m, overlapping C$_1$—H), 4.17 (1H, C$_1$—H, br distorted singlet), 6.13 (1H, C$_6$—H, dd, J~3.9 Hz, 3.9 Hz). Minor impurity peaks were detectable and this compound was best characterized as the deprotected triol.

To the silyl protected vinylallene (0.1054 g, 0.1469 mmol) was added tetra-n-butyl ammonium fluoride (1 M in THF, 1.6 mL, 1.6 mmol). The solution was stirred under an argon atmosphere for 19 h. Water (1 mL) was added and the solution stirred 30 min. The mixture was extracted with ether (3×15 mL) and the ether extracts washed with brine (1×10 mL) and dried (MgSO$_4$). The concentrated residue was subjected to flash chromatography (silica gel, 80% ethyl acetate/hexanes) followed by HPLC (80% ethyl acetate/hexanes, Rainin Microsorb column, 4 mL/min flow rate) to afford purified deprotected vinylallene 4 (Analog JV) together with its 6R-diastereomer 5 (Analog JW) (46.1 mg, 75.3% total yield) in a ~92:8 ratio by NMR integration. By a tedious HPLC separation (same conditions as above by shave-recycling), pure 5 could be obtained and characterized by spectroscopic analysis:

The data for compound 4 are as follows:

$^1$H-NMR (300 MHZ) : (CDCl$_3$) δ0.74 (3H, C$_{18}$—CH$_3$, s), 0.95 (3H, C$_{21}$—CH$_3$, d, J~6.4 Hz), 1.22 (6H, C$_{26,27}$—CH$_3$, s), 1.87 (3H, C$_{19}$—CH$_3$, s), 1.25–2.10 (remaining ring and side chain hydrogens, series of m), 2.29 (1H, br d, J~13.2 Hz), 2.62 (1H, br dd, J~16.5 Hz, 4.5 Hz), 4.11–4.20 (1H, C$_3$—H, m, W~27.8 Hz), 4.23 (1H, C$_1$—H, br m W~8.6 Hz), 6.14 (1H, C$_6$—H, dd, J~4.1 Hz, 4.1 Hz).

UV: (100% EtOH) λ$_{max}$ 242 nm (ε 24,300), 234 nm (ε 23,500).

HRMS: m/z 416.3277 (calcd. for C$_{27}$H$_{44}$O$_3$, 416.3292).

MS: m/z 416 (10), 398 (10), 380 (9), 365 (4), 342 (2), 328 (2), 313 (2), 287 (5), 269 (5), 251 (8), 197 (7), 159 (15), 134 (54), 105 (32), 95 (29), 81 (38), 69 (40), 59 (base).

Example 20

Chemical Synthesis of Analog JW

This example illustrates preparation of the analog JW, namely, (1S,3R,6R)-1,3,25-trihydroxy-9,10-secocholesta-5 (10),6,7-triene (5), as seen in Scheme H.

A solution of (6S/6R)-vinylallenes 4, 5 (2.6 mg, 0.0062 mmol, an ~92:8 ratio of 6S:6R) in methanol-d$_4$ (1 mL) was prepared in a quartz NMR tube. The solution was saturated with argon for 30 min and then the NMR tube was capped and then irradiated with ultraviolet light from a Hanovia 450 watt medium pressure mercury lamp for 30 min. Integration of the C$_{18}$—Me signals in the NMR spectrum revealed a ~50:50 mixture of the two isomers. Solvent was removed and the products separated by HPLC (11% isopropanol/hexanes, Rainin Microsorb column, 6 mL/min, flow rate). Taking a front cut of the overlapping peaks gave pure (6R)-vinylallene 5 (0.9 mg, 35%). This product was identified and characterized through spectroscopic analysis.

$^1$H-NMR (300 MHZ): (CDCl$_3$) δ0.65 (3H, C$_{18}$—CH$_3$, s), 0.94 (3H, C$_{21}$—CH$_3$, d, J~6.4 Hz), 1.21 (6H, C$_{26,27}$—2CH$_3$, s), 1.87 (3H, C$_{19}$—CH$_3$, br s), 1.25–2.32 (remaining ring and side chain hydrogens, series of m), 2.28 (1H, br d, J~13.0 Hz), 2.52 (1H, dd, J~16.3 Hz, 5.0 Hz), 4.12 (1H, C$_3$—H, m, W~30.0 Hz, overlapping), 4.20 (1H, C$^1$—H, br s), 6.10 (1H, C$_6$—H, dd, J~3.2 Hz, 3.2 Hz).

UV: (100% EtOH) λ$_{max}$ 242 nm (ε 22,300), 234 nm (ε22,100).

HRMS: m/z 416.3291 (calcd. for C$_{27}$H$_{44}$O$_3$, 416.3292).

MS: m/z 416 (25, M), 398 (20), 380 (26), 365 (7), 347 (5), 325 (5), 313 (3), 287 (11), 269 (13), 251 (38), 225 (12), 213 (14), 197 (26), 173 (19), 159 (25), 145 (32), 133 (35), 105 (47), 95 (33), 81 (38), 69 (47), 59 (base).

Scheme I relates to analogs JX and JY described in Examples 21 and 22.

Scheme I

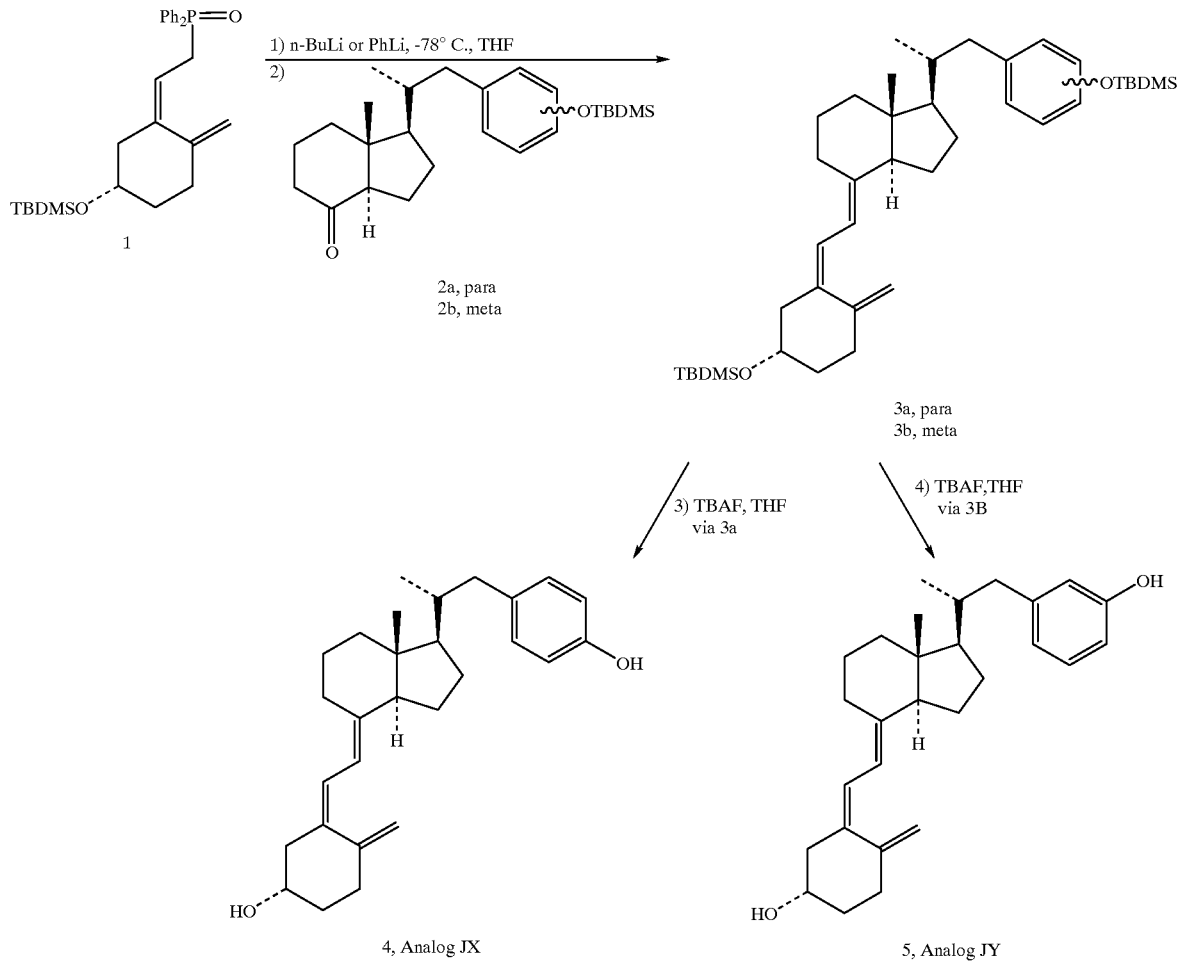

Example 21

Chemical Synthesis of Analog JX

This example illustrates preparation of the analog JX, namely 22-(p-hydroxyphenyl)-23,24,25,26,27-pentanor-vitamin $D_3$ (4), as seen in Scheme I.

The A-ring phosphine oxide 1, (48 mg, 0.11 mmol) in dry THF (1.8 mL) was cooled to −78° C. and n-butyllithium (1.5 M in hexanes, 0.074 mL, 0.11 mmol) was added dropwise via a syringe. The resulting deep red solution was stirred for 10 min and then treated with a solution of CD-ring ketone 2a (28 mg, 0.070 mmol) in dry THF (0.6 mL) via cannula. The mixture was stirred 2 h at −78° C., warmed to room temperature and quenched with water (5 mL). The aqueous layer was separated and extracted with EtOAc (3×5 mL). The combined organic layers were washed with brine, dried over $Na_2SO_4$, and concentrated. The crude residue was purified by rapid filtration through a short silica gel column (20% EtOAc/hexanes) to afford 20.1 mg (46%) of the protected vitamin 3a. The latter (20.1 mg, 0.0315 mmol) in THF (1 mL) was placed under argon and TBAF (0.32 mL, 1 M in THF, 0.32 mmol) was added dropwise. After stirring for 18 h, the solvent was partially evaporated and the residue diluted with water (5 mL). After extracting the aqueous layer with EtOAc (3×5 mL), the combined organic layers were washed with brine and dried over $Na_2SO_4$. The residue was then purified by HPLC (20% EtOAc/hexanes) to afford, after vacuum drying, 4.7 mg (36%) of the desired product 4 (Analog JX).

$^1$H-NMR (300 MHZ): (CDCl$_3$) δ0.57 (3H, C$_{18}$—Me), 0.81 (3H, H$_{21}$, d, J¯6.4 Hz), 1.2–1.5 (remaining ring and side chain hydrogens, series of m), 2.58 (dd, J¯13.0 Hz, 3.0 Hz), 2.83 (dd, J¯13.1 Hz, 3.0 Hz), 3.96 (1H, H$_3$, m), 4.83 (1H, H$_{19}$, br s), 5.06 (1H, H$_{19}$, br s), 6.05 (1H, d, J¯11.2 Hz), 6.24 (1H, d, J¯11.2 Hz), 6.74 (2H, Ar—H$_{3',5'}$, d, J¯8.4 Hz), 7.00 (2H, Ar—H$_{2,6}$, d, J¯8.3 Hz).

UV: (100% EtOH) λ$_{max}$ 266 nm (ε 20,600); λ$_{min}$ 240 nm (ε 15,000).

HRMS: m/z 406.2855 (calcd. for $C_{28}H_{38}O_2$, 406.2973).

MS: m/z 406 (23, M), 388 (3), 373 (11), 347 (35), 299 (4), 281 (5), 253 (45), 239 (3), 211 (5), 197 (5), 158 (14), 136 (29, A-ring fragment due to C$_{7,8}$ a cleavage), 118 (30, m/z 136-H$_2$O ), 107 (base), 91 (20), 81 (16), 67 (10), 55 (17).

Example 22

Chemical Synthesis of Analog JY

This example illustrates preparation of the analog JY, namely 22-(m-Hydroxyphenyl)-23,24,25,26,27-pentanor-vitamin $D_3$ (5), as seen in Scheme I.

The A-ring phosphine oxide 1, (70 mg, 0.154 mmol) in dry THF (2.8 mL) was cooled to −78° C. under argon and n-butyllithium (1.5 M in hexanes, 0.100 mL, 0.154 mmol) was added via a syringe. The solution was stirred 10 min and then treated dropwise with a solution of CD-ring ketone 2b (41 mg, 0.102 mmol) in dry THF (0.85 mL). The mixture was stirred 2 h at −78° C. and then allowed to warm to room temperature over 1 h. The solvent was partially evaporated and then quenched with 5 mL water. The aqueous layer was separated and extracted with EtOAc (3×5 mL). The combined organic layers were washed with brine, dried over $Na_2SO_4$ and concentrated. The crude residue was purified by rapid filtration through a short silica gel column (20% EtOAc/hexanes) to yield 19.2 mg (29%) of the protected vitamin 3b. The protected vitamin (19.2 mg, 0.03 mmol) in dry THF (1 mL) was placed under argon and TBAF (1 M in THF, 0.30 mn, 0.30 mmol) was added dropwise. After stirring 18 h, the solvent was partially evaporated and diluted with water (5 mL). After extracting the aqueous layer with EtOAc (3×5 mL), the combined organic layers were washed with brine and dried over $Na_2SO_4$. The residue was purified by HPLC (20% EtOAc/hexanes) and after vacuum drying afforded 2.8 mg (23%) of the desired product 5 (Analog JY).

$^1$H-NMR (300 MHZ): (CDCl$_3$) δ0.58 (3H, $H_{18}$—CH$_3$, s), 0.83 (3H, $H_{20}$—CH$_3$, d, J¯6.5 Hz), 1.2–1.5 (remaining ring and side chain hydrogens, series of m), 2.58 (1H, dd, J¯13.0 Hz, 3.3 Hz), 2.85 (2H, $H_{22}$, m), 3.97 (1H, $H_3$, m), 4.83 (1H, $H_{19}$, s), 5.07 (1H, $H_{19'}$, s), 6.06 (1H, $H_{6,7}$, AB pattern, d, J¯11.2 Hz), 6.24 (1H, $H_{6,7}$, AB pattern, d, J¯11.2 Hz), 6.63 (1H, Ar H, s), 6.64 (1H, Ar H, d, J¯7.4 Hz), 6.71 (1H, Ar H, d, J¯7.52 Hz), 7.13 (1H, Ar H, dd, J¯15.45 Hz, 7.8 Hz).

HRMS: m/z 406.2872 (calcd. for $C_{28}H_{38}O_2$, 406.2873).

MS: m/z 406 (44), 373 (14), 347 (7), 299 (6), 271 (9), 253 (7), 211 (12), 176 (20), 158 (30), 136 (23), 118 (54), 107 (35), 91 (23), 79 (22), 67 (12), 55 (11).

Scheme J relates to analog LO described in Example 23.

Scheme J

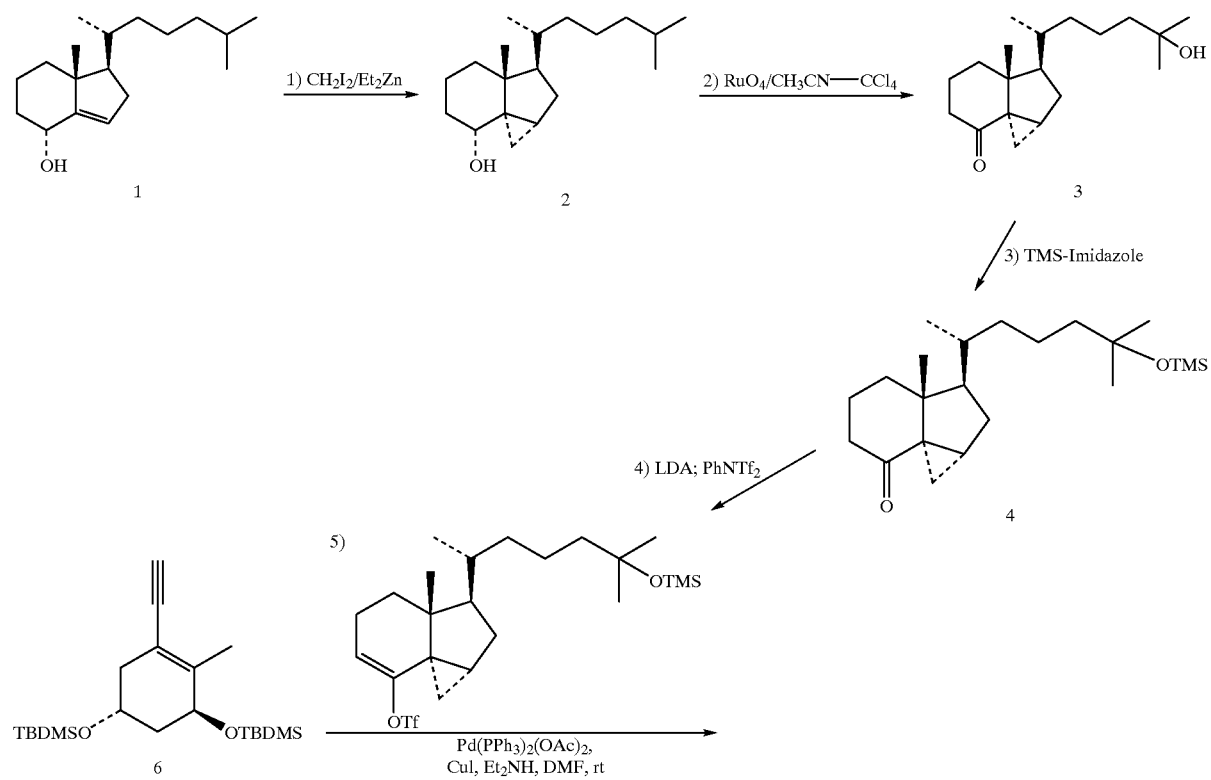

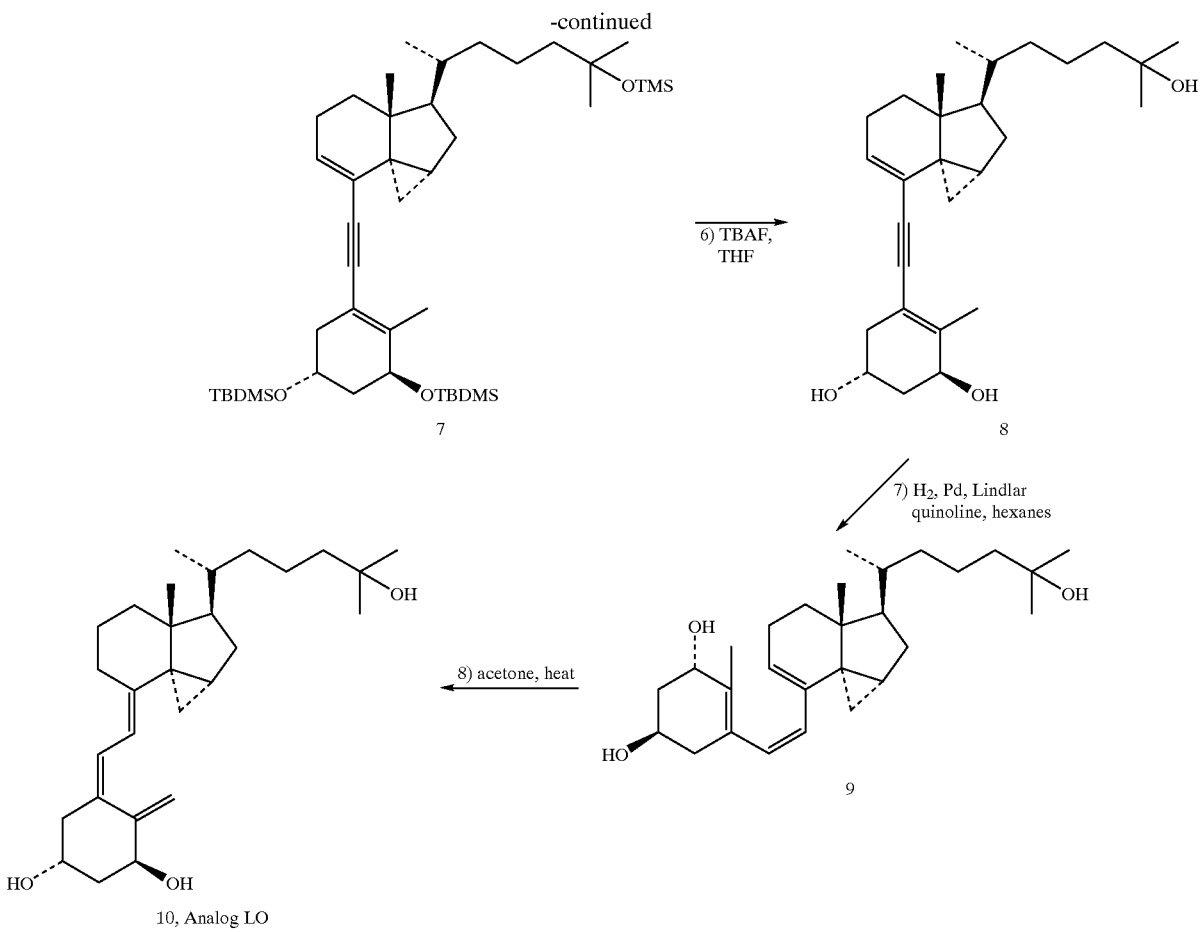

Example 23

Chemical Synthesis of Analog LO

This example illustrates preparation of the analog LO, namely (14R,15S)-14,15-methano-1α,25-dihydroxyvitamin D$_3$ (10) as seen in Scheme J.

Preparation of (8R,14R,15S)-de-A,B-14(15)-cyclopropylcholest-8-ol (2)

Into a dry 250 mL Schlenk tube flushed with argon and equipped with a stir bar was placed the (8R)-De-A,B-cholest-14-en-8-ol (1) (1.50 g, 5.6 mmol), diiodomethane (15.0 g, 4.5 mL, 56 mmol) and dry CH$_2$Cl$_2$ (100 mL). The mixture was cooled to −78° C. while stirring. Diethyl zinc (1.0 M solution in hexanes, 28.0 mL, 28 mmol) was added to the mixture via gas tight syringe. The mixture was stirred at −78° C. for 4 h and then allowed to warm to room temperature overnight. The mixture was then treated with saturated NH$_4$Cl and extracted with ether (3×50 mL). The combined ethereal phase was washed with saturated NaHCO$_3$ and brine and dried over MgSO$_4$. The solvent was removed to give a yellow milky liquid. Flash chromatography (20% EtOAc/hexanes) afforded 2 as a thick, colorless oil (1.24 g, 79%).

$^1$H-NMR (300 MHZ, CDCl$_3$): δ0.23 (dd, J~3.9, 2.8 Hz, 1H, H$_b$), 0.39 (dd, J~7.7, 4.3 Hz, 1H, H$_a$), 0.80–0.90 (m, 12H, C$_{18}$—Me, C$_{21}$—Me, C$_{26,27}$—2Me), 0.90–2.00 (remaining ring and side chain hydrogens, series of m), and 4.16 (dd, J~10.8, 4.2 Hz, 1H, H$_c$).

13C-NMR (75.5 MHZ, CDCl$_3$): δ5.1, 15.3, 17.6, 18.7, 21.7, 22.5, 22.8, 23.7, 28.0, 32.4, 33.8, 35.0, 35.5, 36.1, 39.5, 40.9, 43.2, 49.0, and 66.8. IR (CCl$_4$): ν3320 (O—H) and 2940 (C—H).

MS (m/z): 278 (M$^+$, 12%), 261 (M$^+$—OH, 23), 260 (M$^+$—H$_2$O, 14), 175 (16), 165 (M$^+$—C$_8$H$_{17}$, 29), 149 (12), 148 (17), 147 (89), 123 (10), 121 (14), 111 (base), 109 (12), 105 (15), 95 (18), 93 (11), 91 (13), 81 (16), 57 (12), 55 (14), and 43 (26).

Exact Mass (m/z): calculated for C$_{19}$H$_{34}$O: 278.2610. Found: 278.2608.

Preparation of (14R,15S)-de-A,B-14(15)-cyclopropyl-25-hydroxycholest-8-one (3)

Into a 100 mL round bottom flask was placed the α-cyclopropyl alcohol 2 (1.21 g, 4.52 mmol), NaIO$_4$ (3.38 g, 15.8 mmol), RuCl$_3$.XH$_2$O (0.187 g, 0.90 mmol) and a stir bar. The mixture was dissolved in CH$_3$CN (18.1 mL), CCl$_4$ (18.1 mL) and 0.5 M KH$_2$PO$_4$+0.5 M NaOH (22.6 mL). The mixture was degassed and flushed with argon. The mixture was stirred at 54° C. After 10 min the mixture turned from black to yellow. After 18 h, the solution turned black. The mixture was treated with id brine and extracted several times with ether. The ether layer was dried over MgSO$_4$ filtered and concentrated. The crude could be flushed with 20% EtOAc/hexanes but was purified via HPLC (Rainin Dynamax-60A, 2.14×25 cm, 8 μm silica gel column, 25% EtOAc/hexanes, 8 mL/min) to afford 3 as a colorless oil (0.332 g, 25% yield). $^1$H-NMR (300 MHZ, CDCl$_3$): δ0.31

(dd, J~8.0, 4.0 Hz, 1H, H$_a$), 0.80 (s, 3H, C$_{18}$—Me), 0.86 (d, J~6.4 Hz, 3H, C$_{21}$—Me), 0.90–2.36 (remaining ring and side chain hydrogens, series of m), and 1.14 (s, 6H, C$_{27,26}$—2Me).

$^{13}$C-NMR (75.5 MHZ, CDCl$_3$): δ18.4, 18.6, 18.7, 19.4, 20.6, 21.4, 29.2, 29.3, 31.5, 33.7, 34.4, 36.0, 38.4, 42.7, 44.2, 46.9, 47.9, 70.8, and 211.9.

IR (CCl$_4$): ν3448 (O—H), 2966 (C-H), and 1701 (C=O).

UV (100% EtOH): λ$_{max}$ 212 nm (ε 1400).

MS (m/z): 292 (M$^+$, 1.3%), 274 (M$^+$—H$_2$O, 13), 164 (25), 163 (36), 150 (12), 149 (19), 147 (14), 145 (18), 137 (25), 136 (71), 135 (37), 136 (71), 137 (25), 105 (22), 95 (18), 93 (25), 92 (13), 91 (43), 81 (17), 79 (34), 77 (21), 69 (22), 67 (22), 61 (43), 59 (59), 55 (38), 45 (35), 44 (19), and 43 (base).

Exact Mass (m/z): calculated for C$_{19}$H$_{32}$O$_2$: 292.2402. Found: 292.2407.

Preparation of (14R,15S)-de-A,B-25-trimethylsilyloxy-14(15)-cyclopropylcholest-8-one (4)

Into a dry 25 mL round bottom flask equipped with a stir bar and flushed with argon was placed the 25-hydroxycyclopropylketone 3 (0.320 g, 1.09 mmol) and dry THF (14 mL). TMS-imidazol (0.48 mL, 3.27 mmol) was added via syringe and the mixture was allowed to react overnight. Afterwards, the reaction mixture was immediately flushed through a short silica gel column (10% EtOAc). HPLC (Rainin Dynamax-60A, 2.14×25 cm, 8 μm silica gel column, 10% EtOAc/hexanes, 8 mL/min) afforded 4 as a colorless oil (0.327 g, 82%).

$^1$H-NMR (300 MHZ, CDCl$_3$): δ0.06 (s, 9H, SiMe$_3$), 0.33 (dd, J~8.0, 4.0 Hz, 1H, Ha), 0.83 (s, 3H, C$_{18}$—Me), 0.88 (d, J~6.5 Hz, 3H, C$_{21}$—Me), 0.93–2.38 (remaining ring and side chain hydrogens, series of m), and 1.16 (s, 6H, C$_{26,27}$—2Me).

$^{13}$C-NMR (75.5 MHZ, CDCl$_3$): δ2.6, 18.4, 18.6, 18.8, 19.4, 20.6, 21.5, 29.8, 30.0, 31.5, 33.8, 34.5, 36.0, 38.5, 42.7, 45.1, 46.9, 47.9, 74.0, and 211.8.

IR (CCl$_4$): ν2956 (C—H) and 1707 (C=O).

UV (100% EtOH): λ$_{max}$ 218 nm (ε 2000). MS (m/z): 365 (MH$^+$, 5%), 349 (19), 275 (30), 163 (39), 135 (12), 132 (13), 131 (base), 91 (13), 75 (42), 73 (41), 69 (12), 59 (18), 55 (16), and 43 (27).

Exact Mass (m/z): calculated for C$_{22}$H$_{41}$O$_2$Si (MH$^+$): 365.2876. Found: 365.2867.

Preparation of (14R,15S)-de-A,B-25-trimethylsilyloxy-14(15)-cyclopropylcholest-8-en-8-yl trifluoromethane sulfonate (5)

Lithium di-isopropyl amide (LDA) was prepared by the addition of di-isopropyl amine (0.097, 0.69 mmol) to a solution of n-BuLi in hexanes (0.48 mL, 1.6 M, 0.77 mmol) and dry THF (1 mL) at −78° C. After stirring for 10 min at −78° C. and at room temperature for 15 min the solution was again cooled to −78° C. and the 25-TMS cyclopropylketone 4 (0.200 g, 0.548 mmol) in THF (2 mL) was added dropwise via a cannula. After stirring for 15 min the enolate solution was warmed to room temperature over 2 h and then cooled to −78° C. N-phenyl trifluoramide (0.218 g, 0.61 mmol) was dissolved in dry THF (2 mL), and added to the enolate at −78° C. The reaction mixture was warmed to 0° C. and stirred for 10 h. The resulting solution was poured into water and extracted with ether, dried over MgSO$_4$, and concentrated. The yellow solid was chromatographed (hexanes) to afford 5 as a colorless oil (0.163 g, 63%).

$^1$H-NMR (300 MHZ, CDCl$_3$): δ0.10 (s, 9H, SiMe$_3$), 0.58 (dd, J~7.8, 4.7 Hz, 1H, H$_a$), 0.73 (apparent t, J~4.0 Hz, 1H, H$_b$), 0.90 (d, J~6.5 Hz, 3H, C$_{21}$—Me), 0.98 (s, 3H, C$_{18}$—Me), 1.00–2.50 (remaining ring and side chain hydrogens, series of m), 1.19 (s, 6H, C$_{26,27}$—2Me), and 5.56 (t, J~3.7 Hz, 1H, H$_9$).

$^{13}$C-NMR (75.5 MHZ, CDCl$_3$): δ2.6, 14.2, 15.1, 18.7, 20.6, 21.3, 23.7, 29.8, 30.0, 31.8, 32.8, 34.1, 36.2, 37.1, 43.4, 45.1, 46.7, 74.0, 114.7, and 150.2.

IR (CCl$_4$): ν2958 (C—H) and 1420, 1248 (S=O).

UV (100% EtOH): λ$_{max}$ 216 nm (ε3700).

MS (m/z): 495 (MH$^+$, 3%), 147 (17), 145 (18), 143 (14), 133 (14), 132 (13), 131 (base), 129 (12), 119 (11), 117 (13), 115 (21), and 105 (18).

Exact Mass (m/z): calculated for C$_{23}$H$_{38}$O$_4$F$_3$SSi(MH$^+$): 495.2212. Found: 495.2234.

Preparation of (1S,14R,15S)-1,3-di(tert-butyldimethylsilyloxy)-25-trimethylsilyloxy-14(15)-cyclopropyl-6,7-dehydroprevitamin D$_3$ (7)

To a mixture of enol triflate 5 (76.9 mg, 0.155 mmol) and enyne 6 (65 mg, 0.171 mmol) in diethylamine (1 mL) and DMF (1 mL) was added CuI (3 mg, 0.0155 mmol) and bis[triphenylphosphine]palladium (II) acetate (3.5 mg, 0.0047 mmol). The reaction mixture was stirred at room temperature for 2 h under argon. Diethyl ether was added, and the mixture was washed with water (3×5 mL), dried (MgSO$_4$), and evaporated in vacuo. The crude dark brown oil was purified by flash chromatography (5% EtOAc/hexane) to afford after vacuum drying 109.6 mg (97%) of the dienyne 7 as a viscous oil, which was sufficiently pure for the next step.

$^1$H-NMR (300 MHZ, CDCl$_3$): δ0.06 (s, 6H, SiMe$_2$), 0.09 (s, 6H, SiMe$_2$), 0.10 (s, 9H, SiMe$_3$), 0.46 (dd, J~7.5, 4.0 Hz, 1H, H$_a$), 0.59 (apparent t, J~3.6 Hz, 1H, H$_b$), 0.88 (s, 9H, Si$^t$Bu), 0.89 (s, 9H, Si$^t$Bu), 0.90 (superimposed signal, 3H, C$_{21}$—Me), 0.92 (s, 3H, C$_{18}$~Me), 0.94–2.43 (remaining ring and side chain hydrogens, series of m), 1.19 (s, 6H, C$_{26,27}$—2Me), 1.86 (br s, 3H, C$_{19}$—Me), 4.08 (m, 1H, H$_3$), 4.18 (apparent t, J~3.2 Hz, 1H, H$_1$), and 5.95 (apparent t, J~3.8 Hz, 1H, H$_9$).

$_{13}$C-NMR (75.5 MHZ, CDCl$_3$): δ−4.8, −4.7, −4.65, −4.4, 2.6, 14.9, 15.1, 18.0, 18.7, 19.1, 20.6, 20.7, 25.2, 25.8, 25.9, 29.8, 29.9, 32.5, 32.7, 34.3, 36.2, 37.9, 39.8, 40.5, 41.2, 45.2, 47.2, 64.1, 69.9, 74.0, 87.9, 90.2, 115.3, 125.2, 132.1, and 140.4.

IR (NaCl): ν2970, 2880 (C—H), 2190 (C_C), and 1615 (C=C).

MS (DCI, NH$_3$): m/z 727 (MH$^+$, 5%), 596 (23), 595 (26), 594 (30), 147 (11), 132 (10), 131 (67), 92 (15), 91 (19), 90 (14), 76 (13), 75 (base), 74 (33), 73 (33), 58 (10), 56 (12), and 43 (10).

Exact Mass (DCI, NH$_3$/PEG): calculated for C$_{43}$H$_{79}$O$_3$Si$_3$ (MH$^+$): m/z 727.5337. Found: m/z 727.5345.

Preparation of (1S,14R,15S)-1α,25-dihydroxy-14(15)-cyclopropyl-6,7-dehydroprevitamin D$_3$ (8)

To a solution of dieyne 7 (109.6 mg, 0.1507 mmol) in 5 mL of THF under argon was added tetrabutylammonium fluoride (1.13 mL, 1 M in THF, 1.13 mmol). The reaction mixture was stirred at room temperature in the dark for 12 h. It was diluted with ethyl acetate and washed with brine (2×10 mL). The aqueous layer was extracted with ethyl acetate (2×10 mL), and the combined organic layer was dried (MgSO$_4$) and evaporated in vacuo. Flash chromatography of the residual oil (100% EtOAc) afforded after vacuum drying 59.6 mg (93%) of the triol 8 as a colorless oil, which was sufficiently pure for characterization and further reaction.

$^1$H-NHR (300 MHZ, CDCl$_3$): δ0.45 (dd, J~7.6, 4.3 Hz, 1H, H$_a$), 0.60 (apparent t, J~3.7 Hz, 1H, H$_b$), 0.85–2.60 (remaining ring and side chain hydrogens, series of m), 0.90 (d, J~6.6 Hz, 3H, C$_{21}$—Me), 0.92 (s, 3H, C$_{18}$—Me), 1.21 (s, 6H, C$_{26,27}$—2Me), 1.97 (br s, 3H, C$_{19}$—Me), 4.11 (m, 1H, H$_3$), 4.25 (apparent t, J~3.9 Hz, 1H, H$_1$), and 5.98 (apparent t, J~3.8 Hz, 1H, H$_9$).

$^{13}$C-NMR (75.5 MHZ, CDCl$_3$): δ15.0, 15.2, 18.7, 20.7, 20.8, 25.3, 29.2, 29.4, 32.5, 32.7, 34.4, 36.3, 37.9, 39.3, 40.0, 40.6, 44.4, 47.2, 63.6, 69.4, 71.1, 87.2, 91.3, 116.0, 125.0, 132.7, and 139.4.

IR (NaCl): ν3470 (O—H), 2940 (C—H), 2370 (C_C), and 1690 (C=C).

MS (DEI): m/z 426 (M$^+$, 38%), 408 (42), 391 (27), 390 (77), 261 (28), 259 (21), 219 (22), 195 (20), 181 (22), 179 (20), 167 (21), 165 (26), 131 (23), 129 (24), 128 (20), 115 (25), 105 (26), 91 (26), 83 (32), 69 (30), 59 (base), 55 (45), 45 (47), and 43 (86).

Exact Mass (DEI): calculated for C$_{28}$H$_{42}$O$_3$: m/z 426.3134. Found: m/z 426.3123.

Preparation of analog LO, (14R,15S)-14,15-methano-1α,25-Dihydroxyvitamin D$_3$ (10)

A stirred mixture of dienyne 8 (38.6 mg, 0.0905 mmol), Lindlar catalyst (112 mg), and quinoline (312 μL, 0.17 M in hexanes) in methanol (5 mL) was exposed to a positive pressure of hydrogen gas for 30 min. The mixture was filtered and concentrated to afford a residual oil which was purified by flash chromatography (elution with 80% EtOAc/hexane) to afford 38.6 mg of the crude previtamin 9. $^1$H-NMR analysis of the latter material showed the complete absence of starting material. A solution of the crude 9 (38.6 mg, 0.0905 mmol) in acetone (4 mL) was placed in a screw-capped vial and heated for 4 h in a constant temperature bath set at 80° C. The residue was concentrated under vacuum and purified by HPLC (80% EtOAc/hexane, 4 mL/min, Rainin Dynamax 60 A column) to afford after vacuum drying 21.6 mg (56%) of the vitamin 10 (Analog LO) and 9.7 mg (25%) of the previtamin form (9).

$^1$H-NMR (300 MHZ, CDCl$_3$): δ−0.08 (dd, J~7.6, 3.7 Hz, 1H, H$_a$), 0.70 (apparent t, J~3.2 Hz, 1H, H$_b$), 0.74 (s, 3H, C$_{18}$—Me), 0.80–2.00 (remaining ring and side chain hydrogens, series of m), 0.86 (d, J~6.5 Hz, 3H, C$_{21}$—Me), 1.20 (s, 6H, C$_{26,27}$—2Me), 2.28 (dd, J~13.4, 6.9 Hz, 1H), 2.58 (dd, J~13.4, 3.5 Hz, 1H), 2.75 (dt, J~13.4, 2.9 Hz, 1H), 4.21 (m, 1H, H$_3$), 4.40 (apparent t, J~5.8 Hz, 1H, H$_1$), 4.93 (s, 1H, H19), 5.30 (s, 1H, H$_{19}$), 5.90 (dd, J~11.4, 1.4 Hz, 1H, H$_6$ or H$_7$), and 6.29 (d, J~11.4 Hz, 1H, H6 or H7).

UV (100% EtOH): λ$_{max}$ 268 nm (ε 23,300); λ$_{min}$ 230 nm (ε 14,100).

MS (FAB+, EtOH/NBA): m/z 451 (MNa$^+$, 4%), 345 (NBA+K, 8), 329 (NBA+Na, 37), 307 (NBA, 23), 289 (NBA, 14), 192 (NBA+K, 39), 176 (NBA+Na, base), 154 (NBA, 86), and 136 (NBA, 61).

Exact Mass (FAB+, EtOH/NBA): calculated for C$_{28}$H$_{44}$O$_3$Na (MNa$^+$): m/z 451.3188. Found: m/z 451.3174.

What is claimed is:

1. A compound of the formula I

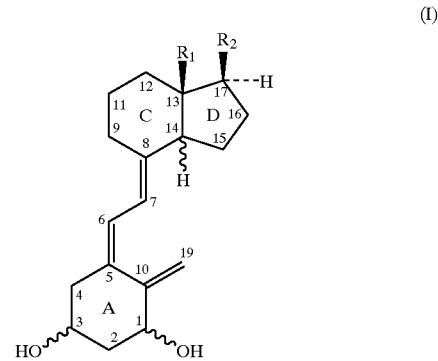

wherein R$_1$ is methyl;
wherein C1–C3 are positional isomers α and β in an α-βconfiguration;
wherein C5–C6 double bond is cis or trans;
wherein C7–C8 double bond is cis;
wherein C14 hydrogen is α;
wherein C16–C17 is a single bond; and
wherein R$_2$ is a substituent I-1

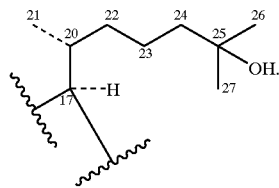

2. The compound of claim 1 wherein C5–C6 double bond is trans, namely the analog JS, 5,6-trans-7,8-cis-1α,25-dihydroxyvitamin D$_3$.

3. The compound of claim 1 wherein C5–C6 double bond is cis, namely the analog JR, 5,6-cis-7,8-cis-1α,25-dihydroxyvitamin D$_3$.

* * * * *